United States Patent
Pan et al.

(10) Patent No.: US 10,723,700 B2
(45) Date of Patent: *Jul. 28, 2020

(54) SALTS OF AN LSD1 INHIBITOR

(71) Applicant: Incyte Corporation, Wilmington, DE (US)

(72) Inventors: Yongchun Pan, Wilmington, DE (US); Wayne Han, West Chester, PA (US); Ganfeng Cao, Chadds Ford, PA (US); Zhongjiang Jia, Kennett Square, PA (US); Jiacheng Zhou, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/447,841

(22) Filed: Jun. 20, 2019

(65) Prior Publication Data

US 2019/0345106 A1 Nov. 14, 2019

Related U.S. Application Data

(62) Division of application No. 15/234,053, filed on Aug. 11, 2016, now Pat. No. 10,329,255.

(60) Provisional application No. 62/326,246, filed on Apr. 22, 2016, provisional application No. 62/204,105, filed on Aug. 12, 2015.

(51) Int. Cl.
*C07D 211/26* (2006.01)
*C07D 211/32* (2006.01)
*C07D 211/22* (2006.01)

(52) U.S. Cl.
CPC .......... *C07D 211/26* (2013.01); *C07D 211/22* (2013.01); *C07D 211/32* (2013.01)

(58) Field of Classification Search
None
See application file for complete search history.

(56) References Cited

U.S. PATENT DOCUMENTS

| | | | |
|---|---|---|---|
| 4,537,889 A | 8/1985 | Spitzer | |
| 4,625,040 A | 11/1986 | Georgiev et al. | |
| 5,658,857 A | 8/1997 | Andree et al. | |
| 5,932,223 A | 8/1999 | Burke et al. | |
| 7,759,386 B2 | 7/2010 | Benjain et al. | |
| 7,858,609 B2 | 12/2010 | Shaw et al. | |
| 8,115,000 B2 | 2/2012 | Rajagopalan et al. | |
| 8,349,210 B2 | 1/2013 | Xu et al. | |
| 8,383,154 B2 | 2/2013 | Bar-Shalom et al. | |
| 8,546,394 B2 | 10/2013 | Li | |
| 8,558,008 B2 | 10/2013 | Statler et al. | |
| 8,568,782 B2 | 10/2013 | Viscomi et al. | |
| 8,614,315 B2 | 12/2013 | Bilgic | |
| 8,853,408 B2 | 10/2014 | Johnson | |
| 9,493,442 B2 | 11/2016 | Wu et al. | |
| 9,493,450 B2 | 11/2016 | Wu et al. | |
| 9,527,835 B2 | 12/2016 | Wu et al. | |
| 9,670,210 B2* | 6/2017 | Wu | A61K 31/435 |
| 9,695,167 B2 | 7/2017 | Wu et al. | |
| 9,695,168 B2 | 7/2017 | Wu et al. | |
| 9,695,180 B2 | 7/2017 | Wu et al. | |
| 9,758,523 B2 | 9/2017 | Wu et al. | |
| 9,790,169 B2 | 10/2017 | Balog et al. | |
| 9,809,541 B2 | 11/2017 | Marx et al. | |
| 9,944,647 B2 | 4/2018 | He et al. | |
| 9,994,546 B2 | 6/2018 | Wu et al. | |
| 10,112,950 B2 | 10/2018 | Wu et al. | |
| 10,125,133 B2 | 11/2018 | Wu et al. | |
| 10,138,249 B2 | 11/2018 | Wu et al. | |
| 10,166,221 B2* | 1/2019 | Rocco | A61K 9/0053 |
| 10,174,030 B2* | 1/2019 | Wu | C07D 205/04 |
| 10,300,051 B2 | 5/2019 | Wu et al. | |
| 10,329,255 B2 | 6/2019 | Pan et al. | |
| 2002/0151549 A1 | 10/2002 | Hayakawa et al. | |
| 2004/0023972 A1 | 2/2004 | Sundermann et al. | |
| 2004/0058938 A1 | 3/2004 | Cullmann et al. | |
| 2004/0082635 A1 | 4/2004 | Hashimoto et al. | |
| 2004/0082781 A1 | 4/2004 | Hibi et al. | |
| 2004/0220189 A1 | 11/2004 | Sun et al. | |
| 2005/0009832 A1 | 1/2005 | Sun et al. | |
| 2005/0113283 A1 | 5/2005 | Solow-Cordero et al. | |
| 2006/0178399 A1 | 8/2006 | Nishizawa et al. | |
| 2006/0194842 A1 | 8/2006 | Uchida et al. | |
| 2006/0276339 A1 | 12/2006 | Windsor et al. | |
| 2007/0004772 A1 | 1/2007 | Sun et al. | |
| 2007/0128276 A1 | 6/2007 | Jain et al. | |

(Continued)

FOREIGN PATENT DOCUMENTS

BR 2011-01013 6/2013
CA 2831143 10/2012

(Continued)

OTHER PUBLICATIONS

Berge et al. "Pharmaceutical Salts". Journal of Pharmaceutical Sciences. Jan. 1977; 66(1):1-19. (Year: 1977).*
"LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.
Adamo et al., "LSD1 and pluripotency: a new player in the network," Cell Cycle, Oct. 2011, 10(19): 3215-6.

(Continued)

*Primary Examiner* — Leslie A. Royds Draper
(74) *Attorney, Agent, or Firm* — Fish & Richardson P.C.

(57) ABSTRACT

The present disclosure relates to tosylate salts 1-{[4-(methoxymethyl)-4-({[(1R,2S)-2-phenylcyclopropyl]amino}methyl)piperidin-1-yl]methyl}cyclobutanecarboxylic acid, methods of preparation thereof, and intermediates in the preparation thereof, which are useful in the treatment of the LSD1-associated or mediated diseases such as cancer.

54 Claims, 56 Drawing Sheets

Specification includes a Sequence Listing.

(56) References Cited

U.S. PATENT DOCUMENTS

| | | |
|---|---|---|
| 2007/0191395 A1 | 8/2007 | Kawakami |
| 2007/0191421 A1 | 8/2007 | Buettelmann et al. |
| 2008/0249154 A1 | 10/2008 | Ohmoto et al. |
| 2009/0004281 A1 | 1/2009 | Nghiem et al. |
| 2009/0047336 A1 | 2/2009 | Yang et al. |
| 2009/0203690 A1 | 8/2009 | Akritopoulou-Zanze et al. |
| 2009/0318436 A1 | 12/2009 | Albrecht et al. |
| 2010/0113441 A1 | 5/2010 | Siegel et al. |
| 2010/0143481 A1 | 6/2010 | Shenoy et al. |
| 2010/0209489 A1 | 8/2010 | Liang et al. |
| 2010/0316712 A1 | 12/2010 | Nangia et al. |
| 2011/0105457 A1 | 5/2011 | Taniyama et al. |
| 2011/0112067 A1 | 5/2011 | Hartmann et al. |
| 2012/0004262 A1 | 1/2012 | Guibourt et al. |
| 2012/0108500 A1 | 5/2012 | Sakane et al. |
| 2012/0220582 A1 | 8/2012 | Mitchell et al. |
| 2012/0283266 A1 | 11/2012 | Ortega Munoz et al. |
| 2012/0322877 A1 | 12/2012 | Casero et al. |
| 2013/0035377 A1 | 2/2013 | Minucci et al. |
| 2013/0040946 A1 | 2/2013 | Siegel et al. |
| 2013/0090386 A1 | 4/2013 | Ortega Munoz et al. |
| 2013/0095067 A1 | 4/2013 | Baker et al. |
| 2013/0109751 A1 | 5/2013 | Salvatore |
| 2013/0197013 A1 | 8/2013 | Fyfe et al. |
| 2013/0203754 A1 | 8/2013 | Yang et al. |
| 2013/0217878 A1 | 8/2013 | Lizuka et al. |
| 2013/0231342 A1 | 9/2013 | Munoz et al. |
| 2013/0303545 A1 | 11/2013 | Maes et al. |
| 2014/0011857 A1 | 1/2014 | Casero et al. |
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0064250 A1 | 3/2015 | Ghebre-Sellassie et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1* | 8/2015 | Wu ................ C07D 211/14 514/210.18 |
| 2015/0232436 A1 | 8/2015 | Baker et al. |
| 2015/0265683 A1 | 9/2015 | Sahib et al. |
| 2015/0296852 A1 | 10/2015 | Penhasi et al. |
| 2016/0009711 A1 | 1/2016 | Wu et al. |
| 2016/0009712 A1 | 1/2016 | Wu et al. |
| 2016/0009720 A1 | 1/2016 | Wu et al. |
| 2016/0009721 A1 | 1/2016 | Wu et al. |
| 2016/0289238 A1 | 4/2016 | He et al. |
| 2017/0044101 A1 | 2/2017 | Pan et al. |
| 2017/0112816 A1 | 4/2017 | Wu et al. |
| 2017/0121302 A1 | 5/2017 | Wu et al. |
| 2017/0158633 A1 | 6/2017 | Wu et al. |
| 2017/0304282 A1 | 10/2017 | Rocco et al. |
| 2017/0342070 A1* | 11/2017 | Wu ................ A61K 31/454 |
| 2017/0362245 A1 | 12/2017 | Wu et al. |
| 2017/0369487 A1 | 12/2017 | Wu et al. |
| 2017/0369488 A1 | 12/2017 | Wu et al. |
| 2017/0369497 A1 | 12/2017 | Wu et al. |
| 2018/0118765 A1 | 5/2018 | Brias et al. |
| 2019/0040058 A1 | 2/2019 | Wu et al. |
| 2019/0055250 A1 | 2/2019 | He et al. |
| 2019/0062301 A1 | 2/2019 | Wu et al. |
| 2019/0106426 A1 | 4/2019 | Wu et al. |
| 2019/0119272 A1 | 4/2019 | Wu et al. |
| 2019/0152976 A1 | 5/2019 | Wu et al. |
| 2019/0211014 A1* | 7/2019 | Wu ................ A61K 31/397 |
| 2019/0307736 A1 | 10/2019 | Rocco et al. |
| 2020/0024277 A1 | 1/2020 | Wu et al. |

FOREIGN PATENT DOCUMENTS

| | | |
|---|---|---|
| CA | 2844525 | 2/2013 |
| CA | 2849564 | 4/2013 |
| CA | 2887598 | 4/2014 |
| CL | 201400314 | 8/2014 |
| CL | 201400988 | 11/2014 |
| CL | 201702482 | 4/2018 |
| CL | 201702494 | 5/2018 |
| CL | 201800374 | 7/2019 |
| CN | 101987082 | 3/2011 |
| CN | 102247321 | 11/2011 |
| CN | 102397552 | 4/2012 |
| CN | 102579381 | 7/2012 |
| CN | 102772444 | 11/2012 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| CN | 104173313 | 12/2014 |
| CN | 105232488 | 1/2016 |
| DE | 102006041292 | 3/2008 |
| EP | 0179254 | 4/1986 |
| EP | 0404190 | 12/1990 |
| EP | 0430385 | 6/1991 |
| EP | 2168579 | 3/2010 |
| EP | 2524918 | 11/2012 |
| EP | 2740474 | 6/2014 |
| EP | 2743256 | 6/2014 |
| EP | 3105218 | 12/2016 |
| EP | 3277689 | 2/2018 |
| FR | 2662163 | 11/1991 |
| FR | 2920090 | 2/2009 |
| FR | 2920091 | 2/2009 |
| IN | 2007MU01698 | 3/2009 |
| JP | 2844351 | 1/1999 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |
| JP | 2010070503 | 4/2010 |
| JP | 2016044170 | 4/2016 |
| WO | WO 1988/004298 | 6/1988 |
| WO | WO 1993/025553 | 12/1993 |
| WO | WO 1994/018198 | 8/1994 |
| WO | WO 1995/012594 | 5/1995 |
| WO | WO 1999/024434 | 5/1999 |
| WO | WO 01/25237 | 4/2001 |
| WO | WO 2001/27119 | 4/2001 |
| WO | WO 2001/83481 | 8/2001 |
| WO | WO 2002/000196 | 1/2002 |
| WO | WO 2002/06286 | 1/2002 |
| WO | WO 2002/034748 | 5/2002 |
| WO | WO 2002/38562 | 5/2002 |
| WO | WO 2002/038568 | 5/2002 |
| WO | WO 2002/051831 | 7/2002 |
| WO | WO 2002/072549 | 9/2002 |
| WO | WO 2003/006471 | 1/2003 |
| WO | WO 2003/044021 | 5/2003 |
| WO | WO 2003/062392 | 7/2003 |
| WO | WO 2004/017950 | 3/2004 |
| WO | WO 2004/021989 | 3/2004 |
| WO | WO 2004/058762 | 7/2004 |
| WO | WO 2004/072081 | 8/2004 |
| WO | WO 2004/074290 | 9/2004 |
| WO | WO 2004/089380 | 10/2004 |
| WO | WO 2004/089416 | 10/2004 |
| WO | WO 2004/096131 | 11/2004 |
| WO | WO 2004/108692 | 12/2004 |
| WO | WO 2005/007658 | 1/2005 |
| WO | WO 2005/025558 | 3/2005 |
| WO | WO 2005/035532 | 4/2005 |
| WO | WO 2005/042537 | 5/2005 |

(56) References Cited

FOREIGN PATENT DOCUMENTS

| | | |
|---|---|---|
| WO | WO 2005/044793 | 5/2005 |
| WO | WO 2005/097052 | 10/2005 |
| WO | WO 2006/015263 | 2/2006 |
| WO | WO 2006/018727 | 2/2006 |
| WO | WO 2006/038116 | 4/2006 |
| WO | WO 2006/057946 | 6/2006 |
| WO | WO 2006/058752 | 6/2006 |
| WO | WO 2006/073938 | 7/2006 |
| WO | WO 2006/074041 | 7/2006 |
| WO | WO 2006/113704 | 10/2006 |
| WO | WO 2006/131003 | 12/2006 |
| WO | WO 2006/135667 | 12/2006 |
| WO | WO 2006/135795 | 12/2006 |
| WO | WO 2006/138695 | 12/2006 |
| WO | WO 2006/138734 | 12/2006 |
| WO | WO 2007/022529 | 2/2007 |
| WO | WO 2007/028051 | 3/2007 |
| WO | WO 2007/058942 | 5/2007 |
| WO | WO 2007/074491 | 7/2007 |
| WO | WO 2007/095588 | 8/2007 |
| WO | WO 2007/113226 | 10/2007 |
| WO | WO 2007/145921 | 12/2007 |
| WO | WO 2007/149478 | 12/2007 |
| WO | WO 2008/005262 | 1/2008 |
| WO | WO 2008/005423 | 1/2008 |
| WO | WO 2008/005908 | 1/2008 |
| WO | WO 2008/008539 | 1/2008 |
| WO | WO 2008/011560 | 1/2008 |
| WO | WO 2008/027812 | 3/2008 |
| WO | WO 2008/037607 | 4/2008 |
| WO | WO 2008/045393 | 4/2008 |
| WO | WO 2008/056176 | 5/2008 |
| WO | WO 2008/064157 | 5/2008 |
| WO | WO 2008/065198 | 6/2008 |
| WO | WO 2008/110523 | 9/2008 |
| WO | WO 2008/113559 | 9/2008 |
| WO | WO 2008/125111 | 10/2008 |
| WO | WO 2008/130951 | 10/2008 |
| WO | WO 2008/141239 | 11/2008 |
| WO | WO 2008/154241 | 12/2008 |
| WO | WO 2008/156614 | 12/2008 |
| WO | WO 2008/157752 | 12/2008 |
| WO | WO 2009/010530 | 1/2009 |
| WO | WO 2009/017701 | 2/2009 |
| WO | WO 2009/017954 | 2/2009 |
| WO | WO 2009/023179 | 2/2009 |
| WO | WO 2009/028900 | 3/2009 |
| WO | WO 2009/045753 | 4/2009 |
| WO | WO 2009/047514 | 4/2009 |
| WO | WO 2009/047563 | 4/2009 |
| WO | WO 2009/048993 | 4/2009 |
| WO | WO 2009/085230 | 7/2009 |
| WO | WO 2009/085980 | 7/2009 |
| WO | WO 2009/091374 | 7/2009 |
| WO | WO 2009/114180 | 9/2009 |
| WO | WO 2009/114512 | 9/2009 |
| WO | WO 2009/128520 | 10/2009 |
| WO | WO 2009/138176 | 11/2009 |
| WO | WO 2010/010184 | 1/2010 |
| WO | WO 2010/010187 | 1/2010 |
| WO | WO 2010/010188 | 1/2010 |
| WO | WO 2010/010189 | 1/2010 |
| WO | WO 2010/019899 | 2/2010 |
| WO | WO 2010/021607 | 2/2010 |
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/090614 | 8/2010 |
| WO | WO 2010/091067 | 8/2010 |
| WO | WO 2010/091824 | 8/2010 |
| WO | WO 2010/101537 | 9/2010 |
| WO | WO 2010/104306 | 9/2010 |
| WO | WO 2010/107404 | 9/2010 |
| WO | WO 2010/108059 | 9/2010 |
| WO | WO 2010/113942 | 10/2010 |
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/149438 | 12/2011 |
| WO | WO 2011/160548 | 12/2011 |
| WO | WO 2012/003392 | 1/2012 |
| WO | WO 2012/006959 | 1/2012 |
| WO | WO 2012/007345 | 1/2012 |
| WO | WO 2012/009475 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/054698 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |
| WO | WO 2013/025805 | 2/2013 |
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/051698 | 3/2014 |
| WO | WO 2014/055955 | 4/2014 |
| WO | WO 2014/058071 | 4/2014 |
| WO | WO 2014/078479 | 5/2014 |

(56) References Cited

FOREIGN PATENT DOCUMENTS

| | | |
|---|---|---|
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/153001 | 9/2014 |
| WO | WO 2014/164867 | 10/2014 |
| WO | WO 2014/194280 | 12/2014 |
| WO | WO 2014/205213 | 12/2014 |
| WO | WO 2014/205223 | 12/2014 |
| WO | WO 2013/022047 | 3/2015 |
| WO | WO 2015/031564 | 3/2015 |
| WO | WO 2015/036512 | 3/2015 |
| WO | WO 2015/089192 | 6/2015 |
| WO | WO 2015/122187 | 8/2015 |
| WO | WO 2015/122188 | 8/2015 |
| WO | WO 2015/123424 | 8/2015 |
| WO | WO-2015123465 A1 * | 8/2015 |
| WO | WO 2015/153720 | 10/2015 |
| WO | WO 2015/155281 | 10/2015 |
| WO | WO 2015/155297 | 10/2015 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |
| WO | WO 2016/055394 | 4/2016 |
| WO | WO 2016/055797 | 6/2016 |
| WO | WO 2016/161282 | 10/2016 |
| WO | WO 2017/027678 | 2/2017 |
| WO | WO 2017/130933 | 8/2017 |
| WO | WO 2017/184934 | 10/2017 |
| WO | WO 2018/136634 | 7/2018 |
| WO | WO 2018/166493 | 9/2018 |

OTHER PUBLICATIONS

Adamo et al., "LSD1 regulates the balance between self-renewal and differentiation in human embryonic stem cells," Nat. Cell Biol, Jun. 2011, 13(6): 652-9.
Anand and Marmorstein, "Structure and mechanism of lysine-specific demethylase enzymes," J Biol Chem, Dec. 2007, 282(49): 35425-9.
Atzrodt et al.,"The Renaissance of H/D Exchange," Angew. Chem. Int. Ed., Sep. 21, 2007, 46:7744-7765.
Balamuth "Ewings sarcoma" Lancet Oncology (2010), 11(2), 184-192.
Baron et al., "Molecular Mimicry and Ligand Recognition in Binding and Catalysis by the Histone Demethylase LSD1-CoREST Complex," Structure, Feb. 2011, 19: 212-220.
Bauer et al., "Reawakening fetal hemoglobin: prospects for new therapies for the β-globin disorders," Blood, Oct. 2012, 120(15): 3945-53.
Beck and Blanpain, "Unravelling cancer stem cell potential," Nat Rev Cancer, Oct. 2013, 13(10): 727-38.
Benelkebir et al., "Enantioselective synthesis of tranylcypromine analogues as lysine demethylase (LSD1) inhibitors," Bioorganic & Medicinal Chemistry, 2011, 19: 3709-3716.
Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.
Berge and Robiette, "Development of a Regioselective N-Methylation of (Benz)imidazoles Providing the More Sterically Hindered Isomer," The Journal of Organic Chemistry, 2013, A-D.
Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.
Binda et al., "Molecular Insights into Human Monoamine Oxidase B Inhibition by the Glitazone Antidiabetes Drugs," ACS Med. Chem. Letter, 2012, 3: 39-42.
Blom et al., "Optimizing Preparative LC/MS Configurations and Methods for Parallel Synthesis Purification," J. Comb. Chem., 2003, 5(5): 670-683.
Blom et al., "Preparative LC-MS Purification: Improved Compound-Specific Method Optimization," J. Comb. Chem., 2004, 6(6): 874-883.
Blom, "Two-Pump at-Column-Dilution Configuration for Preparative Liquid Chomratography-Mass Spectrometry," J. Comb. Chem, 2002, 4(4): 295-301.
Cain, "AML takes LSD1," SciBX, Apr. 2012, 1-3.
Carey, FA. Organic Chemistry 6th Ed. McGraw Hill. 2006, chapter 1, p. 9.
Cao et al., "One-Pot Regiospecific Synthesis of Imidazo[1,2-a]pyridines: A Novel, Metal-Free, Three-Component Reaction for the Formation of C—N, C—O, and C—S Bonds," Org. Lett., 2013, A-D.
Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.
Chen et al., "Lysine-specific histone demethylase 1 (LSD1): A potential molecular target for tumor therapy," Crit Rev Eukaryot Gene Expre, 2012, 22(1): 53-9.
Chilean Opposition in Chilean Application No. 2021-2016, dated Dec. 23, 2016, 3 pages (English Translation).
Chilean Office Action in Chilean Application No. 2021-2016, dated Apr. 10, 2018, 14 pages (English Translation).
Chilean Office Action in Chilean Application No. 2021-2016, dated Oct. 19, 2018, 16 pages.
Chinese Office Action in Chinese Application No. 201580017095, dated Mar. 30, 2018, 11 pages (English Translation).
Chinese Office Action in Chinese Application No. 201580017095, dated Dec. 17, 2018, 11 pages (English Translation).
Chinese Office Action in Chinese Application No. 201580019205.7, dated Nov. 27, 2019, 10 pages (English Translation).
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
ClinicalTrials.gov, "An Open-Label, Dose-Escalation/Dose-Expansion Safety Study of INC059872 in Subjects with Advanced Malignancies," [retrieved on Nov. 5, 2018] retrieved from <https://clinicaltrials.gov/ct2/show/NCT02712905> 7 pages.
ClinicalTrials.gov, "IMG-7289, with and without ATRA, in patients with advanced myeloid malignancies," Jul. 25, 2016, [last update Feb. 26, 2019] retrieved from URL <https://clinicaltrials.gov/ct2/show/NCT02842827>, 6 pages.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, Jun. 1, 2015, 1-31.
Cui, Shuaiying, "Nuclear Receptors TR2 and TR4 Recruit Multiple Epigenetic Transcriptional Corepressors That Associate Specifically with the Embryonic-Type Globin Promoters in Differentiated Adult Erythroid Cells," Molecular and Cellular Biology, Aug. 31, 2011, 31(16): 3298-3311.
Culhane and Cole, "LSD1 and the chemistry of histone demethylation," Current Opinion in Chemical Biology, 2007, 11: 561-568.
Culhane et al., "A Mechanism-Based Inactivator for Histone Demethylase LSD1," J. Am. Chem. Soc., 2006, 128: 4536-4537.
Culhane et al., "Comparative Analysis of Small Molecules and Histone Substrate Analogues as LSD1 Lysine Demethylase Inhibitors," J. Am. Chem. Soc., 2010, 132: 3164-3176.
Colombian Office Action in Colombian Application No. NC20160001817, dated Mar. 20, 2018, 9 pages.
Dancy et al., "Azalysine Analogues as Probes for Protein Lysine Deacetylation and Demethylation," J. Am. Chem. Soc., 2012, 5138-5148.
Dawson and Kouzarides, "Cancer epigenetics: from mechanism to therapy," Cell, Jul. 2012, 150(1): 12-27.

(56) References Cited

OTHER PUBLICATIONS

Dhanak, "Cracking the Code: The Promise of Epigenetics," ACS Med. Chem. Letter, 2012, 3: 521-523.
Dhudshia and Thadani, "Diastereoselective allylation and crotylation of N-unsubstituted imines derived from ketones," Chem. Commun., 2005, 33 pages.
Dhudshia et al., "Diastereoselective allylation and crotylation of N-unsubstituted imines derived from ketones," Chem Commun, 2005, 5551-5553.
Ding et al., "LSD1-mediated epigenetic modification contributes to proliferation and metastasis of colon cancer," Br J Cancer, Aug. 2013, 109(4): 994-1003.
Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.
Eurasian Office Action in Eurasian Application No. 201691620, dated Mar. 16, 2017, 6 pages (English Translation).
Eurasian Office Action in Eurasian Application No. 201691594, dated Sep. 27, 2017, 4 pages (English Translation).
Eurasian Office Action in Eurasian Application No. 201792205, dated Apr. 4, 2018, 6 pages (English Translation).
European Search Report from European Application No. 18160157, dated Sep. 3, 2018, 6 pages.
European Extended Search Report in European Application No. 19190014.1, dated Jan. 23, 2020, 7 pages.
European Extended Search Report in European Application No. 19190494.5 dated Jan. 29, 2020, 10 pages.
European Examination Report in European Application No. 15707007.9, dated Feb. 27, 2018, 3 pages.
Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.
Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.
Forneris et al., "LSD1: oxidative chemistry for multifaceted functions in chormatin regulation," Cell Press, Mar. 2008, 181-189.
Forneris, F., et al., Structural basis of LSD1-CoREST selectivity in histone H3 recognition. J Biol Chem, 2007. 282(28): p. 20070-4.
Ganesan, "Targeting Epigenetic Demethylation," University of East Anglia (School of Pharmacy), PowerPoint presentation, Presented from the World Epigenetics Summit, London, Jul. 24, 2012, 26 pages.
Garson et al., "Models of ovarian cancer—are we there yet?," Mol Cell Endocrinol., Jul. 15, 2005, 239(1-2):15-26.
Ge et al., "Pd-Catalyzed α-Arylation of α,α-Difluoroketones with Aryl Bromides and Chlorides. A Route to Difluoromethylarenes," J. Am. Chem. Soc., 2014, A-D.
George et al., "Soft Tissue and Uterine Lelomyosarcoma," J Clin Oncol., Dec. 8, 2017, 36(2):144-150.
Ghosh and Barik, "Formulation and in vitro evaluation of once daily sustained release formulation of aceclofenac," Tropical Journal of Pharmaceutical Research, 2010, 9(3):265-273.
Gonzalez et al., "Selective and Potent Morpholinone Inhibitors of the MDM2-p53 Protein-Protein Interaction," J. Med. Chem., 2013, A-Q.
Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.
Greaves and Gribben, "The role of B7 family molecules in hematologic malignancy," Blood, Jan. 2013, 121(5): 734-44.
Gui et al., "C—H Methylation of Heteroarenes Inspired by Radical SAM Methyl Transferase," J. Am. Chem. Soc., 2014, A-D.
Guiles et al. "preparation of triazolopyrimidine derivatives as P2T receptor antagonists," CA130:168386 (1999).
Hackam et al., "Translation of research evidence from animals to humans," JAMA, Oct. 2006, 296(14), 1731-1732.
Hakimi et al., "A core-BRAF35 complex containing histone deacetylase mediates repression of neuronal-specific genes," Proc Natl Acad Sci USA, May 2002, 99(11): 7420-5.
Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.
Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.
Han et al., "Synergistic re-activation of epigenetically silenced genes by combinatorial inhibition of DNMTs and LSD1 in cancer cells," pLoS One, Sep. 2013, 8(9): e75136.
Harris et al., "The histone demethylase KDM1A sustains the oncogenic potential of MLL-AF9 leukemia stem cells," Cancer Cell, Apr. 2012, 21(4): 473-87.
Hayami et al., "Overexpression of LSD1 contributes to human carcinogenesis through chromatin regulation in various cancers," Int J Cancer, Feb. 2011, 128(3): 574-86.
Hazeldine et al., "Low Molecular Weight Amidoximes that Act as Potent Inhibitors of Lysine-Specific Demethylase 1," J. Med. Chem., 2012, 55: 7378-7391.
Hesp et al., "Expedient Synthesis of α-Heteroaryl Piperidines Using a Pd-Catalyzed Suzuki Cross-Coupling—Reduction Sequence," Org. Lett., 2013, A-C.
Hicken et al., "Discovery of a Novel Class of Imidazo[1,2-a]Pyridines with Potent PDGFR Activity and Oral Bioavailability," ACS Med. Chem. Lett., 2013, A-F.
Hitchin et al., "Development and evaluation of selective, reversible LSD1 inhibitors derived from fragments," Med. Chem. Commun., 2013, 4: 1513-1522.
Hoffmann et al., "The role of histone demethylases in cancer therapy," Molecular Oncology, 2012, 6: 683-703.
Hou and Yu, "Structural insights into histone lysine demethylation," Current Opinion in Structural Biology, 2010, 20: 739-748.
Hruschka et al., "Fluorinated phenylcyclopropylamines. Part 5: Effects of electron-withdrawing or -donating aryl substituents on the inhibition of monoamine oxidases A and B by 2-aryl-2-fluoro-cyclopropylamines," Bioorganic & Medicinal Chemistry, 2008, 16: 7148-7166.
Huang et al., "p53 is regulated by the lysine demethylase LSD1," Nature, Sep. 2007, 449(7158): 105-8.
Huang et al., "Rhodium(III)-Catalyzed Direct Selective C(5)—H Oxidative Annulations of 2-Substituted Imidazoles and Alkynes by Double C—H Activation," Organic Letters, Feb. 2013, 15(8): 1878-1881.
Improper Markush Fed. Reg. 76(27) p. 7612-75, slide 1, 64-67 (2011).
International Preliminary Report on Patentability in International Application No. PCT/US2015/015600, dated Aug. 25, 2016, 7 pages.
International Preliminary Report on Patentability in International Application No. PCT/US2015/015635, dated Aug. 16, 2016, 8 pages.
International Preliminary Report on Patentability in International Application No. PCT/US2015/015663, dated Aug. 16, 2016, 7 pages.
International Preliminary Report on Patentability in International Application No. PCT/US2015/015706, dated Aug. 16, 2016, 10 pages.
International Preliminary Report on Patentability in International Application No. PCT/US2015/039734, dated Jan. 10, 2017, 10 pages.
International Preliminary Report on Patentability in International Application No. PCT/US2015/039706, dated Jan. 10, 2017, 10 pages.

(56) References Cited

OTHER PUBLICATIONS

International Preliminary Report on Patentability in International Application No. PCT/US2015/039724, dated Jan. 10, 2017, 10 pages.
International Preliminary Report on Patentability in International Application No. PCT/US2015/039718, dated Jan. 10, 2017, 9 pages.
International Preliminary Report on Patentability in International Application No. PCT/US2016/025550, dated Oct. 2, 2017, 8 pages.
International Preliminary Report on Patentability in International Application No. PCT/US2016/046497, dated Feb. 22, 2018, 8 pages.
International Preliminary Report on Patentability in International Application No. PCT/US2017/028756, dated Oct. 23, 2018, 8 pages.
International Search Report and Written Opinion in International Application No. PCT/US2015/015600, dated May 18, 2015, 9 pages.
International Search Report and Written Opinion in International Application No. PCT/US2015/015635, dated May 8, 2015, 10 pages.
International Search Report and Written Opinion in International Application No. PCT/US2015/015663, dated May 6, 2015, 10 pages.
International Search Report and Written Opinion in International Application No. PCT/US2015/015706, dated May 6, 2015, 16 pages.
International Search Report and Written Opinion in International Application No. PCT/US2015/039718, dated Sep. 15, 2015, 13 pages.
International Search Report and Written Opinion in International Application No. PCT/US2015/039724, dated Sep. 15, 2015, 14 pages.
International Search Report and Written Opinion in International Application No. PCT/US2015/039734, dated Sep. 18, 2015, 14 pages.
International Search Report and Written Opinion in International Application No. PCT/US2016/025550, dated Aug. 30, 2016, 12 pages.
International Search Report and Written Opinion in International Application No. PCT/US2016/046497, dated Oct. 21, 2016, 13 pages.
International Search Report and Written Opinion in International Application No. PCT/US2015/039706, dated Sep. 16, 2015, 12 pages.
International Search Report and Written Opinion in International Application No. PCT/US2017/028756, dated Jul. 3, 2017, 23 pages.
International Search Report and Written Opinion in International Application No. PCT/US2019/048725, dated Jan. 3, 2020, 19 pages.
Invitation to Pay Fees in International Application No. PCT/US2019/048725, dated Oct. 30, 2019, 12 pages.
Jalluri, Drug Analysis Table, LSD1 KDM1a Cortellis Update, retrieved on May 6, 2013, 3 pages.
Jordan, "Tamoxifen: A Most Unlikely Pioneering Medicine," Nature Reviews: Drug Discovery, Mar. 2003, 2:205-213.
Kahl et al., "Androgen Receptor Coactivators Lysine-Specific Histone Demethylase 1 and Four and a Half LIM Domain Protein 2 Predict Risk of Prostate Cancer Recurrence," Cancer Res., Dec. 2006, 66(23): 11341-11347.
Kakizawa et al., "Histone H3 peptide based LSD1-selective inhibitors," Bioorganic & Medicinal Chemistry Letters, 2015, 25: 1925-1928.
Karytinos et al., "A novel mammalian flavin-dependent histone demethylase," J Biol Chem, Jan. 2009, 284(26): 17775-82.
Kelly and Lipshutz, "Chemoselective Reductions of Nitroaromatics in Water at Room Temperature," Org. Lett., 2013, A-D.
Kerekes et al., "Aurora Kinase Inhibitors Based on the Imidazo[1,2-a]pyrazine Core: Fluorine and Deuterium Incorporation Improve Oral Absorption and Exposure," J. Med. Chem. Dec. 3, 2011, 54:201-210.
Kettle et al., "Diverse Heterocyclic Scaffolds as Allosteric Inhibitors of AKT," Journal of Medicinal Chemistry, Mar. 2012, 55(3): 1261-1273.
Khan et al., "An Overview of Phenylcyclopropylamine Derivatives: Biochemical and Biological Significance and Recent Developments," Medicinal Research Reviews, 2012, 874-910.
Khoury et al., "Efficient Assembly of Iminodicarboxamides by a "Truly" Four-Component Reaction," Angew. Chem. Int. Ed., 2012, 51: 10280-10283.
Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.
Kjer-Nielsen et al., "MR1 presents microbial vitamin B metabolites to MAIT cells," Nature, Nov. 2012, 491: 717-725.
Kocienski, PJ. Et al. Protecting Groups. Thieme. 2005, p. 52.
Kong et al., "Immunohistochemical expression of RBP2 and LSD1 in papillary thyroid carcinoma," Rom J Morphol Embryol, 2013, 54(3): 499-503.
Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.
Kontaki and Talianidis, "Lysine methylation regulates E2F1-induced cell death," Mol Cell, Jul. 2010, 39(1): 152-60.
Kooistra and Helin, "Molecular mechanisms and potential functions of histone demethylases," Nat Rev Mol Cell Biol, Apr. 2012, 13(5): 297-311.
Kuroyanagi et al., "Novel anti fungal agents: Triazolopyridines as inhibitors of beta-1,6-glucan synthesis," Bioorganic & Medicinal Chemistry, Aug. 2010, 18(16):5845-5854.
Kuroyanagi et al., "1,3-Benzoxazole-4-carbonitrile as a novel antifungal scaffold of beta-1,6-glucan synthesis inhibitors," Bioorganic & Medicinal Chemistry, Nov. 2010, 18(21):7593-7606.
Kutz et al., "3,5-Diamino-1,2,4-triazoles as a novel scaffold for potent, reversible LSD1 (KDM1A) inhibitors," Med. Chem. Commun., 2014, 5: 1863-1870.
Lan et al., "Recognition of unmethylated histone H3 lysine 4 links BHC80 to LSD1-mediated gene repression," Nature, 2007, 718-723.
Larsen and Hartwig, "Iridium-Catalyzed C—H Borylation of Heteroarenes: Scope, Regioselectivity, Application to Late-Stage Functionalization, and Mechanism," J. Am. Chem. Soc., 2013, A-M.
Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.
Liang et al "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS One, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Lynch et al., "LSD1 Inhibition: A therapeutic strategy in cancer?," Expert Opinion on Therapeutic Targets, 2012, 16(12): 1239-1249.

(56) References Cited

OTHER PUBLICATIONS

Masakatu et al., Medicinal Chemistry, 1995, 1:98-99.
Merck KGaA, "Product comparison-EMD4Biosciences," Comparison of LSD1 inhibitors, EMD Millipore USA, retrieved on May 6, 2013, 3 pages.
Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistry, 2010, 49: 6494-6503.
Moon et al., "Copper-Catalyzed Chan-Lam Coupling between Sulfonyl Azides and Boronic Acids at Room Temperature," Org. Lett., 2013, A-D.
Moormann et al., "Potential Antisecretory Antidiarrheals. 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Muntean and Hess, "Biological Perspectives: Epigenetic Dysregulation in Cancer," Am J of Pathol., Oct. 2009, 175(4):1353-1361.
Neelamegam et al., "Brain-penetrant LSD1 inhibitors can block memory consolidation," Supplementary Data, 2012, 24 pages.
Neelamegam et al., "Brain-Penetrant LSD1 Inhibitors Can Block Memory Consolidation," ACS Chem. Neurosci., 2012, 3:120-128.
No Author, "FS14 Myelofibrosis Facts," Leukemia & Lymphoma Society, [last updated Apr. 2012] retrieved from URL <http://www.lls.org/sites/default/files/file_assets/FS14_Myelofibrosis_Fact%20Sheet_Final9.12.pdf>, 9 pages.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery Mechanism," Supporting Information, Angew. Chem. Int. Ed., 2013, 52: 8620-8624.
Patani et al., "Bioisosterism: A Rational Approach in Drug Design," Chemical Reviews, 1996, 96: 3147-3176.
Peturssion et al., "Protecting Groups in Carbohydrate Chemistry," J. Chem. Educ., Nov. 1, 1997, 74:1297.
Pitt "Heteroaromatic Rings of the Future" J. Med. Chem. 2009, 52, 2952-2963.
Portela and Esteller, "Epigenetic modifications and human disease," Nat Biotechnol, Oct. 2010, 28(10): 1057-68.
Potts et al., "The mass spectra of somes-triazolo[4,3-a]pyrazines," Organic Mass Spectrometry, Jun. 1971, 5(6): 663-674.
Pozharskii et. al. Heterocycles in Life and Society Wiley, 1997, pp. 1-6.
Rambaldi et al., "From Palliation to Epigenetic Therapy in Myelofibrosis," Hematology Am Soc Hematol Educ Program., 2008, 83-91.
*Remington's Pharmaceutical Sciences*, 17$^{th}$ Ed., (Mack Publishing Company, Easton, 1985), p. 1418.
Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Rotilli and Mai, "Targeting Histone Demethylases: A New Avenue for the Fight against Cancer," Genes and Cancer, 2011, 2(6): 663-679.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.

Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Sale "Models of ovarian cancer metastasis: Murine models," Drug Discov Today Dis Models., Jun. 1, 2006, 3(2):149-154.
Samann et al., "Full Functionalization of the Imidazole Scaffold by Selective Metalation and Sulfoxide/Magnesium Exchange," Angew. Chem. Int. Ed., 2013, 52: 1-6.
Sankar et al., "Reversible LSD1 inhibition interferes with global EWS/ETS transcriptional activity and impedes Ewing sarcoma tumor growth," Clin Cancer Res., Sep. 1, 2014, 20(17):4584-4597.
Sankaran, "Anemia: progress in molecular mechanisms and therapies," Nature Medicine, 2015, 21(3): 221-230.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.
Schmitt et al., "Nonpeptidic Propargylamines as Inhibitors of Lysine Specific Demethylase 1 (LSD1) with Cellular Activity," J. Med. Chem., 2013, A-I.
Schulte et al., "Lysine-Specific Demethylase 1 is Strongly Expressed in Poorly Differentiated Neuroblastoma: Implications for Therapy," Cancer Res, 2009, 69(5): 2065-71.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elecated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.
Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Shih et al., "The role of mutations in epigenetic regulators in myeloid malignancies," Nat Rev Cancer., Sep. 2012, 12(9):599-612.
Singh et al., "Inhibition of LSD1 sensitizes gliobastoma cells to histone deacetylase inhibitors," Neuro Oncol, Aug. 2011, 13(8): 894-903.
Son et al., "Structure of human monoamine oxidase A at 2.2-A resolution: The control of opening the entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primary, Secondary, Tertiary) to Alcohols using $SmI_2/Amine/H_2O$ under Mild Conditions," J. Am. Chem. Soc., 2013, A-D.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.

(56) References Cited

OTHER PUBLICATIONS

Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.
Ueda et al., "Identification of Cell-Active Lysine Specific Demethylase 1-Selective Inhibitors," J. Am. Chem. Soc., 2009, 131: 17536-17537.
Ungerstedt, "Epigenetic Modifiers in Myeloid Malignancies: The Role of Histone Deacetylase Inhibitors," Int J Mol Sci., 2018, 19:3091, 18 pages.
Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.
Wakefield, Basil "Fluorinated Pharmaceuticals" Innovations in Pharmaceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).
Waldmann and Schneider, "Targeting histone modifications—epigenetics in cancer," Curr Opin Cell Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.
Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.
Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Xu et al., "Design, synthesis and biological evaluation of deuterated nintedanib for improving pharmacokinetic properties," J. Label Compd. Radiopharm, May 26, 2015, 58:308-312.
Yang et al., "Reversible methylation of promoter-bound STAT3 by histone-modifying enzymes," Proc Natl Acad Sci USA, Dec. 2010, 107(50): 21499-504.
Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yuan et al., "6-Thioguanine Reactivates Epigenetically Silenced Genes in Acute Lymphoblastic Leukemia Cells by Facilitating Proteasome-Mediated Degradation of DNMT1," Cancer Res., Jan. 14, 2011, 71:1904-1911.
Yu et al., "Energetic factos determining the binding of type I inhibitors to c-Met kinase: experimental studies and quantum mechanical calculations," Acta Pharmacologica Sinica, Nov. 2013, 34(11): 1475-1783.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," 2015, 1-40.
Zhu et al., "Preparation of imidazolidin-2-imines and their analogs as aspartyl protease inhibitors for treating various diseases," CA149: 307842 (2008).
Cancer, definition by Medical Dictionary, retrieved from URL<http://medical-dictionary.thefreedictionary.com/Cancer+(disease), p. 1 (2017).
SEER Training Modules, "Cancer Classification," [retrieved Dec. 26, 2005] retrieved from URL<http://training.seer.cancer.gov/module_...ase/unit3_categories2_by_histology.html>, p. 1-3 (2005).
Beta Thalasemia, p. 1-5, Wikipedia (2017).
Pringle "Overview of viruses" Merck Manual (2013).
Simone, Oncology: Introduction, Cecil Textbook of Medicine, 20th Edition, 1996 vol. 1, 1004-1010.
Vardiman, "The World Health Organization (WHO) classification of the myeloid neoplasms," Blood, 2002, 100(7): 2292-2302.
Estey, "New drug approvals in acute myeloid leukaemia: what's the best end point?" Leukemia, 2016, 30: 521-525.
Pui, "Treatment of Acute Lymphoblastic Leukemia," New England Journal of Medicine, 2006, 354: 166-78.
Krishnan, "Multiple myeloma and persistance of drug resistance in the age of novel drugs (Review)," International Journal of Oncology, 2016, 49: 33-50.
Stewart, "Novel therapeutics in multiple myeloma," Hematology, 2012, 17(S1): s105-s108.
Howington, "Treatment of Stage I and II Non-Small Cell Lung Cancer Diagnosis and Management of Lung Cancer 3rd Ed: American College of Chest Physicians Evidence-Based Clinical Practice Guidelines," CHEST 2013, 143(5)(Suppl): e278S-e313S.
Socinski, "Treatment of Stave IV Non-small Cell Lung Cancer Diagnosis and Management of Lung Cancer, 3rd ed: American College of Chest Physicians Evidence-Based Clinical Practice Guideline," CHEST 2013, 143(5)(Suppl): e341S-e368S.
Sanz-Garcia, "Current and advancing treatments for metastatic colorectal cancer," Expert Opinion on Biological Therapy, 2016, 16:1, 93-110.
Boniface, "Multidisciplinary management for esophageal and gastric cancer," Cancer Management and Research, 2016, 39-44.
Yoo, "New drugs in prostate cancer," Prostate Int., 2016, 4: 37-42.
Jett, "Treatment of Small Cell Lung Cancer Diagnosis and Management of Lung Cancer, 3rd ed: American College of Chest Physicians Evidence-Based Clinical Practice Guidelines," CHEST 2013, 143(5)(Suppl): e400S-e419S.
Fattaneh and Devilee, "World Health Organization Classification of Tumours: Pathology and Genetics of Tumours of the Breast and Female Genital Organs," Online http://www.iarc.fr/en/publications/pdfs-online/pat-gen/bb4/BB4.pdf, accessed Nov. 4, 2016 IARCPress Lyon, 2003.
Hudis, "Triple-Negative Breast Cancer: An Unmet Medical Need," The Oncologist, 2011, 16(suppl 1): 1-11.
Gerratana, "Do platinum salts fit all triple negative breast cancers?" Cancer Treatment Reviews, 2016, 48: 34-41.
Gyawali, "Chemotherapy in locally advanced head and neck squamou scell carcinoma," Cancer Treatment Reviews, 2016, 44: 10-16.
Damia, "Contemporary pre-clinical development of anticancer agents—What are the optimal preclinical models?" European Journal of Cancer, 2009, 45: 2768-2781.
Sharma, "Cell-line based platforms to evaluate the therapeutic efficacy of candidate anticancer agents," Nature Reviews Cancer, Apr. 2010, 10: 241-253.
Ocana, "Preclinical development of molecular targeted agents for cancer," Nat. Rev. Clin. Oncol., 2011, 8: 200-209.
Ledford, "US cancer institute overhauls cell lines," Nature, Feb. 2016, 530: 391.

(56) References Cited

OTHER PUBLICATIONS

Johnson et al., "Relationships between drug activity in NCI preclinical in vitro and in vivo models and early clinical trials," British Journal of Cancer, 2001, 84: 1424-1431.
Rotili, "Targeting Histone Demethylases: A New Avenue for the Fight Against Cancer," J. Genes & Cancer, 2(6): 663-679.
Lynch, "LSD1 Inhibition: a therapeutic strategy in cancer?" Expert Opinion on Therapeutic Targets, 2012, 16(12): 1239-1249.
Muller and Krausslich, "Antiviral Strategies," Handbook of Experimental Pharmacology, 2009, 189(1): 1-24.
Wada et al., "Overexpression of the shortest isoform of histone demethylase LSD1 primes hematopoietic stem cells for malignant transformation," Blood, Jun. 2015, 125(24): 3731-3746.
WerMuth, The Practice of Medicinal Chemistry, 1998, p. 241-243, 253, 254.
Yatim et al., "NOTCH1 Nuclear Interactome Reveals Key Regulators of Its Transcriptional Activity and Oncogenic Function," Molecular Cell, 2012, 48: 1-14.
Goossens et al., "Oncogenic ZEB2 activation drives sensitivy toward KDM1A inhibition in T-cell acute lymphoblastic leukemia," Blood, Feb. 2017, 129(8): 981-990.
Hu et al., "LSD1-mediated epigenetic modification is required for TAL1 function and hematopoiesis," PNAS, Jun. 2009, 106(25): 10141-10146.
Niebel et al., "Lysine-specific demethylase 1 (LSD1) in hematopoietic and lymhoid neoplasms," Blood, 2014, 124: 151-152.
Australian Examination Report in Australian Application No. 2015217073, dated Aug. 6, 2018, 4 pages.
Australian Examination Report in Australian Application No. 2015217119, dated Jun. 22, 2018, 4 pages.
Chinese Office Action in Chinese Application No. 201580019205 dated May 22, 2018, 14 pages (English Translation).
Chinese Office Action in Chinese Application No. 201580019205.7, dated Mar. 15, 2019, 9 pages (English Translation).
Chinese Office Action in Chinese Application No. 201580021455.9, dated Oct. 17, 2019, 13 pages(English Translation).
Columbian Office Action in Colombian Application No. NC2016/0001337, dated Jan. 9, 2019, 8 pages(English Translation).
Colombian Office Action in Colombian Application No. NC2016/0001337, dated Jul. 10, 2018, 8 pages(English Translation).
Colombian Office Action in Colombian Application No. NC2017/0011216, dated May 3, 2019, 9 pages(English Translation).
Chilean Opposition in Chilean Application No. 3040-2017, dated Sep. 25, 2019, 20 pages(English Translation).
Ecuador Opposition in Ecuador Application No. IEPI-2018-18869, dated Feb. 8, 2019, 34 pages (English Translation).
Eurasian Office Action in Eurasian Application No. 201691620, dated Jan. 18, 2019, 4 pages(English Translation).
Eurasian Office Action in Eurasian Application No. 201892395, dated Oct. 28, 2019, 12 pages(English Translation).
Indian Office Action in Indian Application No. 201627028454, dated Jun. 26, 2019, 6 pages.
Taiwanese Office Action in Taiwan Application No. 104104830, dated Jul. 30, 2018, 8 pages (English Search Report).
Taiwanese Office Action in Taiwan Application No. 104104827, dated Dec. 18, 2018 11 pages (English Translation).
Japanese Office Action in Japanese Application No. 2016-551815, dated Oct. 2, 2018, 6 pages(English Translation).
Japanese Office Action in Japanese Application No. 2016-551710, dated Oct. 2, 2018, 7 pages(English Translation).
Taiwan Office Action in Taiwan Application No. 104122393, dated May 3, 2019, 6 pages (English Translation).
Ukrainian Office Action in Ukraine Application No. a 2016 09399, dated Sep. 26, 2019, 6 pages (English Translation).
Chilean Office Action in Chilean Application No. 2991-2018, dated Oct. 11, 2019, 15 pages (English Translation).
New Zealand Office Action in New Zealand Application No. 723203, dated Jan. 15, 2020, 4 pages.
Israeli Office Action in Israeli Application No. 257,290, dated May 17, 2020, 11 pages.

\* cited by examiner

SALTS OF AN LSD1 INHIBITOR

FIELD OF THE INVENTION

This application relates to tosylate salts of a lysine specific demethylase-1 (LSD1) inhibitor, including methods of preparation thereof, and intermediates in the preparation thereof, which are useful in the treatment of LSD1 mediated diseases such as cancer.

BACKGROUND OF THE INVENTION

Overexpression of lysine specific demethylase-1 (LSD1) is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Overexpression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6 (1): p. 75; Sareddy, G. R., et al., *KDM1 is a novel therapeutic target for the treatment of gliomas*. Oncotarget, 2013. 4 (1): p. 18-28; Ding, J., et al., *LSD1-mediated epigenetic modification contributes to proliferation and metastasis of colon cancer*. Br J Cancer, 2013. 109 (4): p. 994-1003; Bennani-Baiti, I. M., et al., *Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma*. Hum Pathol, 2012. 43 (8): p. 1300-7; Schulte, J. H., et al., *Lysine-specific demethylase 1 is strongly expressed in poorly differentiated neuroblastoma: implications for therapy*. Cancer Res, 2009. 69 (5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70 (8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54 (3): p. 499-503.

Inhibitors of LSD1 are currently being developed for the treatment of cancer. For example, the molecule 1-{[4-(methoxymethyl)-4-({[(1R,2S)-2-phenylcyclopropyl]amino}methyl)piperidin-1-yl]methyl}cyclobutanecarboxylic acid and other small molecule inhibitors of LSD1 are reported in e.g., US Publication Nos.: 2015-0225394, 2015-0225375, 2015-0225401, 2015-0225379, 2016-0009720, 2016-0009711, 2016-0009712, and 2016-0009721. Accordingly, there is a need in the art for new forms of LSD1-inhibiting molecules for preparing pharmaceutically useful formulations and dosage forms with suitable properties related to, for example, facilitating the manufacture of safe, effective, and high quality drug products.

SUMMARY OF THE INVENTION

In one aspect, provided herein are p-toluenesulfonic acid salts of 1-{[4-(methoxymethyl)-4-({[(1R,2S)-2-phenylcyclopropyl]amino}methyl)piperidin-1-yl]methyl}cyclobutanecarboxylic acid, or hydrates or solvates thereof. In some embodiments, provided herein is a crystalline di-tosylate salt of 1-{[4-(methoxymethyl)-4-({[(1R,2S)-2-phenylcyclopropyl]amino}methyl)piperidin-1-yl]methyl}cyclobutanecarboxylic acid.

In another aspect, provided herein is a pharmaceutical composition, which includes the p-toluenesulfonic acid salt of 1-{[4-(methoxymethyl)-4-({[(1R,2S)-2-phenylcyclopropyl]amino}methyl)piperidin-1-yl]methyl}cyclobutanecarboxylic acid.

In another aspect, provided herein is a method of inhibiting LSD1 using the salts and crystalline forms as described herein.

In another aspect, provided herein are therapeutic methods of using the salts and crystalline forms as described herein.

In another aspect, provided herein are processes for preparing the salts and crystalline forms as described herein.

In another aspect, provided herein are intermediates useful for the preparation of the salts and crystalline forms described herein.

DETAILED DESCRIPTION

General

Figure 1:
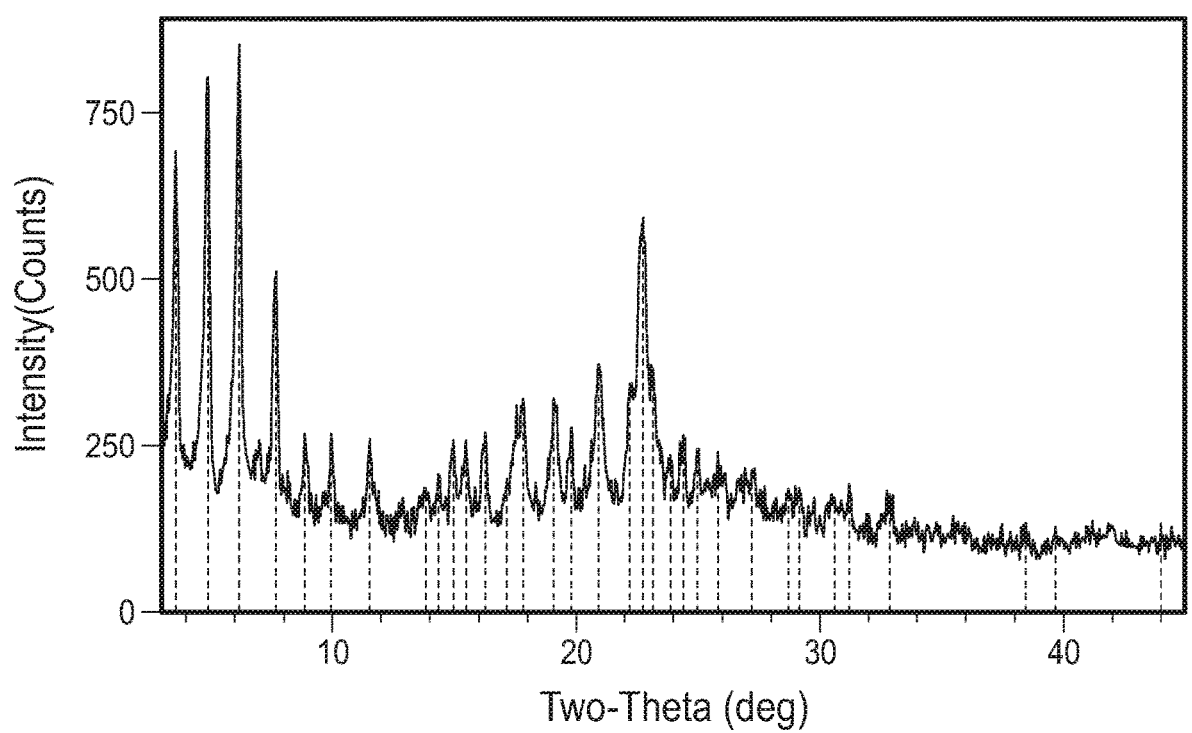
FIG. 1 shows an X-ray powder diffraction (XRPD) pattern of Compound I di-tosylate salt, Form I.

The present disclosure relates to acid salts of an LSD1 inhibitor and crystalline forms thereof. Specifically, provided herein are p-toluenesulfonic acid (tosylic acid) salts of an LSD1 inhibitor and crystalline forms thereof. The salts and crystalline forms described herein have many advantages, for example they have desirable properties, such as ease of handling, ease of processing, storage stability, and ease of purification. Moreover, the salts and crystalline forms can be useful for improving the performance characteristics of a pharmaceutical product such as dissolution profile, shelf-life and bioavailability.

Definition

As used herein, the term "$C_{i\text{-}j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i\text{-}j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, the term "halo" or "halogen" employed alone or in combination with other terms, refers to a halogen atom selected from F, Cl, I or Br. In some embodiments, "halo" or "halogen" refers to a halogen atom selected from F, Cl, or Br. In some embodiments, the halo substituent is Cl or Br. In some embodiments, the halo substituent is Cl.

As used herein, the term "$C_{i\text{-}j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, "$C_{i\text{-}j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms. In some embodiments, the haloalkoxy group is $C_{1\text{-}4}$ haloalkoxy.

As used herein, "protecting group" refers to a grouping of atoms that when attached to a reactive group in a molecule masks, reduces or prevents that reactivity. Examples of protecting groups can be found in T. W. Greene and P. G. Wuts, Protective Groups in Organic Synthesis, (Wiley, 4th ed. 2006), Beaucage and Iyer, Tetrahedron 48:2223-2311 (1992), and Harrison and Harrison et al, Compendium of Synthetic Organic Methods, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2=CHCH_2$—, and the like, groups of the formula —C(O)R', wherein R' is, for example, methyl, phenyl, trifluoromethyl, and the like, groups of the formula —$SO_2R"$, wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethyl silylethoxymethyl, t-butyldimethylsilyl, triisopropylsilyl, and the like. Carboxyl protecting group include moieties that are capable of forming esters with the carboxyl. For example, carboxyl protecting groups and carboxyl can form substituted methyl esters, 2-substituted ethyl esters, 2,6-dialkylphenylesters, silyl esters, substituted benzylesters, and the like. Representative carboxyl protecting groups include benzyl, 9-fluorenylmethyl, methoxymethyl, t-butyl, 2,2,2-trichloroethyl, 2-(trimethylsilyl)ethyl, tetrahydropyranyl, benzoxymethyl, pentafluorophenyl, triphenylmethyl, diphenylmethyl, nitrobenzyl, trimethylsilyl, triethylsilyl, t-butyldimethylsilyl, and the like.

As used herein, TsOH refers to p-toluenesulfonic acid, 4-methylbenzenesulfonic acid, or tosylic acid.

As used herein, and unless otherwise specified, the term "about", when used in connection with a numeric value or range of values which is provided to describe a particular salt or solid form, e.g., a specific temperature or temperature range, such as, for example, that describing a melting, dehydration, or glass transition; a mass change, such as, for example, a mass change as a function of temperature or humidity; a solvent or water content, in terms of, for example, mass or a percentage; or a peak position, such as, for example, in analysis by, for example, $^{13}C$ NMR, DSC, TGA and XRPD; indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.3 degrees 2-theta or +/−0.2 degrees 2-theta.

As used herein, the term "peak" or "characteristic peak" refers to a reflection having a relative height/intensity of at least about 3% of the maximum peak height/intensity. As used herein, the term "crystalline" or "crystalline form" refers to a crystalline solid form of a chemical compound, including, but not limited to, a single-component or multiple-component crystal form, e.g., including solvates, hydrates, clathrates, and a co-crystals. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as a salt of the invention, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) or about 0.3° (2-theta), and the term "substantially" as used in the context of XRPD herein is meant to encompass the above-mentioned variations.

In the same way, temperature readings in connection with DSC, TGA, or other thermal experiments can vary about +3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not substantially crystalline as determined, for instance, by XRPD or where the substance, component, or product in question, for example is not birefringent when viewed microscopically. In certain embodiments, a sample comprising an amorphous form of a substance may be substantially free of other amorphous forms and/or crystalline forms. For example, an amorphous substance can be identified by an XRPD spectrum having an absence of reflections.

In some embodiments, the salts (or hydrates and solvates thereof) of the invention are prepared in batches referred to as batches, samples, or preparations. The batches, samples, or preparations can include the salts of the invention in any of the crystalline or non-crystalline forms described herein, included hydrated and non-hydrated forms, and mixtures thereof.

The term "hydrate," as used herein, is meant to refer to a solid form of Compound I di-tosylate salt that includes water. The water in a hydrate can be present in a stoichiometric amount with respect to the amount of salt in the solid, or can be present in varying amounts, such as can be found in connection with channel hydrates.

As used herein, the term "crystalline purity," means percentage of a crystalline form in a preparation or sample which may contain other forms such as an amorphous form of the same compound, or at least one other crystalline form of the compound, or mixtures thereof.

As used herein, the term "substantially crystalline," means a majority of the weight of a sample or preparation of a salt (or hydrate or solvate thereof) of the invention is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

As used herein, the term "contacting" refers to the bringing together of indicated moieties in an in vitro system or an in vivo system. For example, "contacting" a LSD1 enzyme with a compound of the invention includes the administration of a compound of the present invention to an individual or patient, such as a human, having a LSD1 enzyme, as well as, for example, introducing a compound of the invention into a sample containing a cellular or purified preparation containing the LSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents, wherein one or more equivalents of second reagent are used with respect to the first reagent. In some embodiments, the reacting step of a synthetic process may involve one or more substances in addition to the reagents such as solvent and/or a catalyst. The reacting steps of the processes described herein can be conducted for a time and under conditions suitable for preparing the identified product.

As used herein, the terms "combining" and "mixing" with respect to reagents of a chemical reaction are used interchangeably with the term "reacting" herein. The term "coupling" also can be considered interchangeable with "reacting" but may be used in conjunction with a reaction step that involves the linking of two organic fragments.

p-Toluenesulfonic Acid Salt

In one aspect, the present disclosure provides p-toluene sulfonic acid (or tosylic acid) salts of 1-{[4-(methoxymethyl)-4-({[(1R,2S)-2-phenylcyclopropyl]amino}methyl)piperidin-1-yl]methyl}cyclobutanecarboxylic acid, or hydrates or solvates thereof. Compound I refers to 1-{[4-(methoxymethyl)-4-({[(1R,2S)-2-phenylcyclopropyl]amino}methyl)piperidin-1-yl]methyl)}cyclobutanecarboxylic acid having the formula:

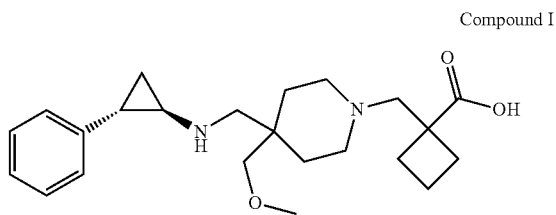 [SMILES: COCC1(CN[C@@H]2C[C@H]2c2ccccc2)CCN(CC2(C(=O)O)CCC2)CC1]

Compound I

In some embodiments, the present disclosure provides 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate), which is shown below and referred to herein as "Compound I di-tosylate salt," "Compound I bis-p-toluenesulfonic acid," "Compound I bis-p-toluenesulfonic acid salt," "Compound I di-p-toluenesulfonic acid," "Compound I di-p-toluenesulfonic acid salt," "Compound I bis(4-methylbenzenesulfonate)," or 1-{[4-(methoxymethyl)-4-({[(1R,2S)-2-phenylcyclopropyl]amino}methyl)piperidin-1-yl]methyl}cyclobutanecarboxylic acid di-tosylate salt.

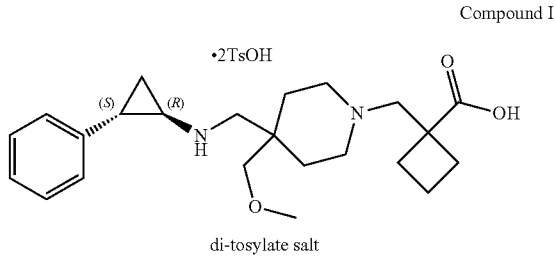

Compound I di-tosylate salt

It will be understood that a tosylate salt of 1-{[4-(methoxymethyl)-4-({[(1R,2S)-2-phenylcyclopropyl]amino}methyl)piperidin-1-yl]methyl}cyclobutanecarboxylic acid comprises a cation of 1-{[4-(methoxymethyl)-4-({[(1R,2S)-2-phenylcyclopropyl]amino}methyl)piperidin-1-yl]methyl}cyclobutanecarboxylic acid (e.g., in one embodiment, protonated at one atomic position, or in other embodiments, protonated at more than one atomic position) and at least one anion of p-toluenesulfonic acid, where the anion is referred to herein as "tosylate" according to convention. In certain embodiments, solid forms of 1-{[4-(methoxymethyl)-4-({[(1R,2S)-2-phenylcyclopropyl]amino}methyl)piperidin-1-yl]methyl}cyclobutanecarboxylic acid tosylate salt will comprise 1-{[4-(methoxymethyl)-4-({[(1R,2S)-2-phenylcyclopropyl]amino}methyl)piperidin-1-yl]methyl}cyclobutanecarboxylic acid and p-toluenesulfonic acid with a molar ratio of about 1:1. In certain embodiments, solid forms of 1-{[4-(methoxymethyl)-4-({[(1R,2 S)-2-phenylcyclopropyl]amino}methyl)piperidin-1-yl]methyl}) cyclobutanecarboxylic acid di-tosylate salt comprise 1-{[4-(methoxymethyl)-4-({[(1R,2 S)-2-phenylcyclopropyl]amino}methyl)piperidin-1-yl]methyl}cyclobutanecarboxylic acid and p-toluenesulfonic acid with a molar ratio of 1:2.

In one embodiment, the molar ratio of Compound I to p-toluenesulfonic acid in the salt is about 1:2. In another embodiment, the molar ratio of Compound I to p-toluenesulfonic acid in the salt is about 1:1. In another embodiment, the molar ratio of Compound I to p-toluenesulfonic acid in the salt is about 1:1.5. In another embodiment, the molar ratio of Compound I to p-toluenesulfonic acid in the salt is about 1:0.5. In another embodiment, the molar ratio of Compound I to p-toluenesulfonic acid in the salt is about 1:2.5. In another embodiment, the molar ratio of Compound I to p-toluenesulfonic acid in the salt is between about 1:0.5 and about 1:2.

In some embodiments, the p-toluenesulfonic acid salt of Compound I is a hydrate. In some embodiments, the p-toluenesulfonic acid salt of Compound I is an anhydrate. In some embodiments, the p-toluenesulfonic acid salt of Compound I is mono-hydrate (e.g., the molar ratio of the salt to water is about 1:1). In some embodiments, the p-toluenesulfonic acid salt of Compound I is a di-hydrate (e.g., the molar ratio of the salt to water is about 1:2). In some embodiments, the p-toluenesulfonic acid salt of Compound I is a hemi-hydrate (e.g., the molar ratio of the salt to water is about 2:1). In some embodiments, the p-toluenesulfonic acid salt of Compound I has one or more molecules of water per molecule of salt.

The tosylate salts of Compound I are LSD1 inhibitors useful in the treatment of diseases. The advantages of the tosylic acid salt of Compound I include high crystallinity, high melting point, stable crystalline form, and non-hygroscopic properties, each of which facilitates the purification, reproducibility, scale up, manufacturing, and formulation of the drug compound.

Compound I p-toluenesulfonic acid salt can be prepared as an amorphous solid, as a crystalline solid, or as a mixture thereof. In some embodiments, Compound I p-toluenesulfonic acid salt is a di-tosylate salt. In some embodiments, Compound I di-tosylate salt is substantially crystalline. In certain embodiments, Compound I di-tosylate salt has a crystalline purity of at least about 90%, 91%, 92%, 93%, 94%, 95%, 96%, 97%, 98% or 99%. In some embodiments, Compound I di-tosylate salt is crystalline with a crystalline purity of about 100%.

Form I of Compound I Di-Tosylate Salt

In some embodiments, the crystalline solid has Form I, which is described below in the Examples. In some embodiments, Form I has at least one characteristic XRPD peak, in terms of 2-theta, at about 3.6 (e.g., 3.6±0.3 or 3.6±0.2) degrees. In some embodiments, Form I has at least one characteristic XRPD peak, in terms of 2-theta, at about 4.9 (e.g., 4.9±0.3 or 4.9±0.2) degrees. In some embodiments, Form I has at least one characteristic XRPD peak, in terms of 2-theta, at about 6.2 (e.g., 6.2±0.3 or 6.2±0.2) degrees. In some embodiments, Form I has at least one characteristic XRPD peak, in terms of 2-theta, at about 7.7 (e.g., 7.7±0.3 or 7.7±0.2) degrees. In some embodiments, Form I has at least one characteristic XRPD peak, in terms of 2-theta, at about 22.7 (e.g., 22.7±0.3 or 22.7±0.2) degrees. In some embodiments, Form I has at least one characteristic XRPD peak, in terms of 2-theta, at about 4.9 (e.g., 4.9±0.3 or 4.9±0.2) or about 6.2 (e.g., 6.2±0.3 or 6.2±0.2) degrees. In some embodiments, Form I has at least one characteristic XRPD peak, in terms of 2-theta, at about 3.6 (e.g., 3.6±0.3 or 3.6±0.2), about 4.9 (e.g., 4.9±0.3 or 4.9±0.2), or about 6.2 (e.g., 6.2±0.3 or 6.2±0.2) degrees. In some embodiments, Form I has two or more characteristic XRPD peaks, in terms of 2-theta, selected from about 3.6 (e.g., 3.6±0.3 or 3.6±0.2), about 4.9 (e.g., 4.9±0.3 or 4.9±0.2), about 6.2 (e.g., 6.2±0.3 or 6.2±0.2), about 7.7 (e.g., 7.7±0.3 or 7.7±0.2) and about 22.7 (e.g., 22.7±0.3 or 22.7±0.2) degrees. In some embodiments, Form I has two or more characteristic XRPD peaks, in terms of 2-theta, selected from at about 3.6 (e.g., 3.6±0.3 or 3.6±0.2), about 4.9 (e.g., 4.9±0.3 or 4.9±0.2), about 6.2 (6.2±0.3 or 6.2±0.2), about 7.7 (e.g., 7.7±0.3 or 7.7±0.2), about 22.7 (e.g., 22.7±0.3 or 22.7±0.2), about 8.9 (e.g., 8.9±0.3 or 8.9±0.2), about 10.0 (e.g., 10.0±0.3 or 10.0±0.2), about 11.5 (e.g., 11.5±0.3 or 11.5±0.2), about 14.3 (e.g., 14.3±0.3 or 14.3±0.2), about 15.0 (e.g., 15.0±0.3 or 15.0±0.2), about 15.5 (e.g., 15.5±0.3 or 15.5±0.2), about 16.3 (e.g., 16.3±0.3 or 16.3±0.2), about 17.8 (e.g., 17.8±0.3 or 17.8±0.2), about 19.1 (e.g., 19.1±0.3 or 19.1±0.2), about 19.8 (e.g., 19.8±0.3 or 19.8±0.2), about 20.9 (e.g., 20.9±0.3 or 20.9±0.2), and about 22.2 (e.g., 22.2±0.3 or 22.2±0.2) degrees. In some embodiments, Form I has three or more characteristic XRPD peaks, in terms of 2-theta, selected from about 3.6 (e.g., 3.6±0.3 or 3.6±0.2), about 4.9 (e.g., 4.9±0.3 or 4.9±0.2), about 6.2 (6.2±0.3 or 6.2±0.2), about 7.7 (e.g., 7.7±0.3 or 7.7±0.2), about 22.7 (e.g., 22.7±0.3 or 22.7±0.2), about 8.9 (e.g., 8.9±0.3 or 8.9±0.2), about 10.0 (e.g., 10.0±0.3 or 10.0±0.2), about 11.5 (e.g., 11.5±0.3 or 11.5±0.2), about 14.3 (e.g., 14.3±0.3 or 14.3±0.2), about 15.0 (e.g., 15.0±0.3 or 15.0±0.2), about 15.5 (e.g., 15.5±0.3 or 15.5±0.2), about 16.3 (e.g., 16.3±0.3 or 16.3±0.2), about 17.8 (e.g., 17.8±0.3 or 17.8±0.2), about 19.1 (e.g., 19.1±0.3 or 19.1±0.2), about 19.8 (e.g., 19.8±0.3 or 19.8±0.2), about 20.9 (e.g., 20.9±0.3 or 20.9±0.2), and about 22.2 (e.g., 22.2±0.3 or 22.2±0.2) degrees. In some embodiments, Form I has four or more characteristic XRPD peaks, in terms of 2-theta, selected from about 3.6 (e.g., 3.6±0.3 or 3.6±0.2), about 4.9 (e.g., 4.9±0.3 or 4.9±0.2), about 6.2 (6.2±0.3 or 6.2±0.2), about 7.7 (e.g., 7.7±0.3 or 7.7±0.2), about 22.7 (e.g., 22.7±0.3 or 22.7±0.2), about 8.9 (e.g., 8.9±0.3 or 8.9±0.2), about 10.0 (e.g., 10.0±0.3 or 10.0±0.2), about 11.5 (e.g., 11.5±0.3 or 11.5±0.2), about 14.3 (e.g., 14.3±0.3 or 14.3±0.2), about 15.0 (e.g., 15.0±0.3 or 15.0±0.2), about 15.5 (e.g., 15.5±0.3 or 15.5±0.2), about 16.3 (e.g., 16.3±0.3 or 16.3±0.2), about 17.8 (e.g., 17.8±0.3 or 17.8±0.2), about 19.1 (e.g., 19.1±0.3 or 19.1±0.2), about 19.8 (e.g., 19.8±0.3 or 19.8±0.2), about 20.9 (e.g., 20.9±0.3 or 20.9±0.2), and about 22.2 (e.g., 22.2±0.3 or 22.2±0.2) degrees. In some embodiments, Form I has an X-ray powder diffraction pattern comprising one or more characteristic peaks selected from about 3.6 (e.g., 3.6±0.3 or 3.6±0.2), about 4.9 (e.g., 4.9±0.3 or 4.9±0.2), about 6.2 (6.2±0.3 or 6.2±0.2), about 7.7 (e.g., 7.7±0.3 or 7.7±0.2), about 22.7 (e.g., 22.7±0.3 or 22.7±0.2), about 8.9 (e.g., 8.9±0.3 or 8.9±0.2), about 10.0 (e.g., 10.0±0.3 or 10.0±0.2), about 11.5 (e.g., 11.5±0.3 or 11.5±0.2), about 14.3 (e.g., 14.3±0.3 or 14.3±0.2), about 15.0 (e.g., 15.0±0.3 or 15.0±0.2), about 15.5 (e.g., 15.5±0.3 or 15.5±0.2), about 16.3 (e.g., 16.3±0.3 or 16.3±0.2), about 17.8 (e.g., 17.8±0.3 or 17.8±0.2), about 19.1 (e.g., 19.1±0.3 or 19.1±0.2), about 19.8 (e.g., 19.8±0.3 or 19.8±0.2), about 20.9 (e.g., 20.9±0.3 or 20.9±0.2), and about 22.2 (e.g., 22.2±0.3 or 22.2±0.2) degrees 2-theta, and combinations thereof.

In some embodiments, Form I has an XRPD pattern substantially as depicted in FIG. 1.

Figure 2:
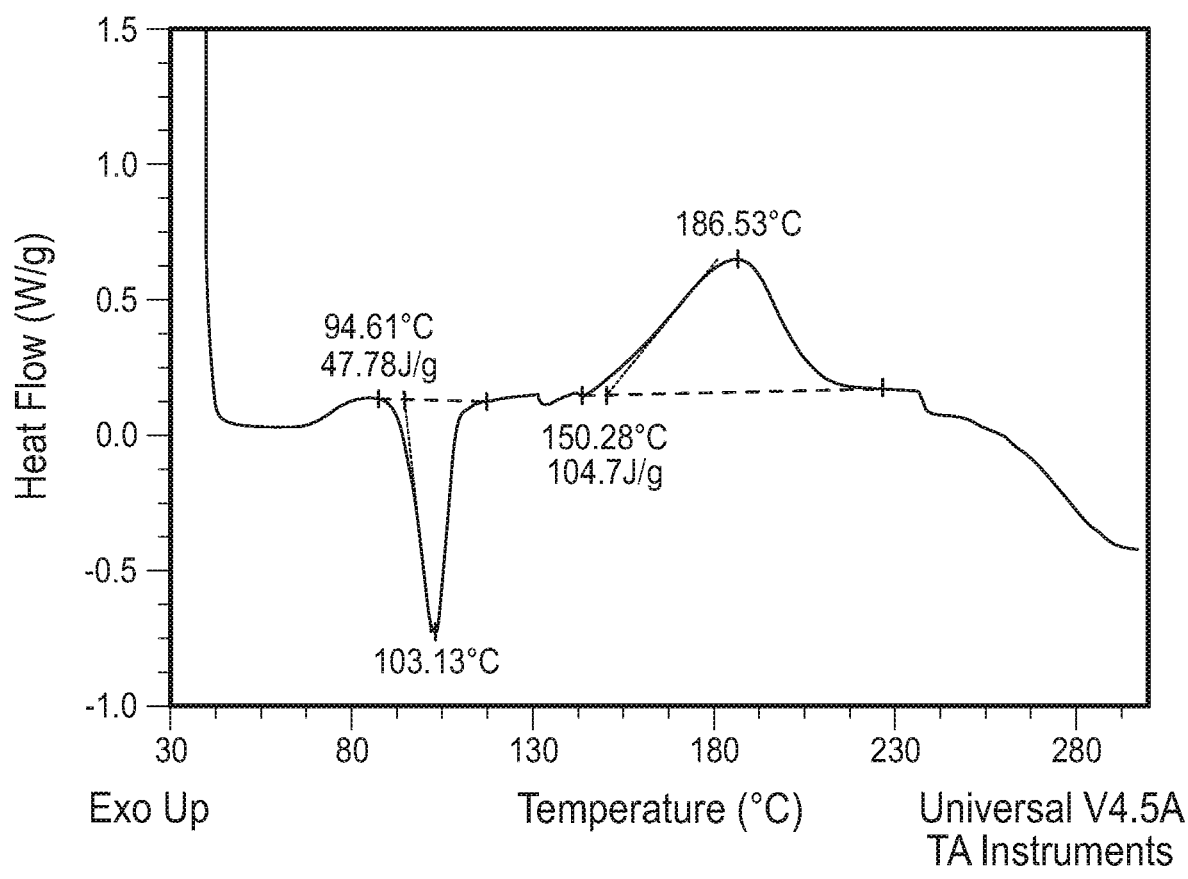
FIG. 2 shows a DSC thermogram of Compound I di-tosylate salt, Form I.
Figure 3:
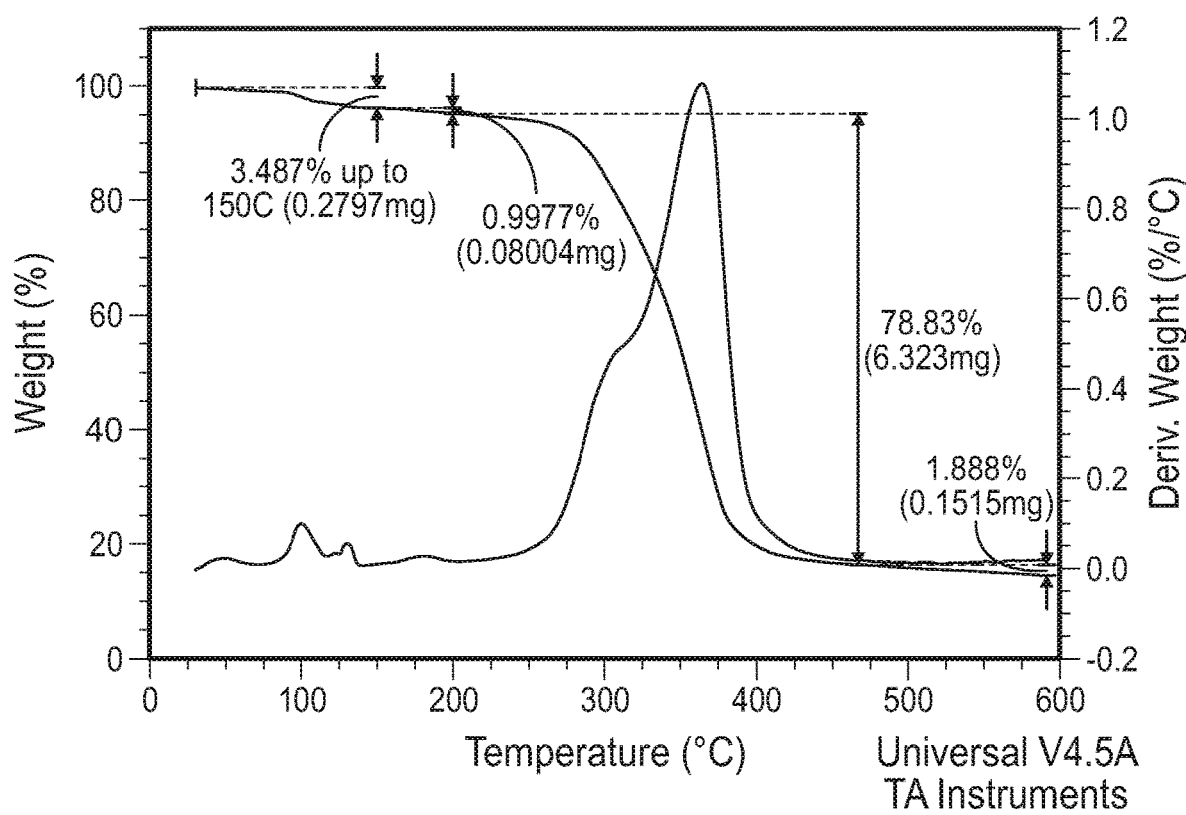
FIG. 3 shows a TGA thermogram of Compound I di-tosylate salt, Form I.

In some embodiments, Form I exhibits a differential scanning calorimetry thermogram having an endotherm with an onset temperature of about 95° C. and a peak temperature of about 103° C. In some embodiments, Form I exhibits a differential scanning calorimetry thermogram having an endotherm with an onset temperature of about 94.6° C. and a peak temperature of about 103.1° C. In some embodiments, Form I has an endothermic peak (e.g., a melting point) at a temperature of about 103° C. In some embodiments, Form I has an exothermic peak at temperature about 187° C. In some embodiments, Form I has a melting point of about 103.1° C. In some embodiments, Form I has a DSC thermogram substantially as depicted in FIG. 2. In some embodiments, Form I has a TGA thermogram substantially as depicted in FIG. 3.

In some embodiments, Form I exhibits a DSC thermogram having an endotherm with an onset temperature of about 95° C., and a peak temperature of about 103° C.; and an X-ray powder diffraction pattern comprising one or more characteristic peaks at about 3.6, about 4.9, about 6.2, about 7.7, or about 22.7 degrees 2-theta. In some embodiments, Form I exhibits a DSC thermogram having an endothermic peak at about 103° C.; and an X-ray powder diffraction pattern comprising one or more characteristic peaks at about 3.6, about 4.9, about 6.2, about 7.7, or about 22.7 degrees 2-theta. In some embodiments, Form I exhibits a differential scanning calorimetry thermogram having an endotherm with an onset temperature of about 94.6° C. and a peak temperature of about 103.1° C.; and an X-ray powder diffraction pattern comprising a characteristic peak at about 3.6 (e.g., 3.6±0.3 or 3.6±0.2), about 4.9 (e.g., 4.9±0.3 or 4.9±0.2), about 6.2 (e.g., 6.2±0.3 or 6.2±0.2), about 7.7 (e.g., 7.7±0.3 or 7.7±0.2) or about 22.7 (e.g., 22.7±0.3 or 22.7±0.2) degrees 2-theta. In some embodiments, Form I exhibits a DSC thermogram having an exothermic peak at about 187° C.; and an X-ray powder diffraction pattern comprising one or more characteristic peaks at about 3.6, about 4.9, about 6.2, about 7.7, or about 22.7 degrees 2-theta.

In some embodiments, Form I has an XRPD pattern substantially as depicted in FIG. 1 and a DSC thermogram substantially as depicted in FIG. 2.

Form HI of Compound I Di-Tosylate Salt

In some embodiments, the present application relates to the crystalline form of Compound I di-tosylate salt referred to as Form HI, which is described below and in the Examples. The experimental evidence shows that Form HI is a hydrated form of Compound I di-tosylate salt.

In some embodiments, Form HI has an XRPD pattern comprising a characteristic peak, in terms of 2-theta, at about 7.0 degrees. In some embodiments, Form HI has an XRPD pattern comprising a characteristic peak, in terms of 2-theta, at about 10.4 degrees. In some embodiments, Form HI has an XRPD pattern comprising a characteristic peak, in terms of 2-theta, at about 13.6 degrees. In some embodiments, Form HI has an XRPD pattern comprising a characteristic peak, in terms of 2-theta, at about 15.5 degrees. In some embodiments, Form HI has an XRPD pattern comprising a characteristic peak, in terms of 2-theta, at about 17.3 degrees. In some embodiments, Form HI has an XRPD pattern comprising a characteristic peak, in terms of 2-theta, at about 22.2 degrees. In some embodiments, Form HI has an XRPD pattern comprising a characteristic peak, in terms of 2-theta, at about 24.0 degrees.

In some embodiments, Form HI has an XRPD pattern comprising two or more characteristic peaks, in terms of 2-theta, selected from about 7.0, about 10.4, about 13.6, about 15.5, about 17.3, about 22.2, and about 24.0 degrees. In some embodiments, Form HI has an X-ray powder diffraction pattern comprising three or more characteristic peaks, in terms of 2-theta, selected from about 7.0, about 10.4, about 13.6, about 15.5, about 17.3, about 22.2, and about 24.0 degrees.

In some embodiments, Form HI has an XRPD pattern comprising one or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD comprising two or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD pattern comprising three or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

In some embodiments, Form HI has an XRPD pattern comprising four or more characteristic peaks, in terms of 2-theta, selected from about 7.0, about 10.4, about 13.6, about 15.5, about 16.6, about 17.3, about 18.7, about 19.8, about 20.2, about 20.5, about 20.8, about 21.7, about 22.2, about 23.1, about 24.0, and about 28.2 degrees.

Figure 4:
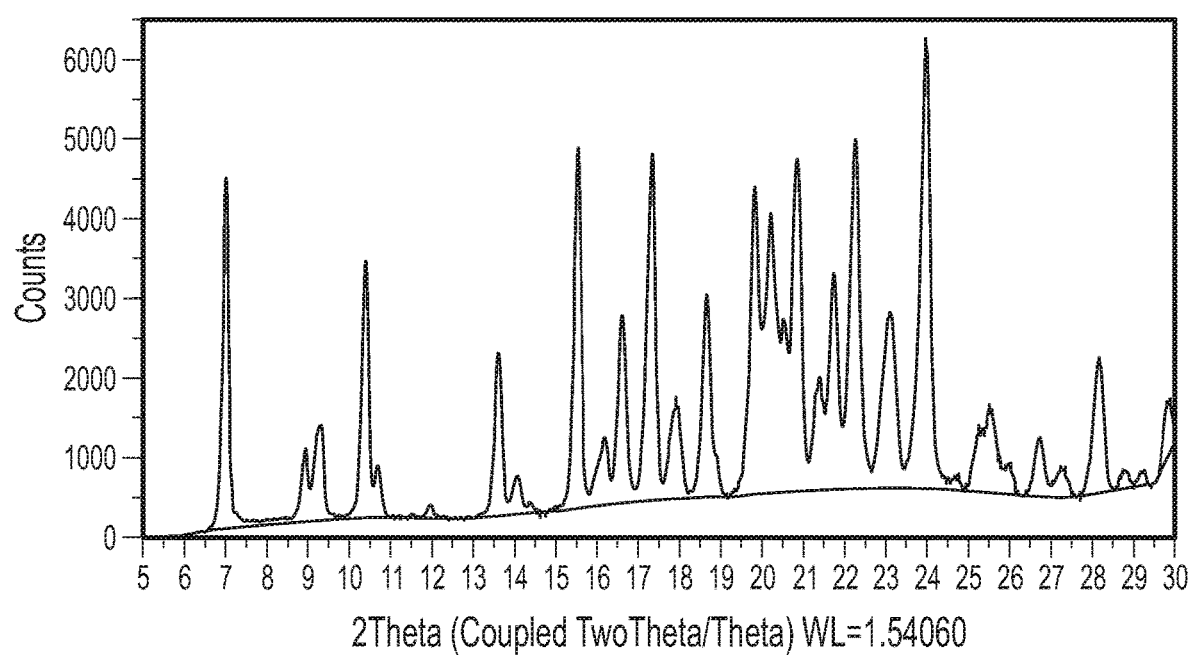
FIG. 4 shows an XRPD pattern of Compound I di-tosylate salt, Form HI.

In some embodiments, Form HI has an XRPD pattern substantially as depicted in FIG. 4.

Figure 5:
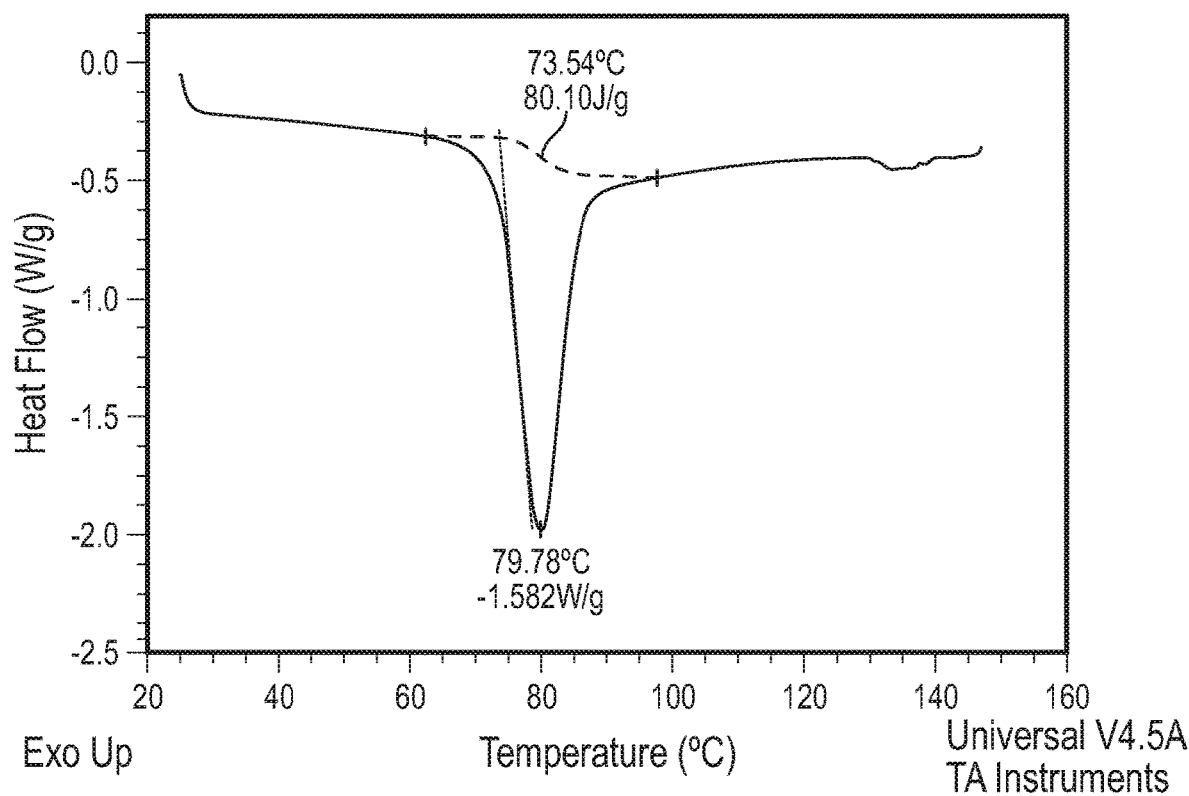
FIG. 5 shows a DSC thermogram of Compound I di-tosylate salt, Form HI.
Figure 6:
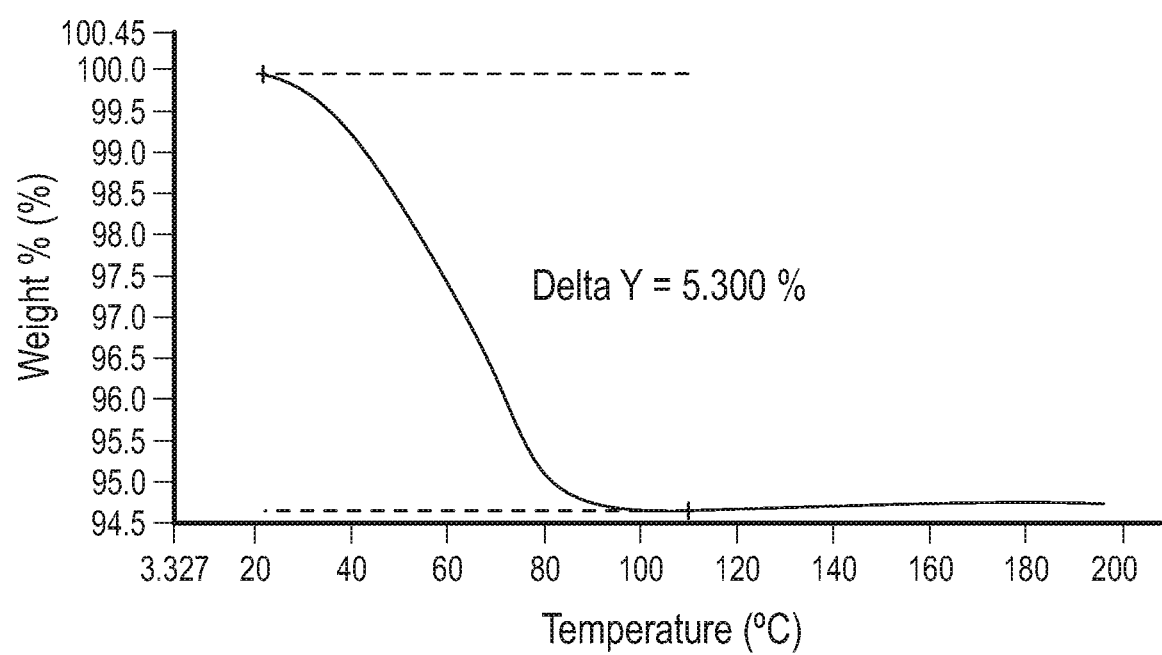
FIG. 6 shows a TGA thermogram of Compound I di-tosylate salt, Form HI.

In some embodiments, Form HI exhibits a differential scanning calorimetry thermogram having an endotherm with an onset temperature of about 74° C. and a peak temperature of about 80° C. In some embodiments, Form HI has an endothermic peak (e.g., a dehydration event) at a temperature of about 80° C. In some embodiments, Form HI has a DSC thermogram substantially as depicted in FIG. 5. In some embodiments, Form HI has a TGA thermogram substantially as depicted in FIG. 6.

In some embodiments, Form HI exhibits a differential scanning calorimetry thermogram having an endothermic peak at a temperature of about 80° C.; and an XRPD pattern comprising a characteristic peak selected from about 7.0, about 15.5, and about 17.3 degrees 2-theta. In some embodiments, Form HI exhibits a differential scanning calorimetry thermogram having an endotherm with an onset temperature of about 74° C. and a peak temperature of about 80° C.; and an XRPD pattern comprising a characteristic peak selected from about 7.0, about 15.5, and about 17.3 degrees 2-theta.

In some embodiments, Form HI exhibits a differential scanning calorimetry thermogram having an endothermic peak at a temperature of about 80° C.; and an XRPD pattern comprising a characteristic peak selected from about 7.0, about 10.4, about 13.6, about 15.5, about 17.3, about 22.2, and about 24.0 degrees. In some embodiments, Form HI exhibits a differential scanning calorimetry thermogram having an endotherm with an onset temperature of about 74° C. and a peak temperature of about 80° C.; and an XRPD pattern comprising a characteristic peak selected from about 7.0, about 10.4, about 13.6, about 15.5, about 17.3, about 22.2, and about 24.0 degrees.

In some embodiments, Form HI has an XRPD pattern substantially as depicted in FIG. 4 and a DSC thermogram substantially as depicted in FIG. 5.

Form HII of Compound I Di-Tosylate Salt

In some embodiments, the present application relates to the crystalline form of Compound I di-tosylate salt referred to as Form HII, which is described below and in the Examples. The experimental evidence shows that Form HII is a hydrated form of Compound I di-tosylate salt.

In some embodiments, Form HII has an XRPD pattern comprising a characteristic peak, in terms of 2-theta, at about 8.7 degrees. In some embodiments, Form HII has an XRPD pattern comprising a characteristic peak, in terms of 2-theta, at about 10.1 degrees. In some embodiments, Form HII has an XRPD pattern comprising a characteristic peak, in terms of 2-theta, at about 14.8 degrees. In some embodiments, Form HII has an XRPD pattern comprising a characteristic peak, in terms of 2-theta, at about 21.3 degrees. In some embodiments, Form HII has an XRPD pattern comprising a characteristic peak, in terms of 2-theta, at about 22.0 degrees. In some embodiments, Form HII has an XRPD pattern comprising a characteristic peak, in terms of 2-theta, at about 22.7 degrees. In some embodiments, Form HII has an XRPD pattern comprising a characteristic peak, in terms of 2-theta, at about 24.3 degrees.

In some embodiments, Form HII has an XRPD pattern comprising two or more characteristic peaks, in terms of 2-theta, selected from about 8.7, about 10.1, about 14.8, about 21.3, about 22.0, about 22.7, and about 24.3 degrees 2-theta.

In some embodiments, Form HII has an XRPD pattern comprising three or more characteristic peaks, in terms of 2-theta, selected from about 8.7, about 10.1, about 14.8, about 21.3, about 22.0, about 22.7, and about 24.3 degrees 2-theta.

Figure 7:
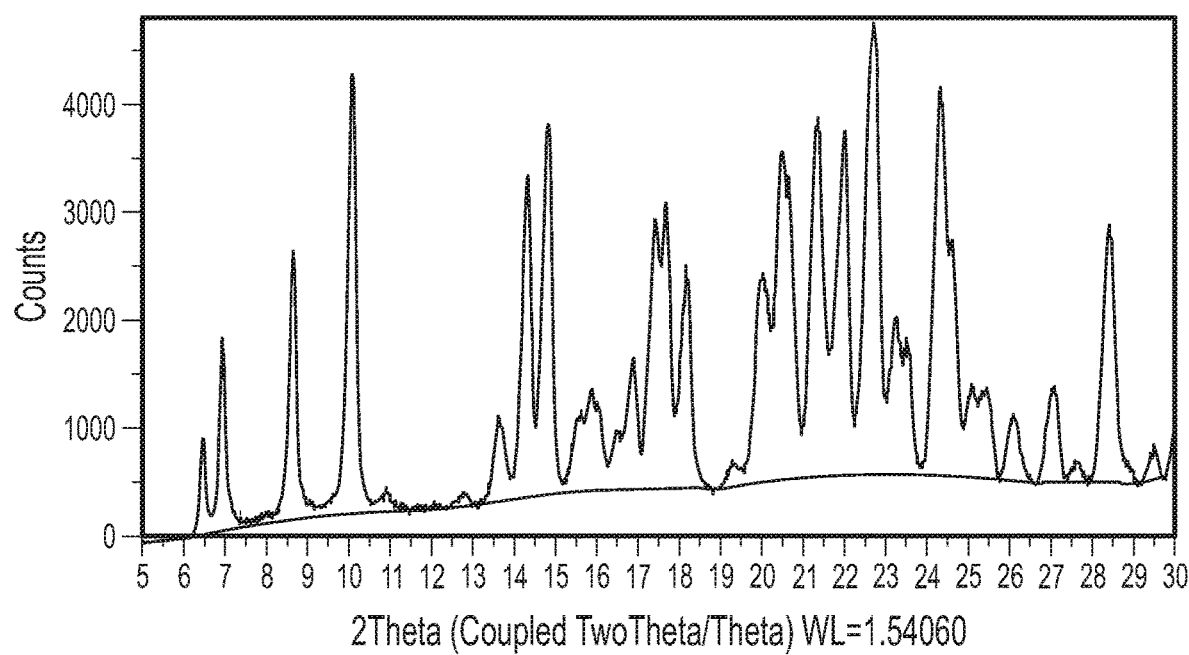
FIG. 7 shows an XRPD pattern of Compound I di-tosylate salt, Form HIII.

In some embodiments, Form HII has an X-ray powder diffraction pattern substantially as shown in FIG. 7.

In some embodiments, Form HII exhibits a differential scanning calorimetry thermogram having an endothermic peak at a temperature of about 52° C. In some embodiments, Form HII has a DSC thermogram substantially as depicted in FIG. 8.

Figure 9:
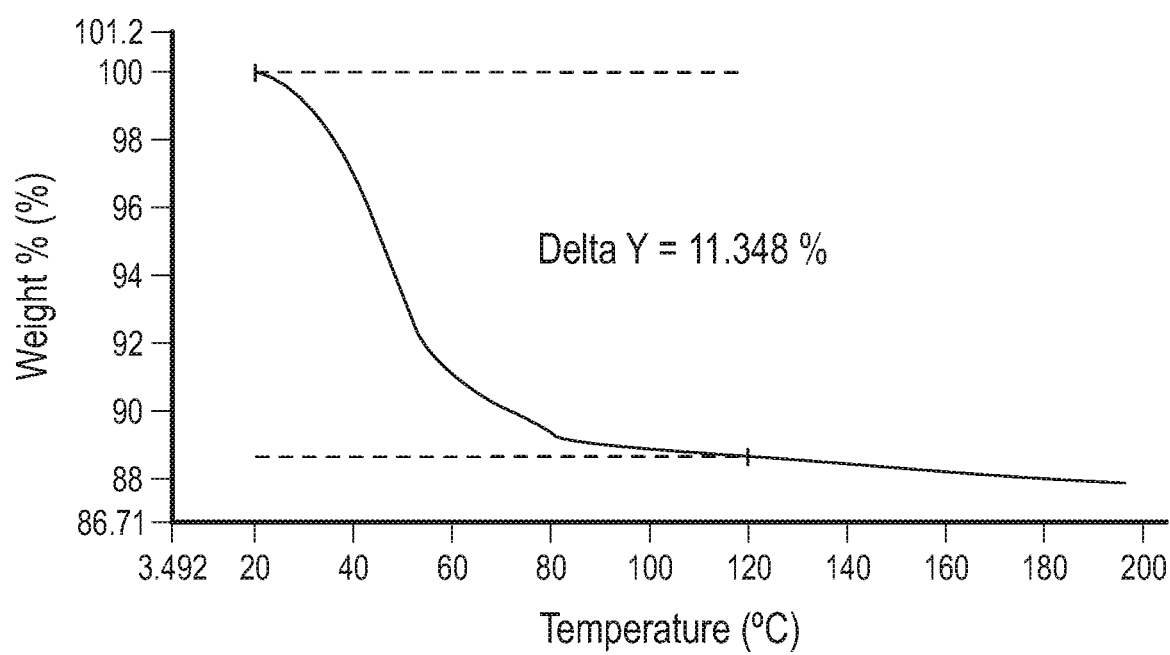
FIG. 9 shows a TGA thermogram of Compound I di-tosylate salt, Form HIII.

In some embodiments, Form HII has a TGA thermogram substantially as depicted in FIG. 9.

In some embodiments, Form HII exhibits a differential scanning calorimetry thermogram having an endothermic peak at a temperature of about 52° C.; and an X-ray powder diffraction pattern comprising a characteristic peak selected from about 8.7, about 10.1, about 14.8, about 21.3, about 22.0, about 22.7, and about 24.3 degrees 2-theta.

Figure 8:
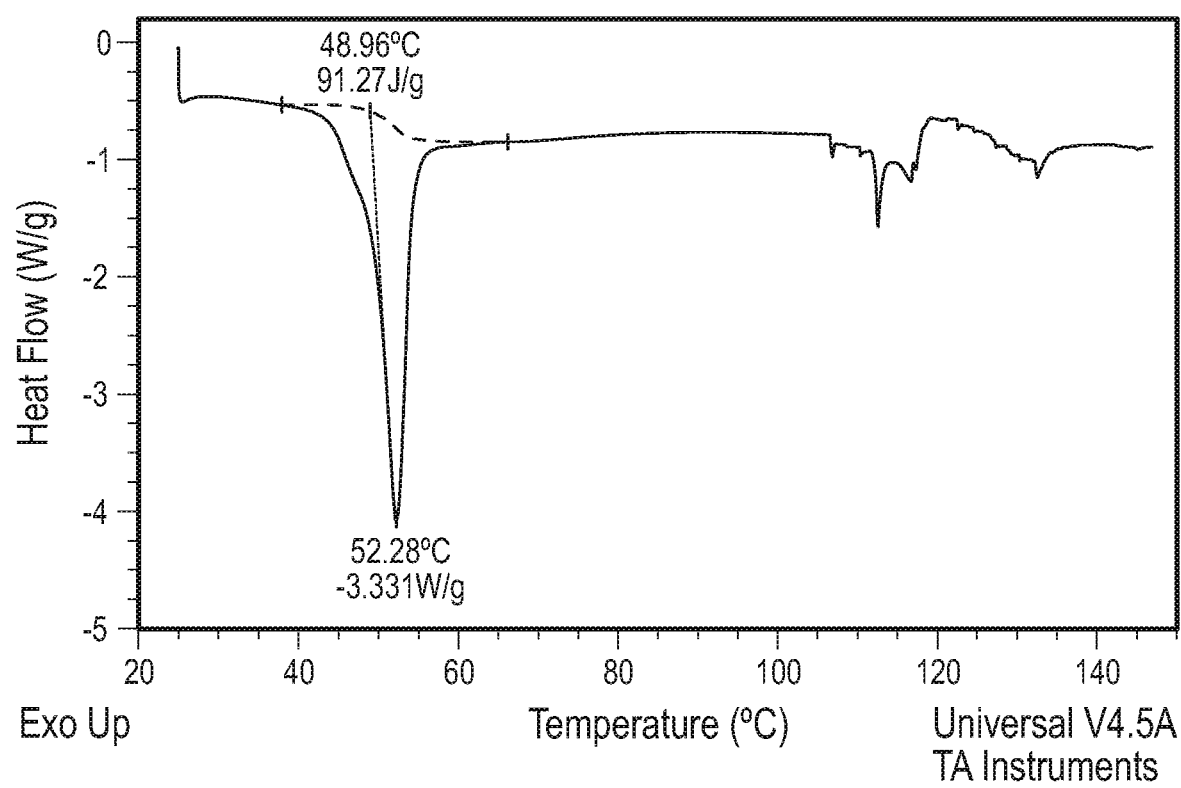
FIG. 8 shows a DSC thermogram of Compound I di-tosylate salt, Form HIII.

In some embodiments, Form HIII has an XRPD pattern substantially as depicted in FIG. 7 and a DSC thermogram substantially as depicted in FIG. 8.

Form HIII of Compound I Di-Tosylate Salt

In some embodiments, the present application relates to the crystalline form of Compound I di-tosylate salt referred to as Form HIII, which is described below and in the Examples. The experimental evidence shows Form HIII is a hydrated form of Compound I di-tosylate salt.

In some embodiments, Form HIII has an XRPD pattern comprising a characteristic peak, in terms of 2-theta, at about 7.0 degrees. In some embodiments, Form HIII has an XRPD pattern comprising a characteristic peak, in terms of 2-theta, at about 9.0 degrees. In some embodiments, Form HIII has an XRPD pattern comprising a characteristic peak, in terms of 2-theta, at about 9.2 degrees. In some embodiments, Form HIII has an XRPD pattern comprising a characteristic peak, in terms of 2-theta, at about 10.2 degrees. In some embodiments, Form HIII has an XRPD pattern comprising a characteristic peak, in terms of 2-theta, at about 17.9 degrees. In some embodiments, Form HIII has an XRPD pattern comprising a characteristic peak, in terms of 2-theta, at about 20.3 degrees. In some embodiments, Form HIII has an XRPD pattern comprising a characteristic peak, in terms of 2-theta, at about 22.0 degrees. In some embodiments, Form HIII has an XRPD pattern comprising a characteristic peak, in terms of 2-theta, at about 23.8 degrees.

In some embodiments, Form HIII has an XRPD pattern comprising two or more characteristic peaks, in terms of 2-theta, selected from about 7.0, about 9.0, about 9.2, about 10.2, about 17.9, about 20.3, about 22.0, and about 23.8 degrees.

In some embodiments, Form HIII has an XRPD pattern comprising three or more characteristic peaks, in terms of 2-theta, selected from about 7.0, about 9.0, about 9.2, about 10.2, about 17.9, about 20.3, about 22.0, and about 23.8 degrees 2-theta.

Figure 10:
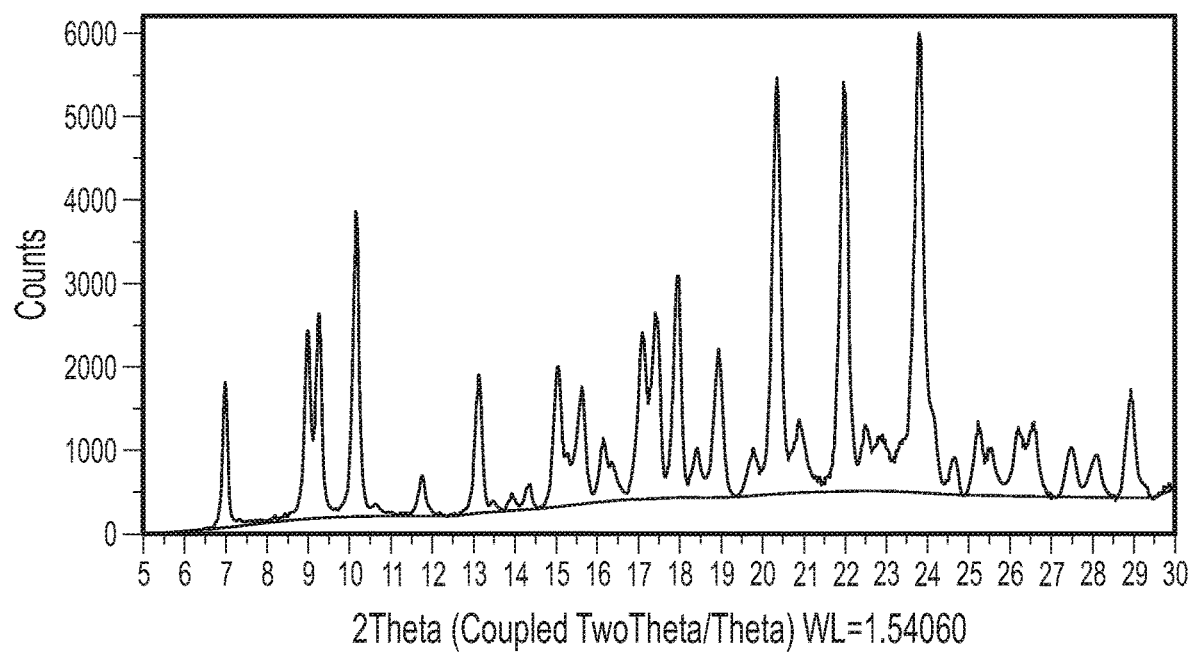
FIG. 10 shows an XRPD pattern of Compound I di-tosylate salt, Form HIII.

In some embodiments, Form HIII has an X-ray powder diffraction pattern substantially as shown in FIG. 10.

In some embodiments, Form HIII exhibits a differential scanning calorimetry thermogram having an endothermic peak at a temperature of about 67° C. In some embodiments, Form HIII further exhibits an endothermic peak at a temperature of about 98° C. In some embodiments, Form HIII has a DSC thermogram substantially as depicted in FIG. 11.

Figure 12:
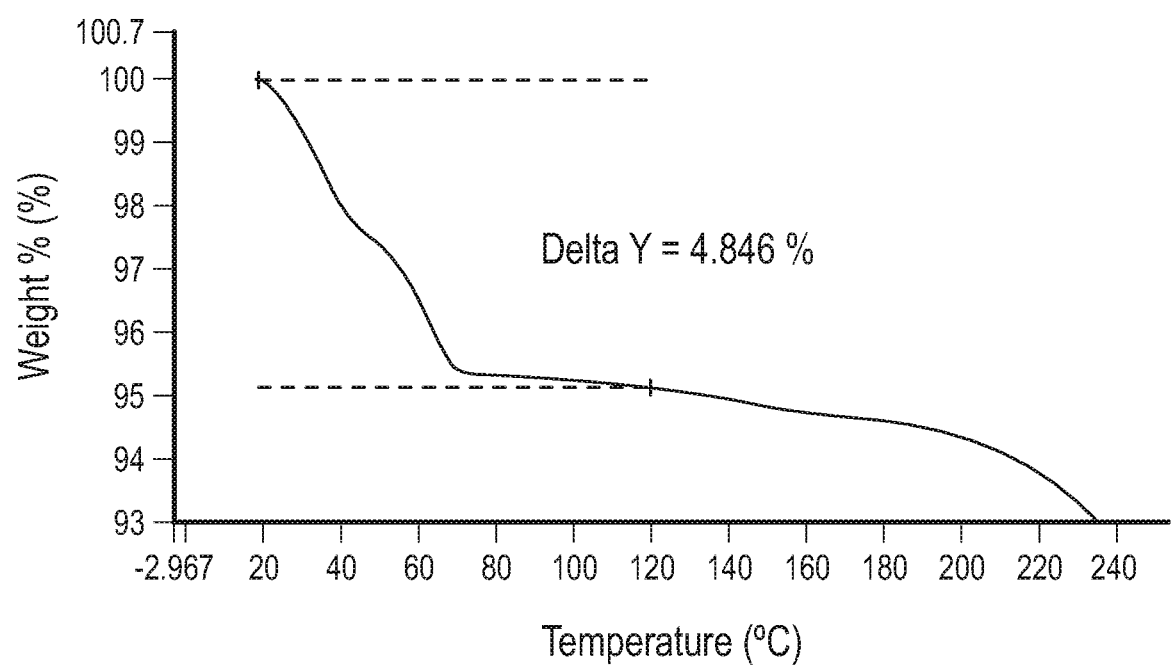
FIG. 12 shows a TGA thermogram of Compound I di-tosylate salt, Form HIII.

In some embodiments, Form HIII has a TGA thermogram substantially as depicted in FIG. 12.

In some embodiments, Form HIII exhibits a differential scanning calorimetry thermogram having endothermic peaks at temperatures of about 67° C. and about 98° C.; and an X-ray powder diffraction pattern comprising a characteristic peak selected from about 7.0, about 9.0, about 9.2, about 10.2, about 17.9, about 20.3, about 22.0, and about 23.8 degrees 2-theta.

Figure 11:
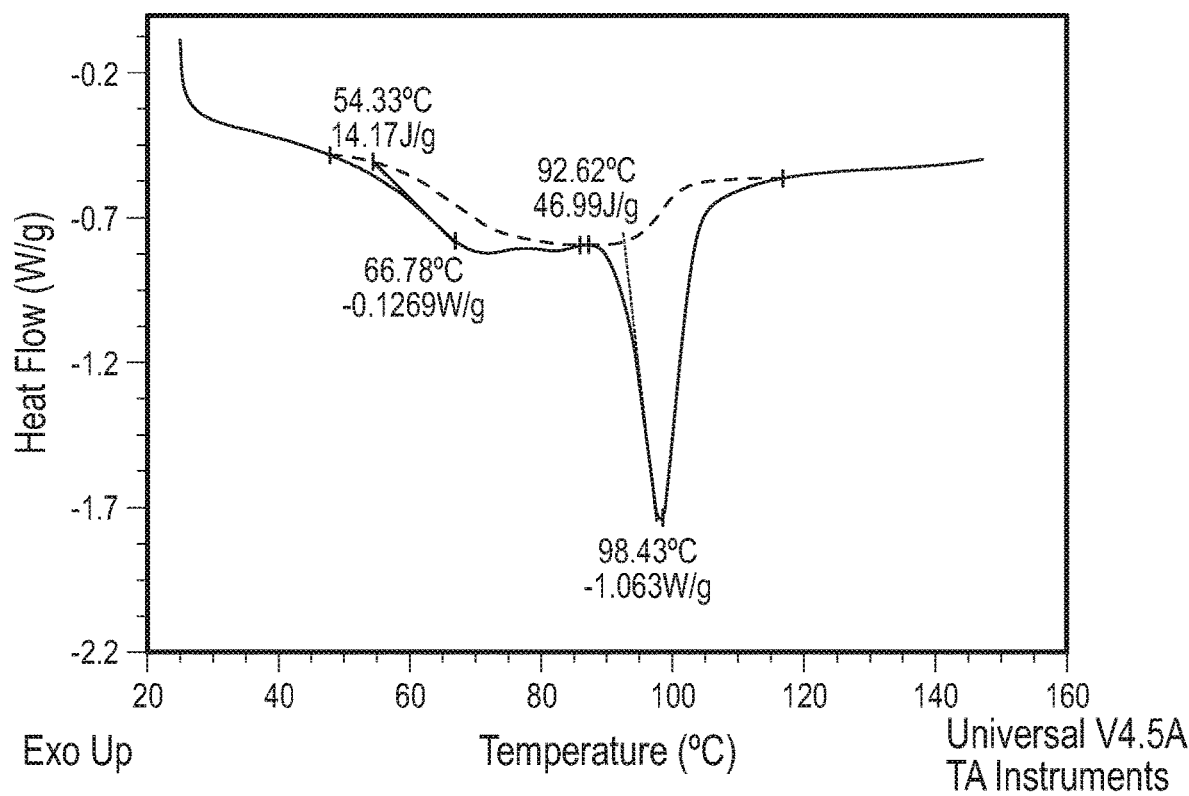
FIG. 11 shows a DSC thermogram of Compound I di-tosylate salt, Form HIII.

In some embodiments, Form HIII has an XRPD pattern substantially as depicted in FIG. 10 and a DSC thermogram substantially as depicted in FIG. 11.

Form DH of Compound I Di-Tosylate Salt

In some embodiments, the present application relates to the crystalline form of Compound I di-tosylate salt referred to as Form DH, which is described below and in the Examples.

In some embodiments, Form DH has an XRPD pattern comprising a characteristic peak, in terms of 2-theta, at about 7.5 degrees. In some embodiments, Form DH has an XRPD pattern comprising a characteristic peak, in terms of 2-theta, at about 9.6 degrees. In some embodiments, Form DH has an XRPD pattern comprising a characteristic peak, in terms of 2-theta, at about 10.7 degrees. In some embodiments, Form DH has an XRPD pattern comprising a characteristic peak, in terms of 2-theta, at about 14.8 degrees. In some embodiments, Form DH has an XRPD pattern comprising a characteristic peak, in terms of 2-theta, at about 20.1 degrees. In some embodiments, Form DH has an XRPD pattern comprising a characteristic peak, in terms of 2-theta, at about 20.7 degrees. In some embodiments, Form DH has an XRPD pattern comprising a characteristic peak, in terms of 2-theta, at about 21.6 degrees. In some embodiments, Form DH has an XRPD pattern comprising a characteristic peak, in terms of 2-theta, at about 22.9 degrees. In some embodiments, Form DH has an XRPD pattern comprising a characteristic peak, in terms of 2-theta, at about 24.7 degrees.

In some embodiments, Form DH has an XRPD pattern comprising two or more characteristic peaks, in terms of 2-theta, selected from about 7.5, about 9.6, about 10.7, about 14.8, about 20.1, about 20.7, about 21.6, about 22.9, and about 24.7 degrees 2-theta.

In some embodiments, Form DH has an XRPD pattern comprising three or more characteristic peaks, in terms of 2-theta, selected from about 7.5, about 9.6, about 10.7, about 14.8, about 20.1, about 20.7, about 21.6, about 22.9, and about 24.7 degrees 2-theta.

Figure 13:
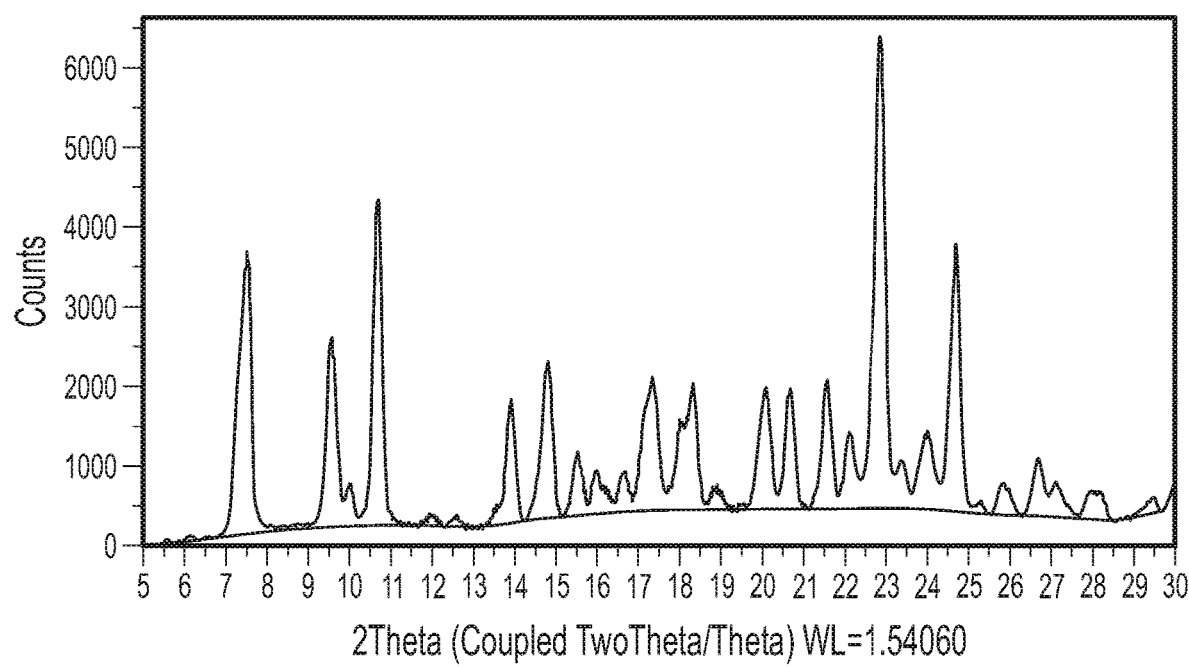
FIG. 13 shows an XRPD pattern of Compound I di-tosylate salt, Form DH.

In some embodiments, Form DH has an X-ray powder diffraction pattern substantially as shown in FIG. 13.

In some embodiments, Form DH exhibits a differential scanning calorimetry thermogram having an endothermic peak at a temperature of about 98° C. In some embodiments, Form DH has a DSC thermogram substantially as depicted in FIG. 14.

Figure 15:
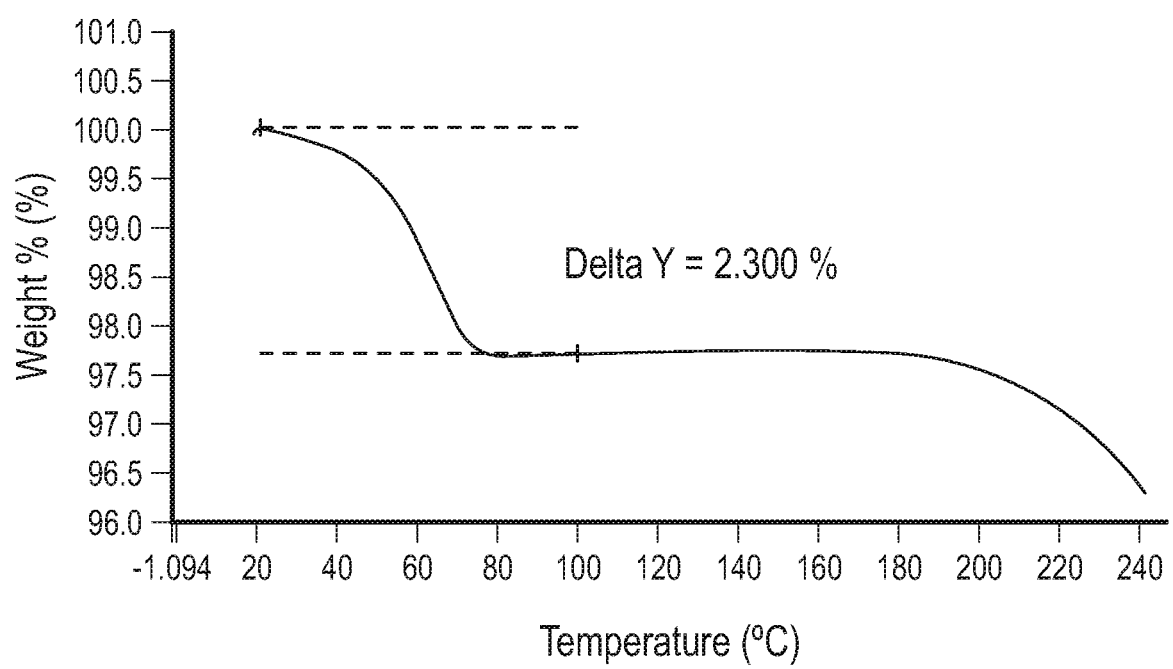
FIG. 15 shows a TGA thermogram of Compound I di-tosylate salt, Form DH.

In some embodiments, Form DH has a TGA thermogram substantially as depicted in FIG. 15.

In some embodiments, Form DH exhibits a differential scanning calorimetry thermogram having an endothermic peak at a temperature of about 98° C.; and an X-ray powder diffraction pattern comprising a characteristic peak selected from about 7.5, about 9.6, about 10.7, about 14.8, about 20.1, about 20.7, about 21.6, about 22.9, and about 24.7 degrees 2-theta.

Figure 14:
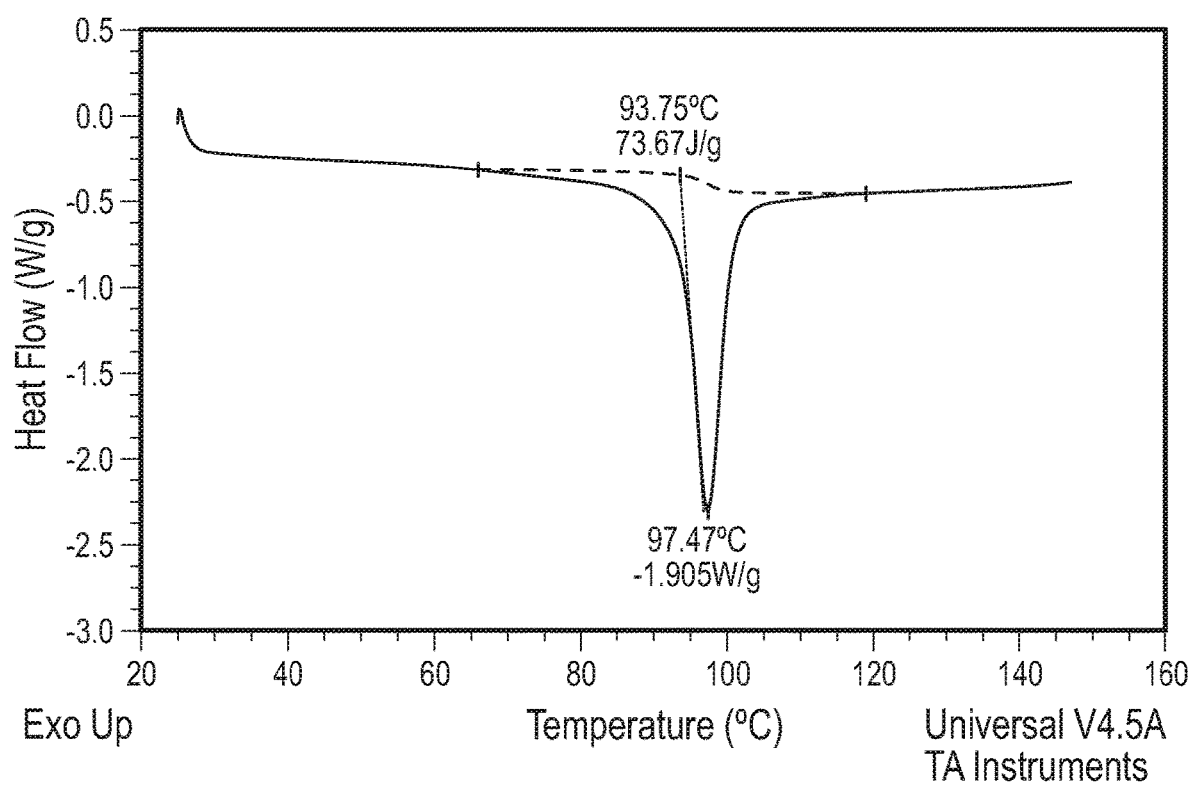
FIG. 14 shows a DSC thermogram of Compound I di-tosylate salt, Form DH.

In some embodiments, Form DH has an XRPD pattern substantially as depicted in FIG. 13 and a DSC thermogram substantially as depicted in FIG. 14.

Form II of Compound I Di-Tosylate Salt

In some embodiments, the present application relates to the crystalline form of Compound I di-tosylate salt referred to as Form II, which is described below and in the Examples.

In some embodiments, Form II has an XRPD pattern comprising a characteristic peak, in terms of 2-theta, at about 6.8 degrees. In some embodiments, Form II has an XRPD pattern comprising a characteristic peak, in terms of 2-theta, selected from about 5.1, about 6.8, and about 10.2 degrees. In some embodiments, Form II has an XRPD pattern comprising a characteristic peak, in terms of 2-theta, selected from about 5.1, about 6.8, about 10.2, about 14.3, about 15.8, about 17.7, and about 23.3 degrees.

In some embodiments, Form II has an XRPD pattern comprising two or more characteristic peaks, in terms of 2-theta, selected from about 5.1, about 6.8, about 10.2, about 14.3, about 15.8, about 17.7, and about 23.3 degrees.

In some embodiments, Form II has an X-ray powder diffraction pattern comprising three or more characteristic peaks, in terms of 2-theta, selected from about 5.1, about 6.8, about 10.2, about 14.3, about 15.8, about 17.7, and about 23.3 degrees.

In some embodiments, Form II has an XRPD pattern comprising one or more characteristic peaks, in terms of 2-theta, selected from about 5.1, about 6.8, about 10.2, about 14.2, about 15.8, about 17.7, about 20.4, about 23.3, about 24.3, and about 26.9 degrees.

In some embodiments, Form II has an XRPD comprising two or more characteristic peaks, in terms of 2-theta, selected from about 5.1, about 6.8, about 10.2, about 14.2, about 15.8, about 17.7, about 20.4, about 23.3, about 24.3, and about 26.9 degrees.

In some embodiments, Form II has an XRPD pattern comprising three or more characteristic peaks, in terms of 2-theta, selected from about 5.1, about 6.8, about 10.2, about 14.2, about 15.8, about 17.7, about 20.4, about 23.3, about 24.3, and about 26.9 degrees.

In some embodiments, Form II has an XRPD pattern comprising four or more characteristic peaks, in terms of 2-theta, selected from about 5.1, about 6.8, about 10.2, about 14.2, about 15.8, about 17.7, about 20.4, about 23.3, about 24.3, and about 26.9 degrees.

Figure 19:
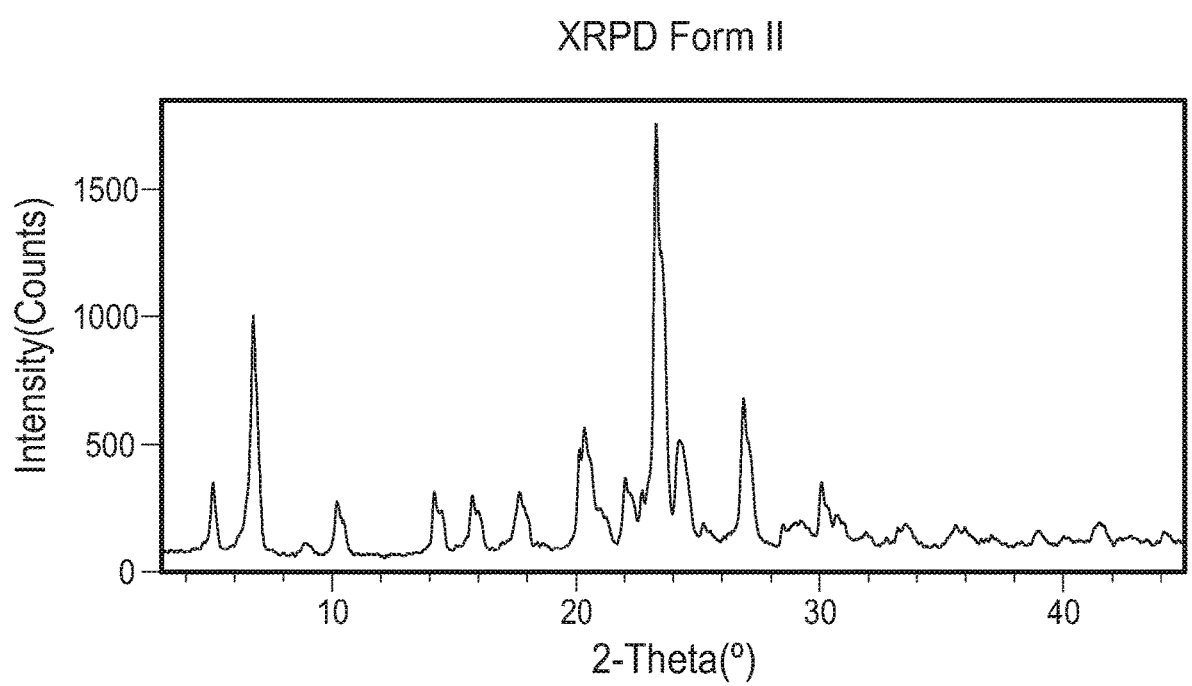
FIG. 19 shows an XRPD pattern of Compound I di-tosylate salt, Form II.

In some embodiments, Form II has an XRPD pattern substantially as depicted in FIG. 19.

Figure 20:
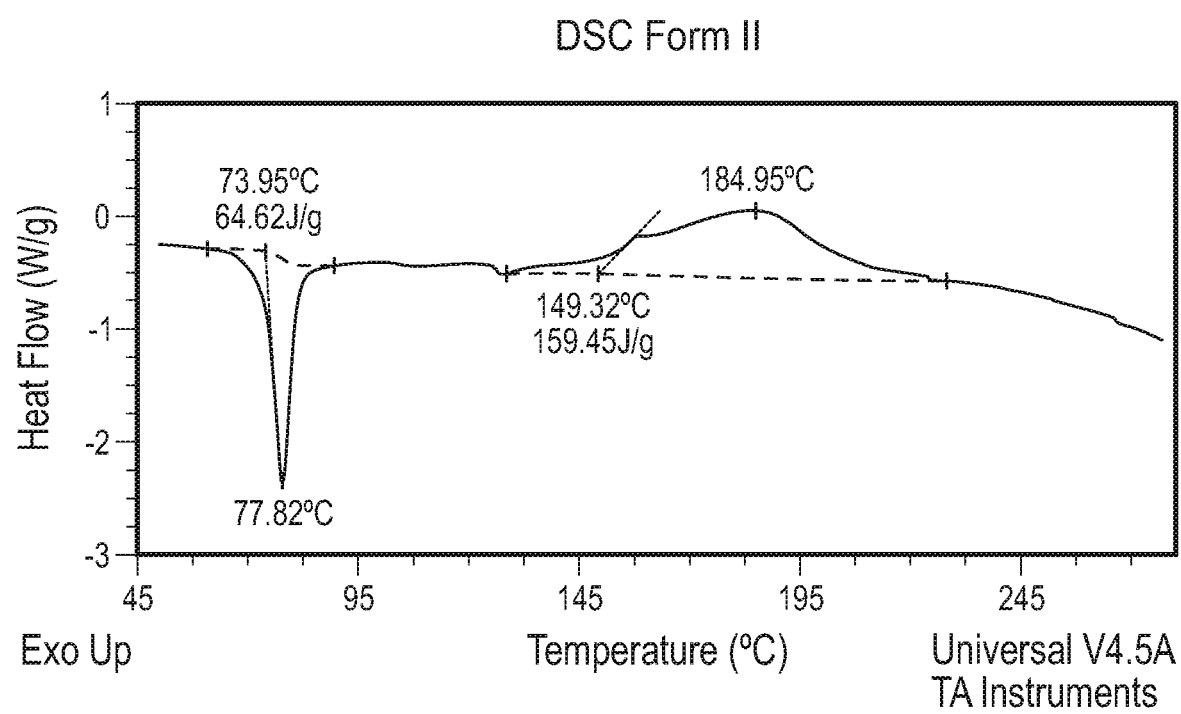
FIG. 20 shows a DSC thermogram of Compound I di-tosylate salt, Form II.
Figure 21:
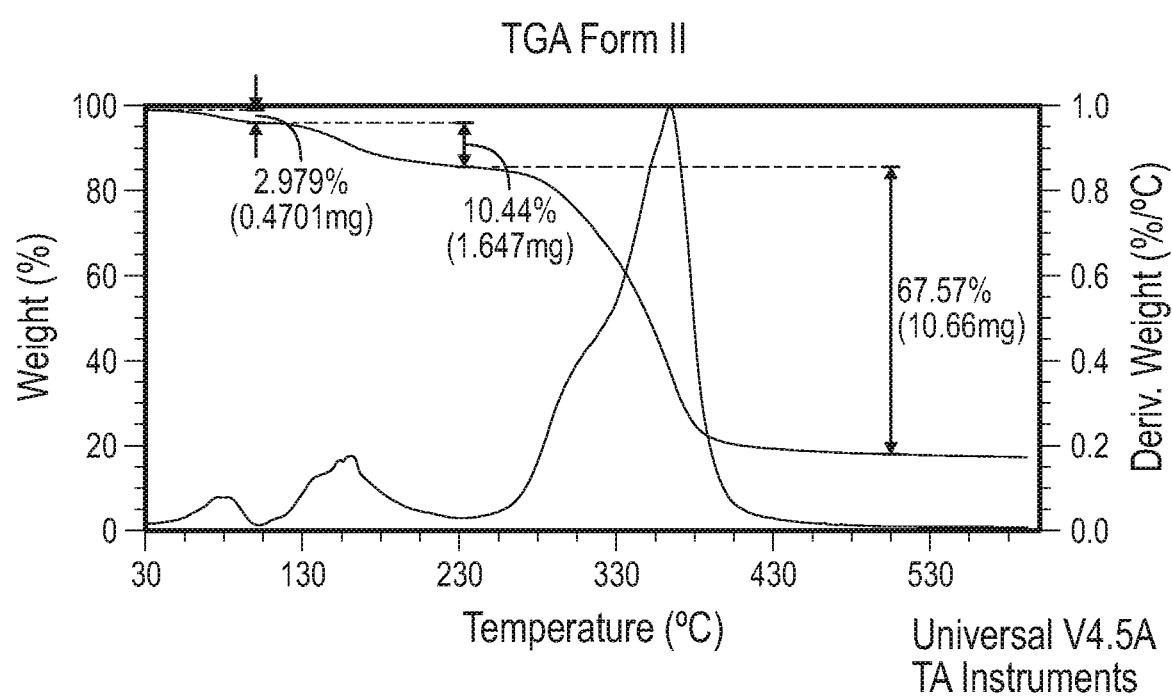
FIG. 21 shows a TGA thermogram of Compound I di-tosylate salt, Form II.

In some embodiments, Form II exhibits a differential scanning calorimetry thermogram having an endothermic peak at a temperature of about 78° C. In some embodiments, Form II has an exothermic peak at a temperature of about 185° C. In some embodiments, Form II exhibits a differential scanning calorimetry thermogram having an endothermic peak at a temperature of about 78° C. and an exothermic peak at a temperature of about 185° C. In some embodiments, Form II has a DSC thermogram substantially as depicted in FIG. 20. In some embodiments, Form II has a TGA thermogram substantially as depicted in FIG. 21.

Form III of Compound I Di-Tosylate Salt

In some embodiments, the present application relates to the crystalline form of Compound I di-tosylate salt referred to as Form III, which is described below and in the Examples.

In some embodiments, Form III has an XRPD pattern comprising a characteristic peak, in terms of 2-theta, at about 4.6 degrees. In some embodiments, Form III has an XRPD pattern comprising a characteristic peak, in terms of 2-theta, selected from about 4.6 and about 5.2 degrees. In some embodiments, Form III has an XRPD pattern comprising a characteristic peak, in terms of 2-theta, selected from about 4.6, about 5.2, about 6.4, about 9.2, about 22.8, and about 24.2 degrees.

In some embodiments, Form III has an XRPD pattern comprising two or more characteristic peaks, in terms of 2-theta, selected from about 4.6, about 5.2, about 6.4, about 9.2, about 22.8, and about 24.2 degrees.

In some embodiments, Form III has an X-ray powder diffraction pattern comprising three or more characteristic peaks, in terms of 2-theta, selected from about 4.6, about 5.2, about 6.4, about 9.2, about 22.8, and about 24.2 degrees.

In some embodiments, Form III has an XRPD pattern comprising one or more characteristic peaks, in terms of 2-theta, selected from about 4.6, about 5.2, about 6.4, about 9.2, about 14.0, about 16.3, about 18.4, about 22.8, and about 24.2 degrees.

In some embodiments, Form III has an XRPD comprising two or more characteristic peaks, in terms of 2-theta, selected from about 4.6, about 5.2, about 6.4, about 9.2, about 14.0, about 16.3, about 18.4, about 22.8, and about 24.2 degrees.

In some embodiments, Form III has an XRPD pattern comprising three or more characteristic peaks, in terms of 2-theta, selected from about 4.6, about 5.2, about 6.4, about 9.2, about 14.0, about 16.3, about 18.4, about 22.8, and about 24.2 degrees.

In some embodiments, Form III has an XRPD pattern comprising four or more characteristic peaks, in terms of 2-theta, selected from about 4.6, about 5.2, about 6.4, about 9.2, about 14.0, about 16.3, about 18.4, about 22.8, and about 24.2 degrees.

Figure 22:
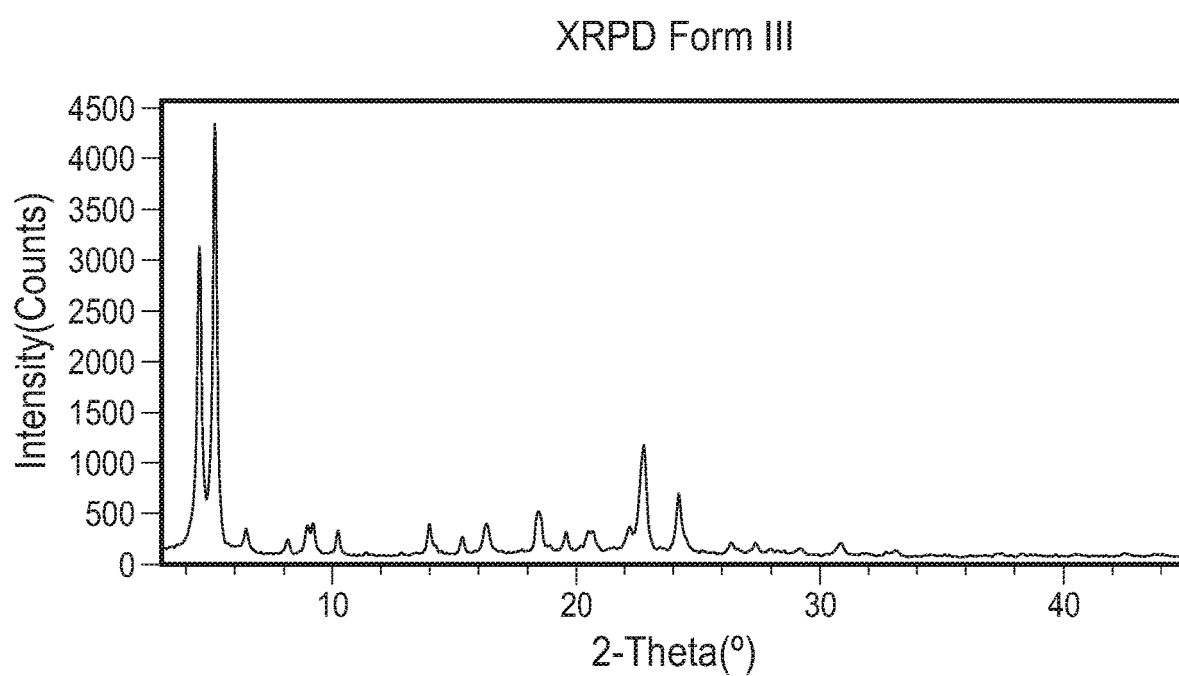
FIG. 22 shows an XRPD pattern of Compound I di-tosylate salt, Form III.

In some embodiments, Form III has an XRPD pattern substantially as depicted in FIG. 22.

Figure 23:
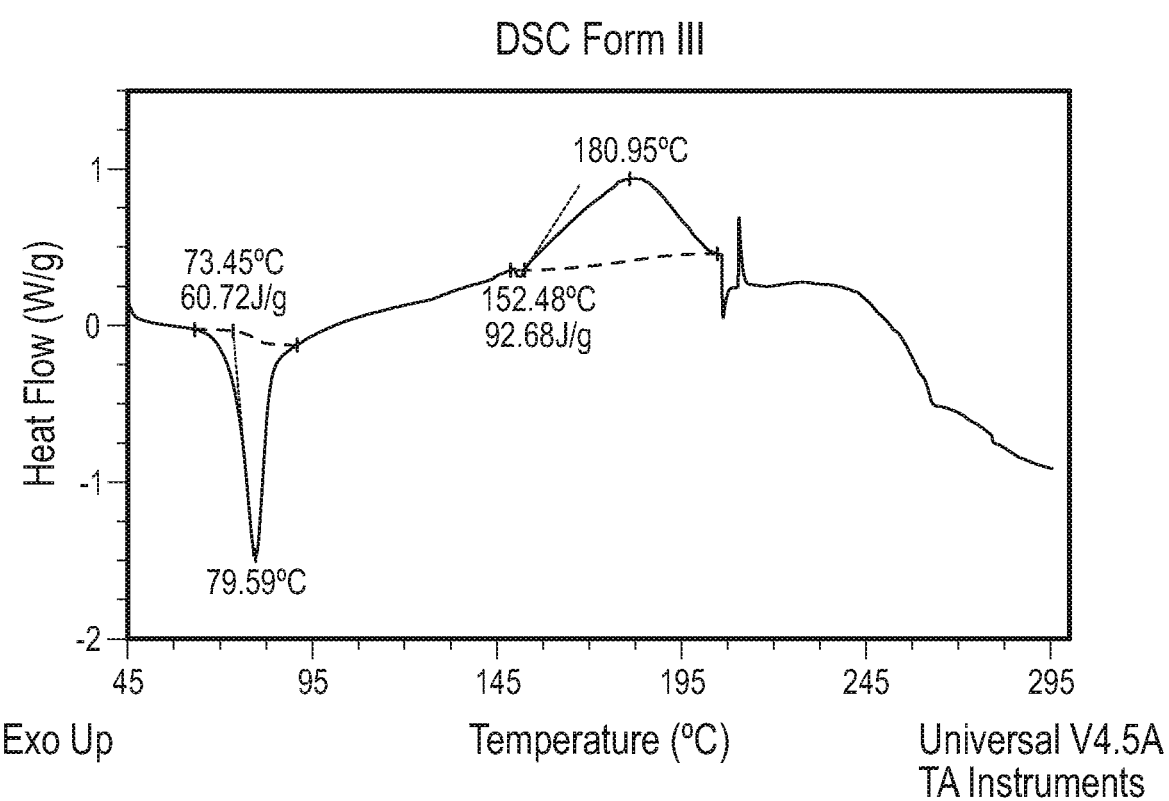
FIG. 23 shows a DSC thermogram of Compound I di-tosylate salt, Form III.
Figure 24:
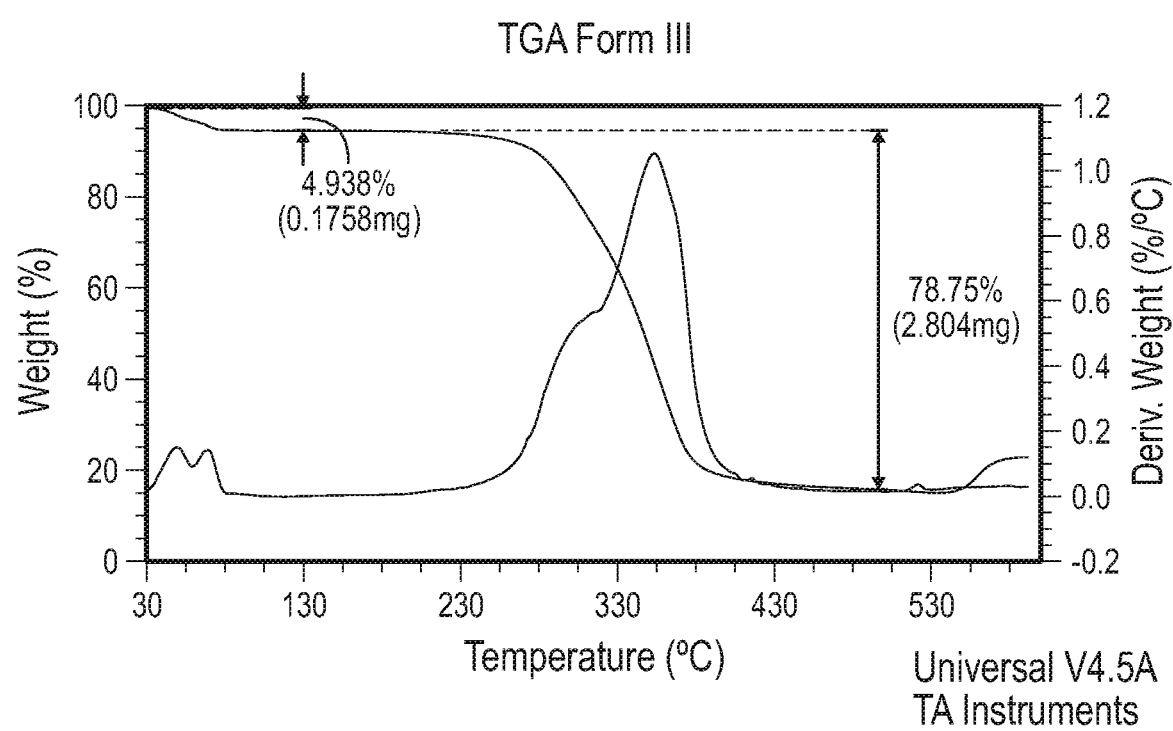
FIG. 24 shows a TGA thermogram of Compound I di-tosylate salt, Form III.

In some embodiments, Form III exhibits a differential scanning calorimetry thermogram having an endothermic peak at a temperature of about 80° C. In some embodiments, Form III has an exothermic peak at a temperature of about 181° C. In some embodiments, Form III exhibits a differential scanning calorimetry thermogram having an endothermic peak at a temperature of about 80° C. and an exothermic peak at a temperature of about 181° C. In some embodiments, Form III has a DSC thermogram substantially as depicted in FIG. 23. In some embodiments, Form III has a TGA thermogram substantially as depicted in FIG. 24.

Form IIIa of Compound I Di-Tosylate Salt

In some embodiments, the present application relates to the crystalline form of Compound I di-tosylate salt referred to as Form IIIa, which is described below and in the Examples.

In some embodiments, Form IIIa has an XRPD pattern comprising a characteristic peak, in terms of 2-theta, selected from about 4.5, about 5.1, and about 6.9 degrees. In some embodiments, Form IIIa has an XRPD pattern comprising a characteristic peak, in terms of 2-theta, selected from about 4.5, about 5.1, about 6.9, about 8.1, about 10.1, about 22.7, and about 24.1 degrees.

In some embodiments, Form IIIa has an XRPD pattern comprising two or more characteristic peaks, in terms of 2-theta, selected from about 4.5, about 5.1, about 6.9, about 8.1, about 10.1, about 22.7, and about 24.1 degrees.

In some embodiments, Form IIIa has an X-ray powder diffraction pattern comprising three or more characteristic peaks, in terms of 2-theta, selected from about 4.5, about 5.1, about 6.9, about 8.1, about 10.1, about 22.7, and about 24.1 degrees.

In some embodiments, Form IIIa has an XRPD pattern comprising one or more characteristic peaks, in terms of 2-theta, selected from about 4.5, about 5.1, about 6.9, about 8.1, about 10.1, about 16.3, about 20.8, about 22.7, and about 24.1 degrees.

In some embodiments, Form IIIa has an XRPD pattern comprising two or more characteristic peaks, in terms of 2-theta, selected from about 4.5, about 5.1, about 6.9, about 8.1, about 10.1, about 16.3, about 20.8, about 22.7, and about 24.1 degrees.

In some embodiments, Form IIIa has an X-ray powder diffraction pattern comprising three or more characteristic peaks, in terms of 2-theta, selected from about 4.5, about 5.1, about 6.9, about 8.1, about 10.1, about 16.3, about 20.8, about 22.7, and about 24.1 degrees.

Figure 25:
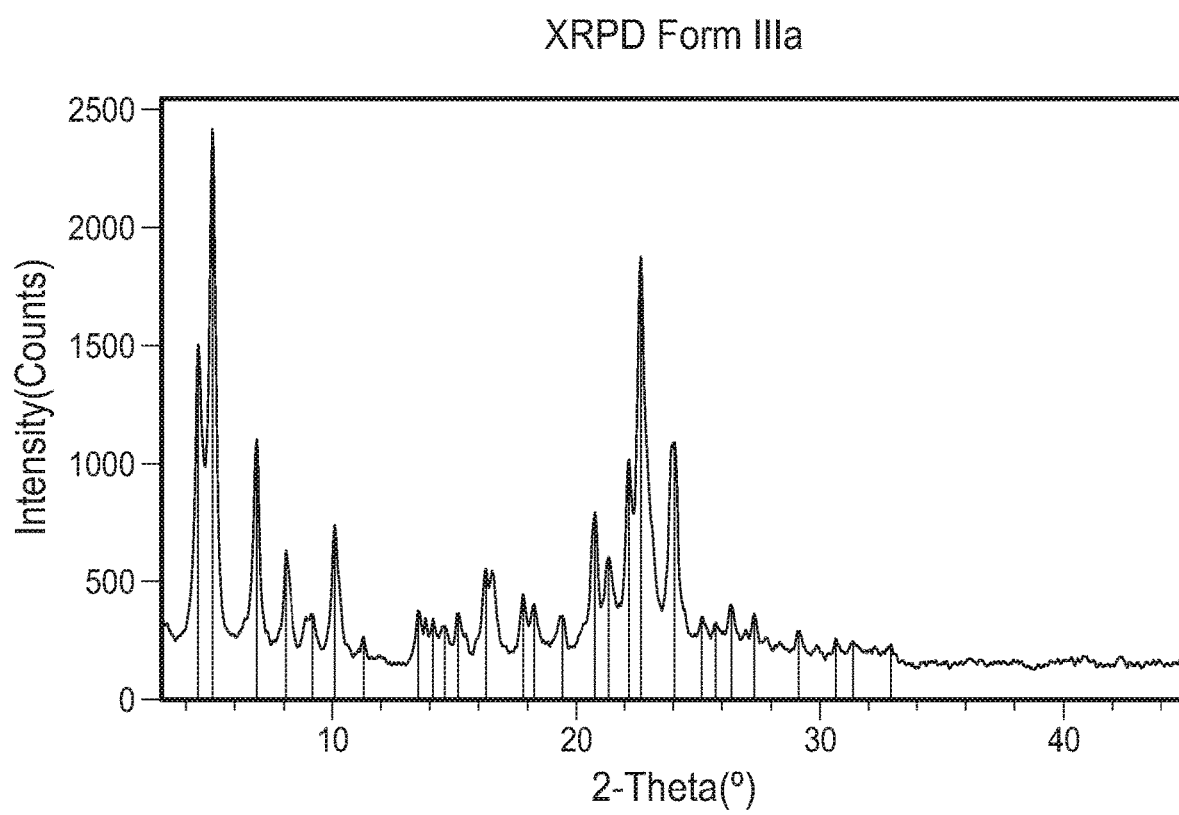
FIG. 25 shows an XRPD pattern of Compound I di-tosylate salt, Form IIIa.

In some embodiments, Form IIIa has an XRPD pattern substantially as depicted in FIG. 25.

Form IV of Compound I Di-Tosylate Salt

In some embodiments, the present application relates to the crystalline form of Compound I di-tosylate salt referred to as Form IV, which is described below and in the Examples.

In some embodiments, Form IV has an XRPD pattern comprising a characteristic peak, in terms of 2-theta, at about 7.1 degrees. In some embodiments, Form IV has an XRPD pattern comprising a characteristic peak, in terms of 2-theta, selected from about 7.1, about 8.9, and about 10.5 degrees. In some embodiments, Form IV has an XRPD pattern comprising a characteristic peak, in terms of 2-theta, selected from about 7.1, about 8.9, about 10.5, about 14.6, and about 18.0 degrees.

In some embodiments, Form IV has an XRPD pattern comprising two or more characteristic peaks, in terms of 2-theta, selected from about 7.1, about 8.9, about 10.5, about 14.6, and about 18.0 degrees.

In some embodiments, Form IV has an X-ray powder diffraction pattern comprising three or more characteristic peaks, in terms of 2-theta, selected from about 7.1, about 8.9, about 10.5, about 14.6, and about 18.0 degrees.

In some embodiments, Form IV has an XRPD pattern comprising one or more characteristic peaks, in terms of 2-theta, selected from about 7.1, about 8.9, about 10.5, about 14.6, about 18.0, about 20.1, about 23.1, and about 24.8 degrees.

In some embodiments, Form IV has an XRPD comprising two or more characteristic peaks, in terms of 2-theta, selected from about 7.1, about 8.9, about 10.5, about 14.6, about 18.0, about 20.1, about 23.1, and about 24.8 degrees.

In some embodiments, Form IV has an XRPD pattern comprising three or more characteristic peaks, in terms of 2-theta, selected from about 7.1, about 8.9, about 10.5, about 14.6, about 18.0, about 20.1, about 23.1, and about 24.8 degrees.

In some embodiments, Form IV has an XRPD pattern comprising four or more characteristic peaks, in terms of 2-theta, selected from about 7.1, about 8.9, about 10.5, about 14.6, about 18.0, about 20.1, about 23.1, and about 24.8 degrees.

Figure 26:
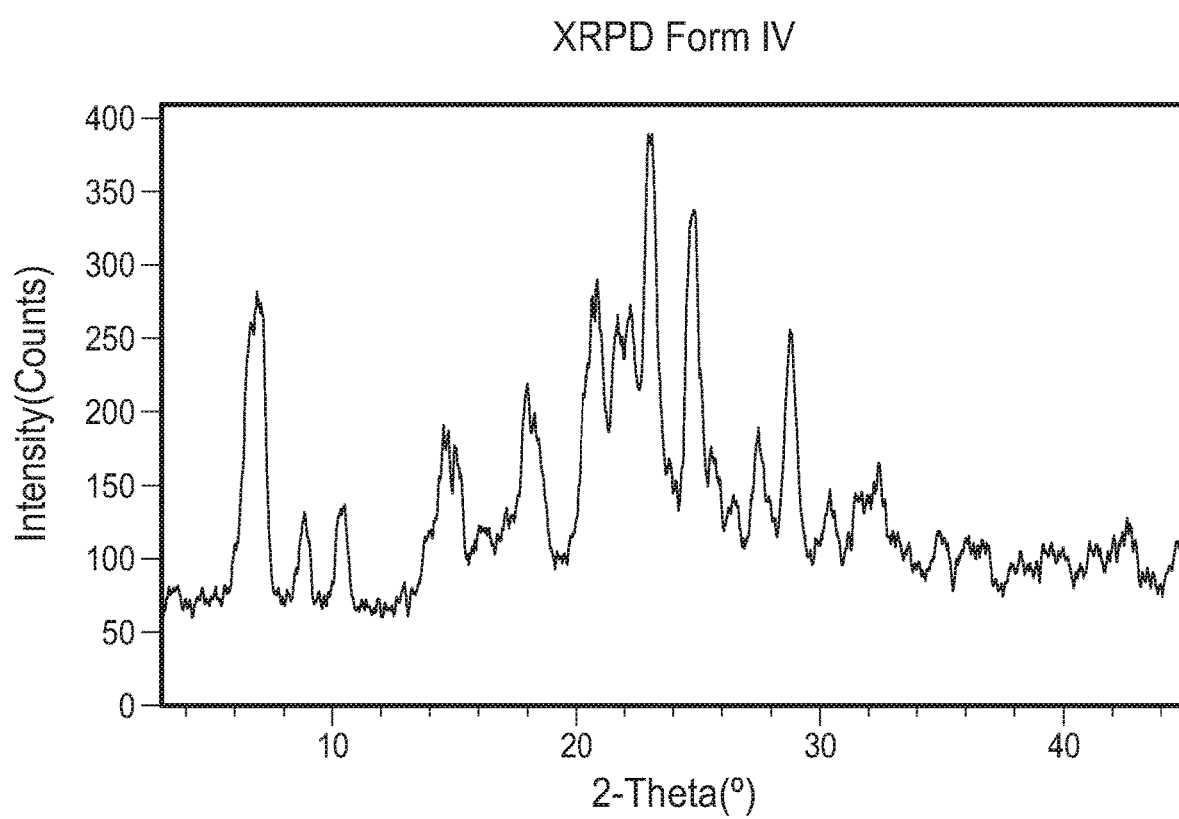
FIG. 26 shows an XRPD pattern of Compound I di-tosylate salt, Form IV.

In some embodiments, Form IV has an XRPD pattern substantially as depicted in FIG. 26.

Figure 27:
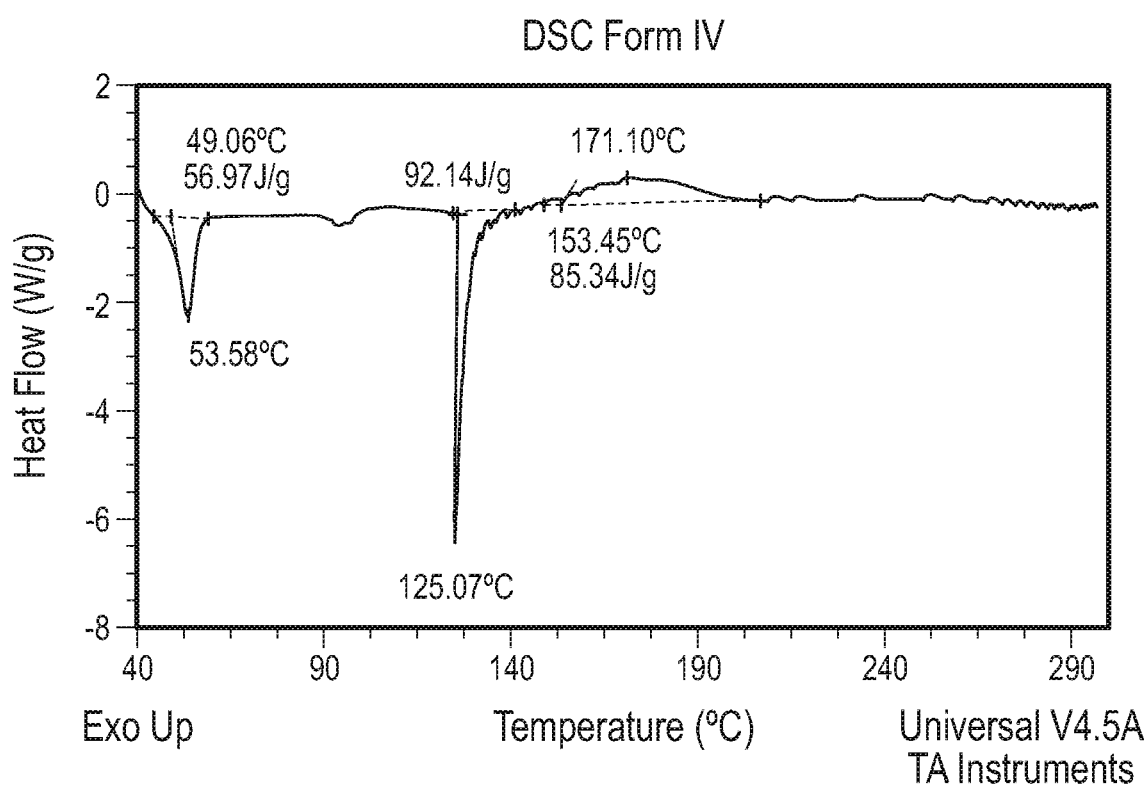
FIG. 27 shows a DSC thermogram of Compound I di-tosylate salt, Form IV.
Figure 28:
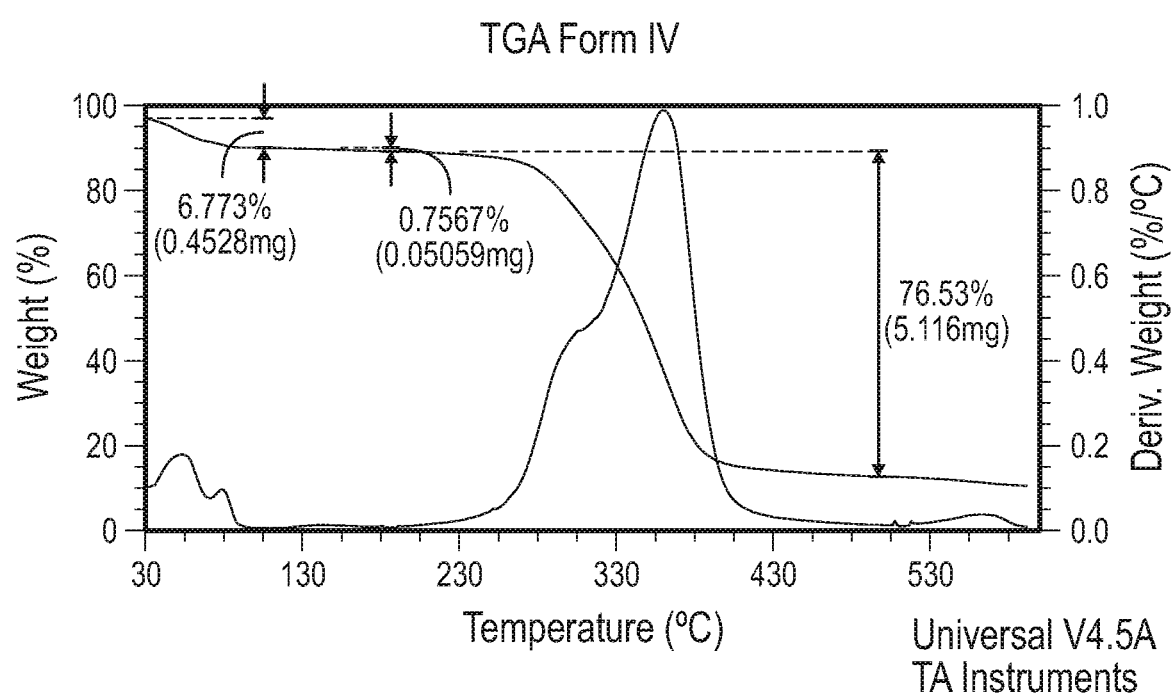
FIG. 28 shows a TGA thermogram of Compound I di-tosylate salt, Form IV.

In some embodiments, Form IV exhibits a differential scanning calorimetry thermogram having an endothermic peak at a temperature of about 54° C. In some embodiments, Form IV has an endothermic peak at a temperature of about 125° C. In some embodiments, Form IV has an exothermic peak at a temperature of about 171° C. In some embodiments, Form IV has endothermic peaks at temperatures of about 54° C. and about 125° C. and an exothermic peak at a temperature of about 171° C. In some embodiments, Form IV has a DSC thermogram substantially as depicted in FIG. 27. In some embodiments, Form IV has a TGA thermogram substantially as depicted in FIG. 28.

Form IVa of Compound I Di-Tosylate Salt

In some embodiments, the present application relates to the crystalline form of Compound I di-tosylate salt referred to as Form IVa, which is described below and in the Examples.

In some embodiments, Form IVa has an XRPD pattern comprising a characteristic peak, in terms of 2-theta, at about 6.9 degrees. In some embodiments, Form IVa has an XRPD pattern comprising a characteristic peak, in terms of 2-theta, selected from about 6.4, about 6.9, and about 10.5 degrees. In some embodiments, Form IVa has an XRPD pattern comprising a characteristic peak, in terms of 2-theta, selected from about 6.4, about 6.9, about 8.7, about 10.1, and about 14.4 degrees.

In some embodiments, Form IVa has an XRPD pattern comprising two or more characteristic peaks, in terms of 2-theta, selected from about 6.4, about 6.9, about 8.7, about 10.1, and about 14.4 degrees.

In some embodiments, Form IVa has an X-ray powder diffraction pattern comprising three or more characteristic peaks, in terms of 2-theta, selected from about 6.4, about 6.9, about 8.7, about 10.1, and about 14.4 degrees.

In some embodiments, Form IVa has an XRPD pattern comprising one or more characteristic peaks, in terms of 2-theta, selected from about 6.4, about 6.9, about 8.7, about 10.1, about 14.4, about 22.1, about 22.8, about 24.4, about 24.7, and about 28.5 degrees.

In some embodiments, Form IVa has an XRPD comprising two or more characteristic peaks, in terms of 2-theta, selected from about 6.4, about 6.9, about 8.7, about 10.1, about 14.4, about 22.1, about 22.8, about 24.4, about 24.7, and about 28.5 degrees.

In some embodiments, Form IVa has an XRPD pattern comprising three or more characteristic peaks, in terms of 2-theta, selected from about 6.4, about 6.9, about 8.7, about 10.1, about 14.4, about 22.1, about 22.8, about 24.4, about 24.7, and about 28.5 degrees.

In some embodiments, Form IVa has an XRPD pattern comprising four or more characteristic peaks, in terms of 2-theta, selected from about 6.4, about 6.9, about 8.7, about 10.1, about 14.4, about 22.1, about 22.8, about 24.4, about 24.7, and about 28.5 degrees.

Figure 29:
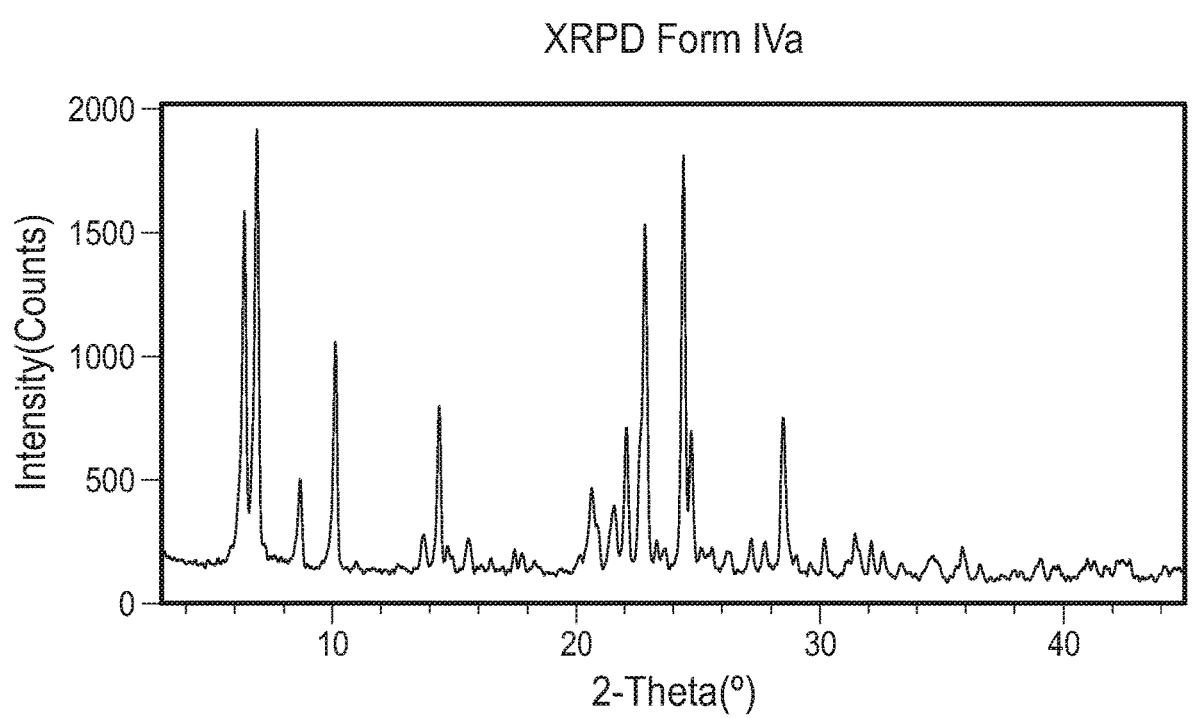
FIG. 29 shows an XRPD pattern of Compound I di-tosylate salt, Form IVa.

In some embodiments, Form IVa has an XRPD pattern substantially as depicted in FIG. 29.

Figure 30:
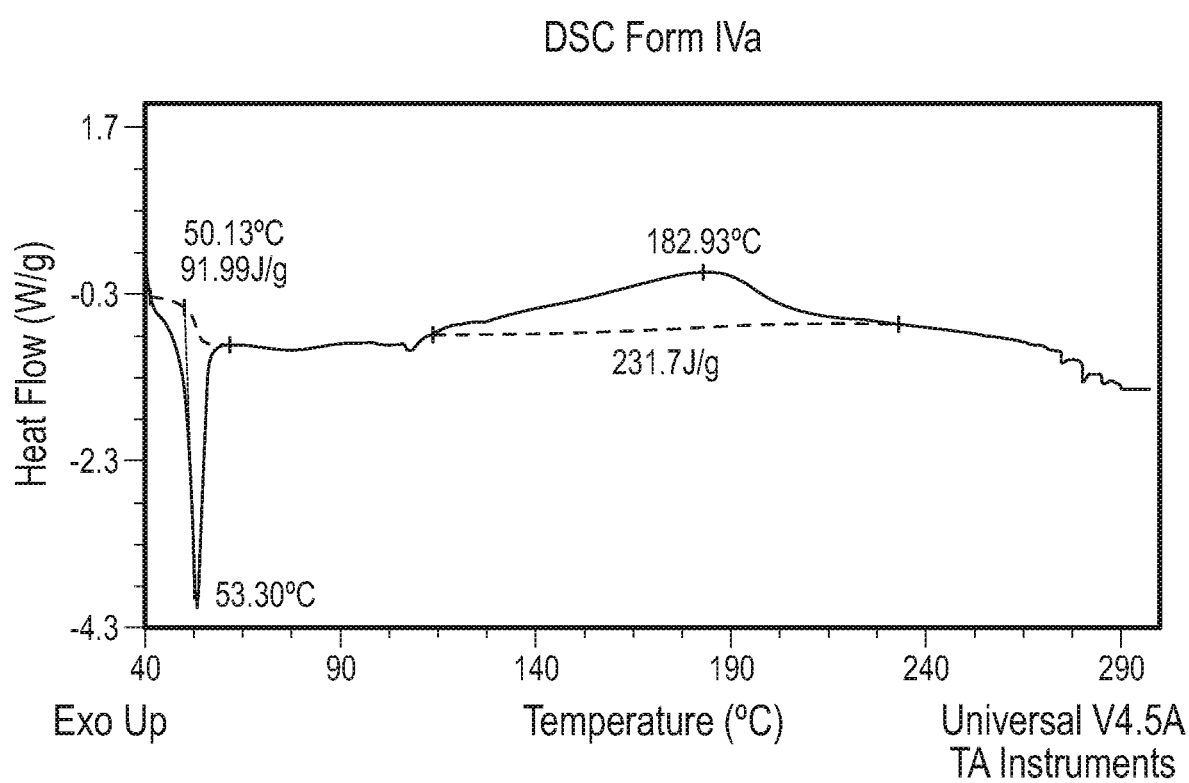
FIG. 30 shows a DSC thermogram of Compound I di-tosylate salt, Form IVa.
Figure 31:
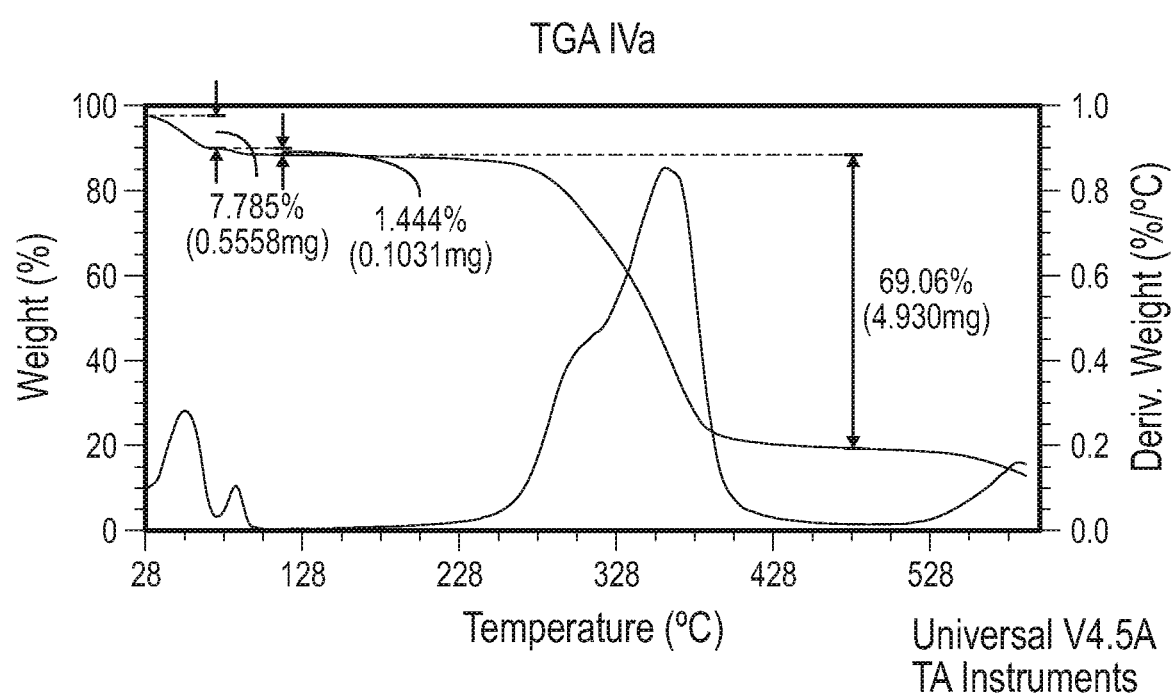
FIG. 31 shows a TGA thermogram of Compound I di-tosylate salt, Form IVa.

In some embodiments, Form IVa exhibits a differential scanning calorimetry thermogram having an endothermic peak at a temperature of about 53° C. In some embodiments, Form IVa has an exothermic peak at a temperature of about 183° C. In some embodiments, Form IVa exhibits a differential scanning calorimetry thermogram having an endothermic peak at a temperature of about 53° C. and an exothermic peak at a temperature of about 183° C. In some embodiments, Form IVa has a DSC thermogram substantially as depicted in FIG. 30. In some embodiments, Form IVa has a TGA thermogram substantially as depicted in FIG. 31.

Form V of Compound I Di-Tosylate Salt

In some embodiments, the present application relates to the crystalline form of Compound I di-tosylate salt referred to as Form V, which is described below and in the Examples.

In some embodiments, Form V has an XRPD pattern comprising a characteristic peak, in terms of 2-theta, at about 7.3 degrees. In some embodiments, Form V has an XRPD pattern comprising a characteristic peak, in terms of 2-theta, selected from about 5.6, about 7.3, and about 10.3 degrees. In some embodiments, Form V has an XRPD pattern comprising a characteristic peak, in terms of 2-theta, selected from about 5.6, about 7.3, about 10.8, about 16.7, about 17.6, and about 21.2 degrees.

In some embodiments, Form V has an XRPD pattern comprising two or more characteristic peaks, in terms of 2-theta, selected from about 5.6, about 7.3, about 10.8, about 16.7, about 17.6, and about 21.2 degrees.

In some embodiments, Form V has an X-ray powder diffraction pattern comprising three or more characteristic peaks, in terms of 2-theta, selected from about 5.6, about 7.3, about 10.8, about 16.7, about 17.6, and about 21.2 degrees.

In some embodiments, Form V has an XRPD pattern comprising one or more characteristic peaks, in terms of 2-theta, selected from about 5.6, about 7.3, about 10.8, about 16.7, about 17.6, about 20.1, about 21.2, about 23.3, and about 24.3 degrees.

In some embodiments, Form V has an XRPD comprising two or more characteristic peaks, in terms of 2-theta, selected from about 5.6, about 7.3, about 10.8, about 16.7, about 17.6, about 20.1, about 21.2, about 23.3, and about 24.3 degrees.

In some embodiments, Form V has an XRPD pattern comprising three or more characteristic peaks, in terms of 2-theta, selected from about 5.6, about 7.3, about 10.8, about 16.7, about 17.6, about 20.1, about 21.2, about 23.3, and about 24.3 degrees.

In some embodiments, Form V has an XRPD pattern comprising four or more characteristic peaks, in terms of 2-theta, selected from about 5.6, about 7.3, about 10.8, about 16.7, about 17.6, about 20.1, about 21.2, about 23.3, and about 24.3 degrees.

Figure 32:
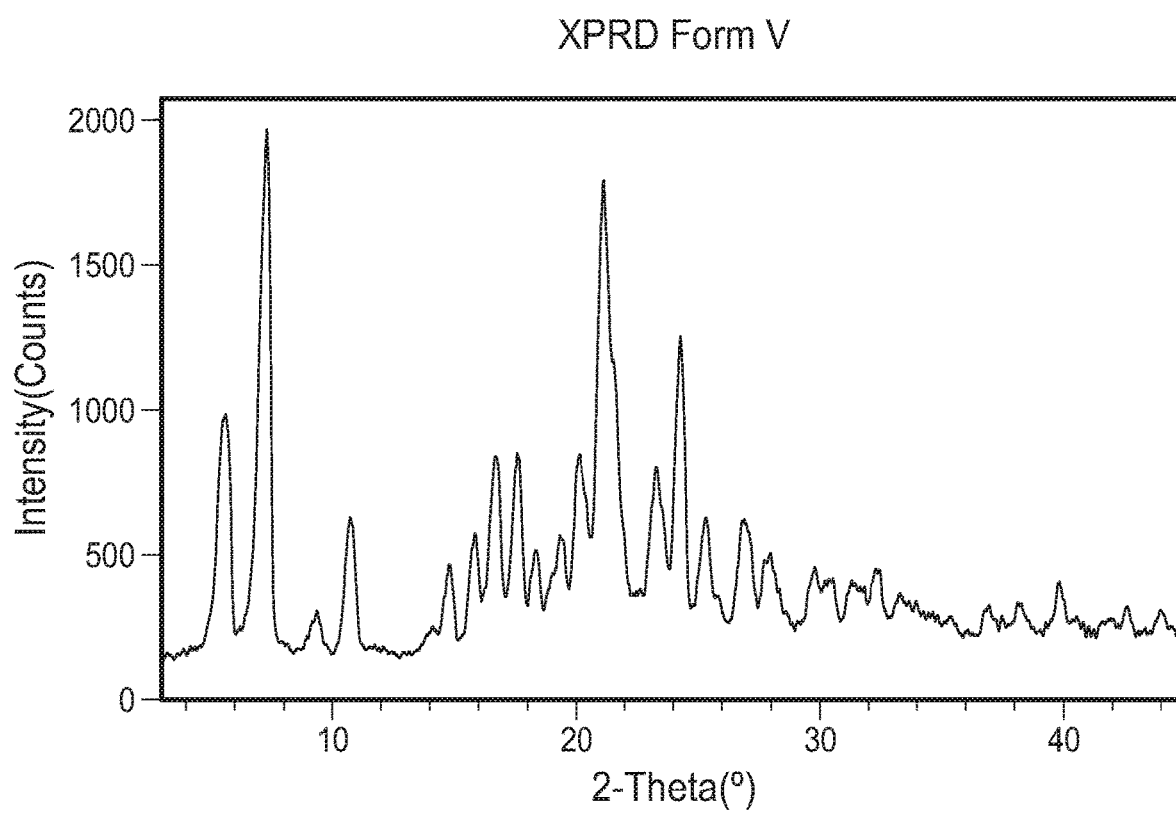
FIG. 32 shows an XRPD pattern of Compound I di-tosylate salt, Form V.

In some embodiments, Form V has an XRPD pattern substantially as depicted in FIG. 32.

Figure 33:
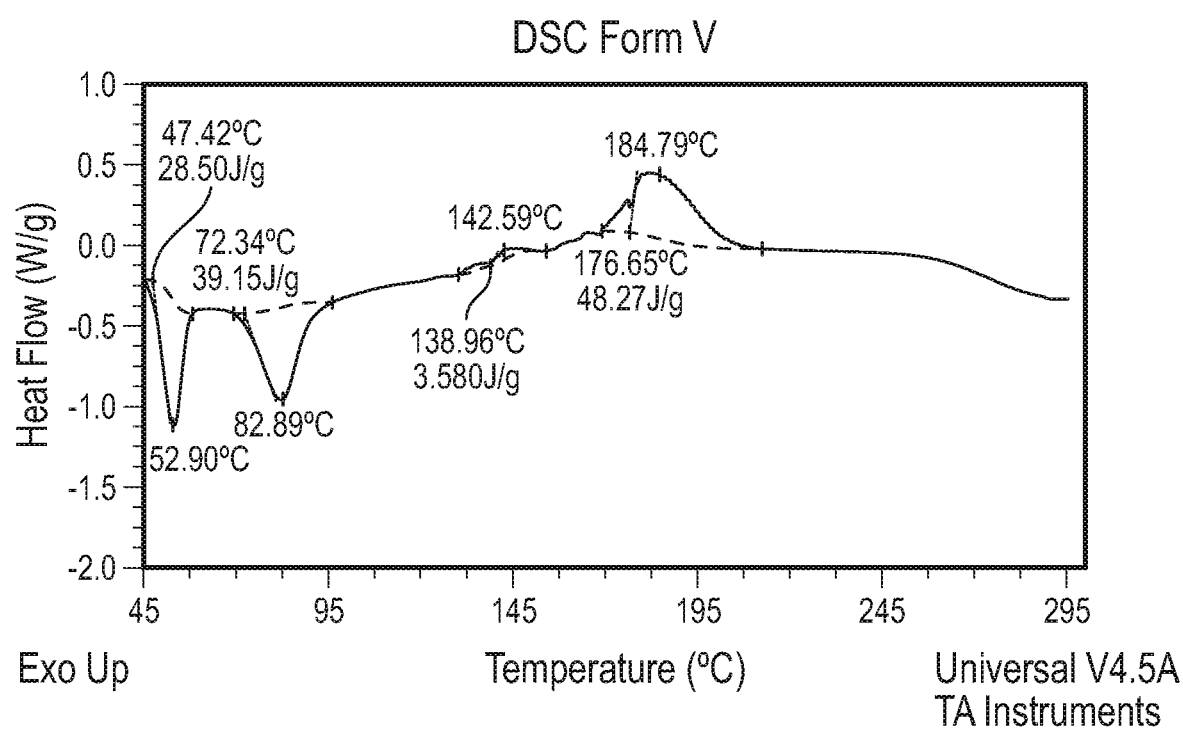
FIG. 33 shows a DSC thermogram of Compound I di-tosylate salt, Form V.
Figure 34:
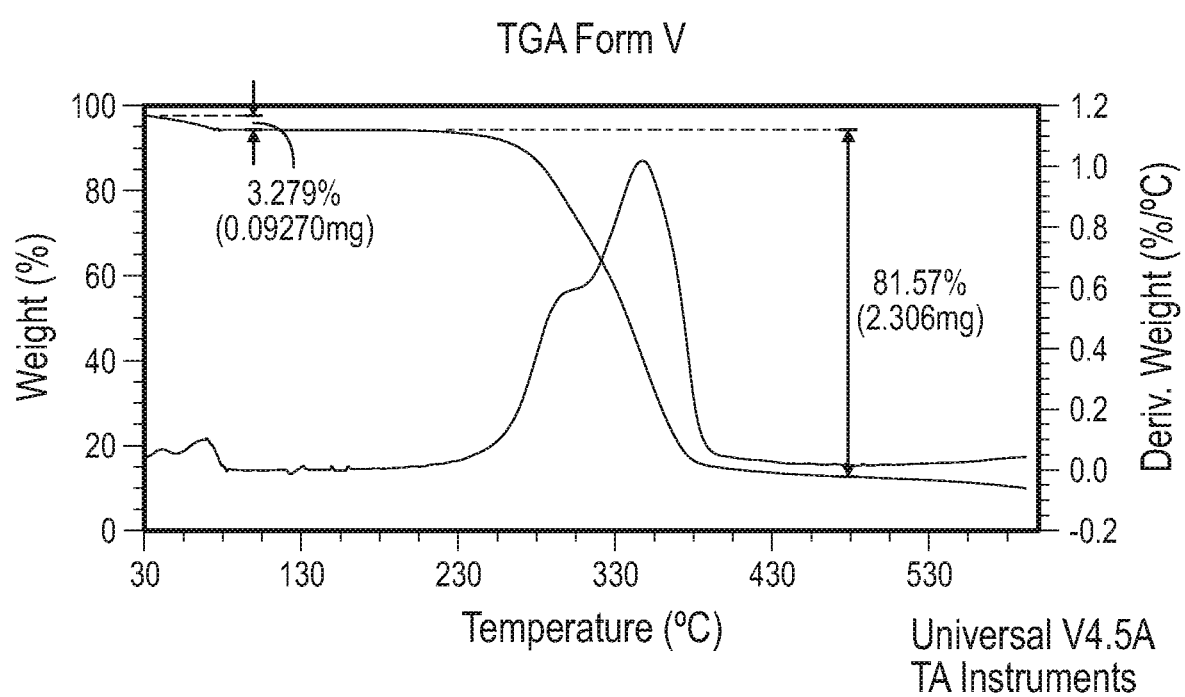
FIG. 34 shows a TGA thermogram of Compound I di-tosylate salt, Form V.

In some embodiments, Form V exhibits a differential scanning calorimetry thermogram having an endothermic peak at a temperature of about 53° C. In some embodiments, Form V exhibits a differential scanning calorimetry thermogram having an endothermic peak at a temperature of about 83° C. In some embodiments, Form V has an exothermic peak at a temperature of about 185° C. In some embodiments, Form V exhibits a differential scanning calorimetry thermogram having endothermic peaks at temperatures of about 53° C. and about 83° C. and an exothermic peak at a temperature of about 185° C. In some embodiments, Form V has a DSC thermogram substantially as depicted in FIG. 33. In some embodiments, Form V has a TGA thermogram substantially as depicted in FIG. 34.

Form VI of Compound I Di-Tosylate Salt

In some embodiments, the present application relates to the crystalline form of Compound I di-tosylate salt referred to as Form VI, which is described below and in the Examples.

In some embodiments, Form VI has an XRPD pattern comprising a characteristic peak, in terms of 2-theta, selected from about 7.4, about 10.9, and about 14.1 degrees. In some embodiments, Form VI has an XRPD pattern comprising a characteristic peak, in terms of 2-theta, selected from about 7.4, about 10.9, about 14.1, about 16.0, about 17.1, and about 17.4 degrees.

In some embodiments, Form VI has an XRPD pattern comprising two or more characteristic peaks, in terms of 2-theta, selected from about 7.4, about 10.9, about 14.1, about 16.0, about 17.1, and about 17.4 degrees.

In some embodiments, Form VI has an X-ray powder diffraction pattern comprising three or more characteristic peaks, in terms of 2-theta, selected from about 7.4, about 10.9, about 14.1, about 16.0, about 17.1, and about 17.4 degrees.

In some embodiments, Form VI has an XRPD pattern comprising one or more characteristic peaks, in terms of 2-theta, selected from about 7.4, about 10.9, about 14.1, about 16.0, about 17.1, about 17.4, about 22.8, about 23.5, and about 24.5 degrees.

In some embodiments, Form VI has an XRPD comprising two or more characteristic peaks, in terms of 2-theta, selected from about 7.4, about 10.9, about 14.1, about 16.0, about 17.1, about 17.4, about 22.8, about 23.5, and about 24.5 degrees.

In some embodiments, Form VI has an XRPD pattern comprising three or more characteristic peaks, in terms of 2-theta, selected from about 7.4, about 10.9, about 14.1, about 16.0, about 17.1, about 17.4, about 22.8, about 23.5, and about 24.5 degrees.

In some embodiments, Form VI has an XRPD pattern comprising four or more characteristic peaks, in terms of 2-theta, selected from about 7.4, about 10.9, about 14.1, about 16.0, about 17.1, about 17.4, about 22.8, about 23.5, and about 24.5 degrees.

Figure 35:
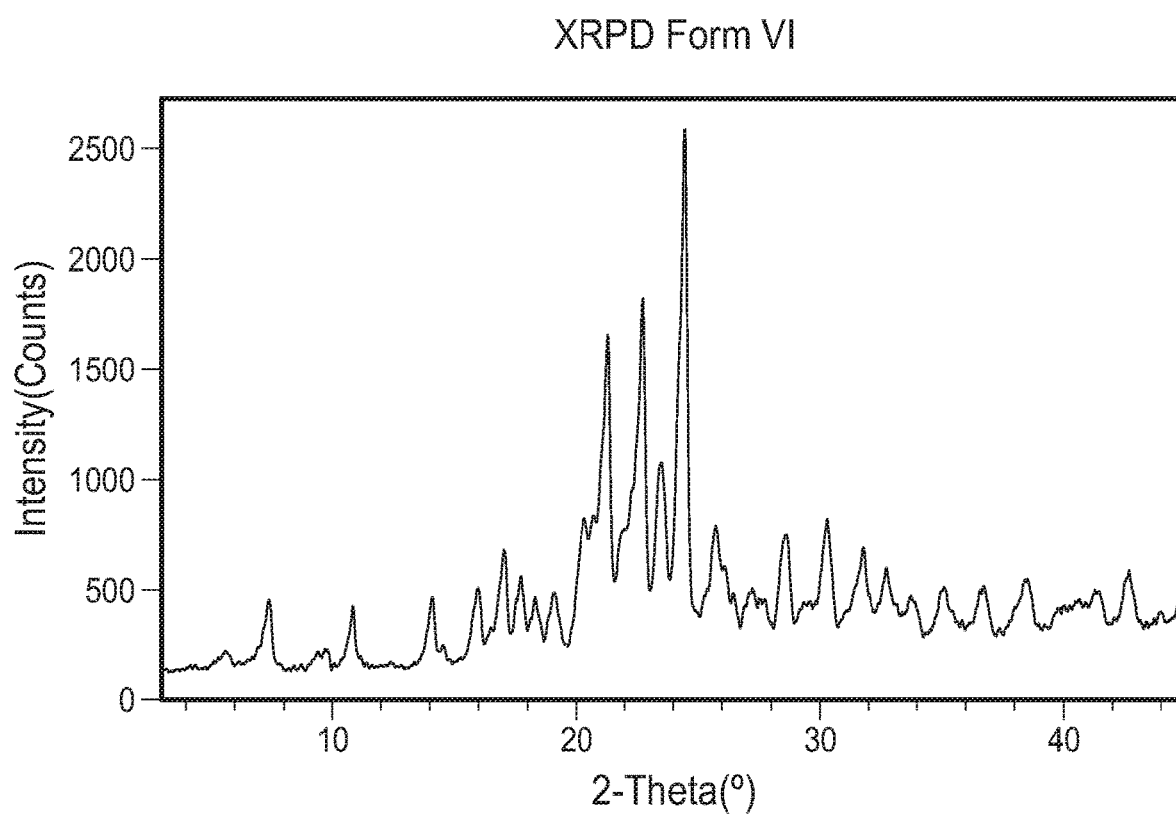
FIG. 35 shows an XRPD pattern of Compound I di-tosylate salt, Form VI.

In some embodiments, Form VI has an XRPD pattern substantially as depicted in FIG. 35.

Figure 36:
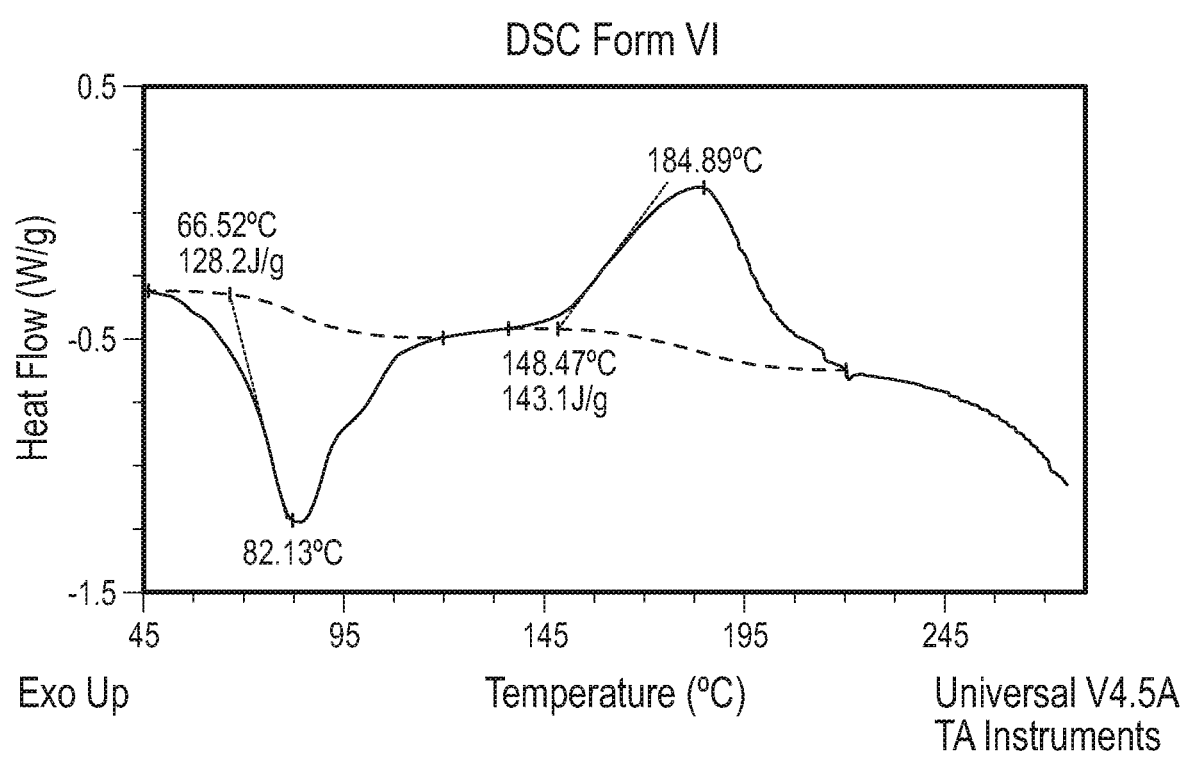
FIG. 36 shows a DSC thermogram of Compound I di-tosylate salt, Form VI.
Figure 37:
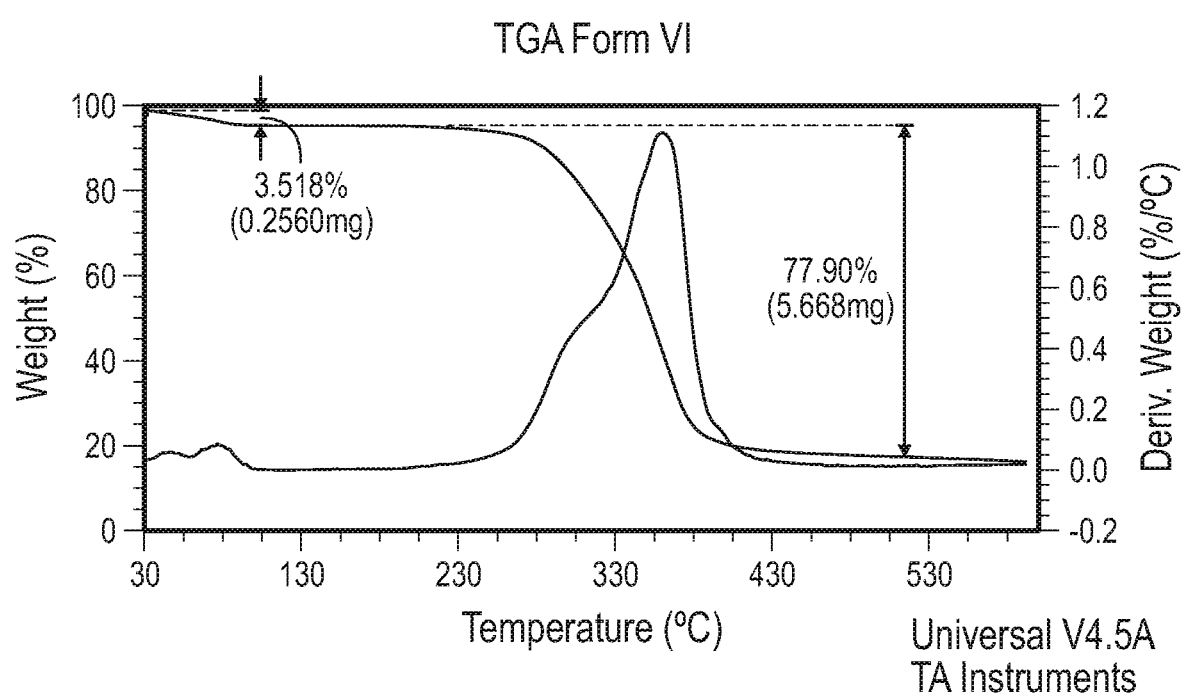
FIG. 37 shows a TGA thermogram of Compound I di-tosylate salt, Form VI.

In some embodiments, Form VI exhibits a differential scanning calorimetry thermogram having an endothermic peak at a temperature of about 82° C. In some embodiments, Form VI has an exothermic peak at a temperature of about 185° C. In some embodiments, Form VI exhibits a differential scanning calorimetry thermogram having an endothermic peak at a temperature of about 82° C. and an exothermic peak at a temperature of about 185° C. In some embodiments, Form VI has a DSC thermogram substantially as depicted in FIG. 36. In some embodiments, Form VI has a TGA thermogram substantially as depicted in FIG. 37.

Form VII of Compound I Di-Tosylate Salt

In some embodiments, the present application relates to the crystalline form of Compound I di-tosylate salt referred to as Form VII, which is described below and in the Examples.

In some embodiments, Form VII has an XRPD pattern comprising a characteristic peaks, in terms of 2-theta, selected from about 17.2, about 21.6, about 23.0, about 23.8, about 24.8, and about 26.0 degrees.

In some embodiments, Form VII has an XRPD pattern comprising two or more characteristic peaks, in terms of 2-theta, selected from about 17.2, about 21.6, about 23.0, about 23.8, about 24.8, and about 26.0 degrees.

In some embodiments, Form VII has an X-ray powder diffraction pattern comprising three or more characteristic peaks, in terms of 2-theta, selected from about 17.2, about 21.6, about 23.0, about 23.8, about 24.8, and about 26.0 degrees.

In some embodiments, Form VII has an XRPD pattern comprising four or more characteristic peaks, in terms of 2-theta, selected from about 17.2, about 21.6, about 23.0, about 23.8, about 24.8, and about 26.0 degrees.

Figure 38:
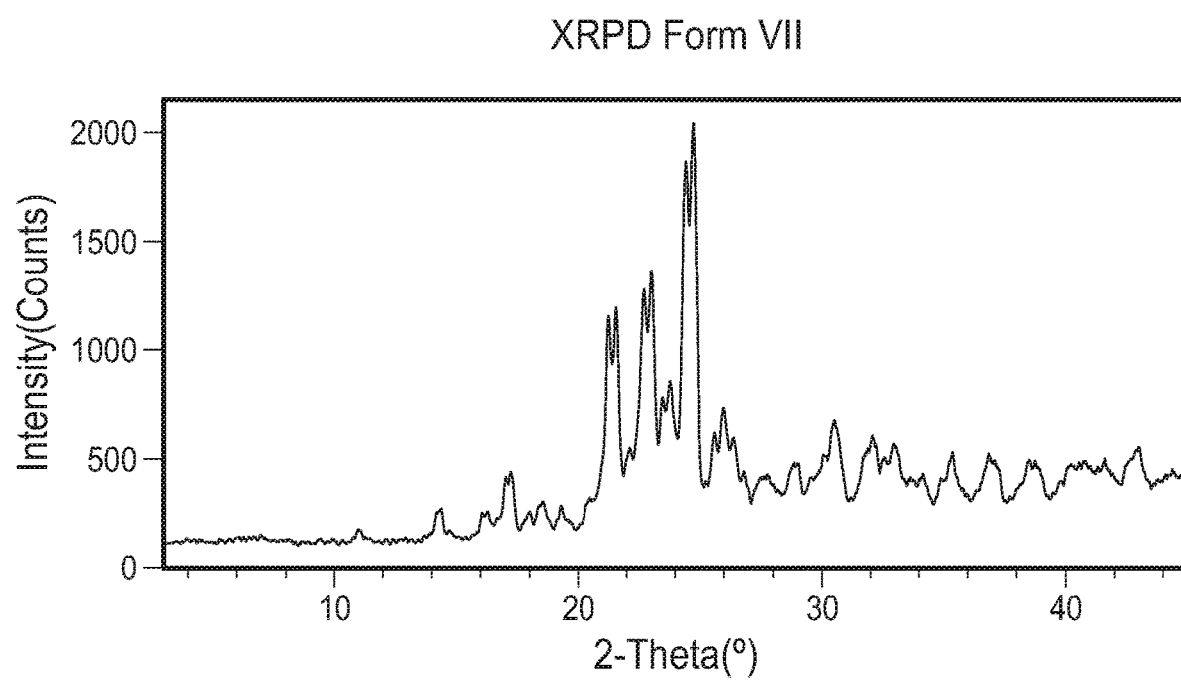
FIG. 38 shows an XRPD pattern of Compound I di-tosylate salt, Form VII.

In some embodiments, Form VII has an XRPD pattern substantially as depicted in FIG. 38.

Figure 39:
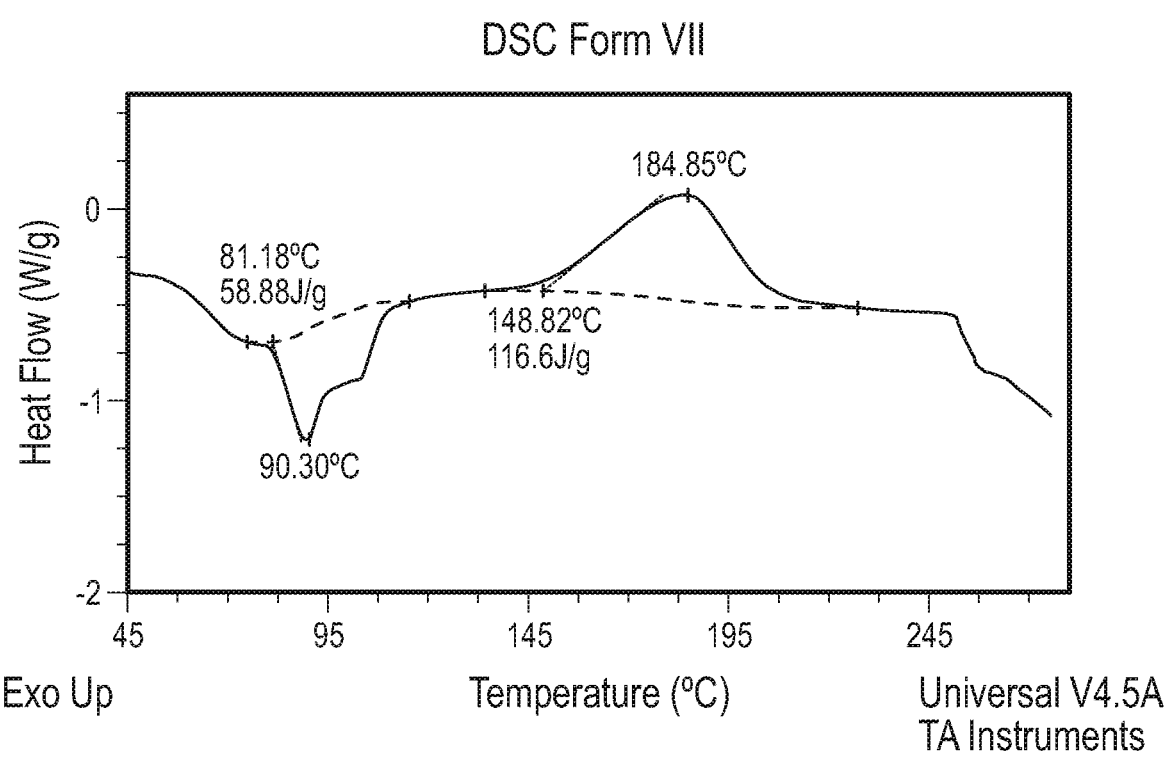
FIG. 39 shows a DSC thermogram of Compound I di-tosylate salt, Form VII.
Figure 40:
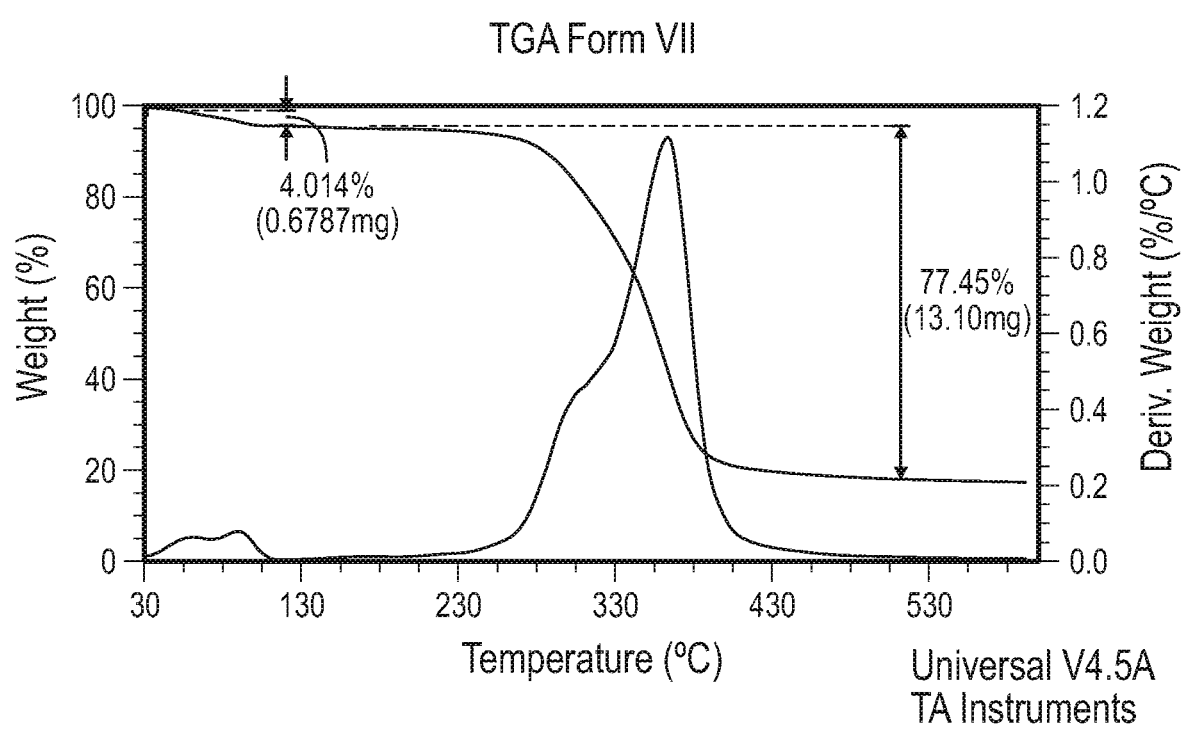
FIG. 40 shows a TGA thermogram of Compound I di-tosylate salt, Form VII.

In some embodiments, Form VII exhibits a differential scanning calorimetry thermogram having an endothermic peak at a temperature of about 90° C. In some embodiments, Form VII has an exothermic peak at a temperature of about 185° C. In some embodiments, Form VII exhibits a differential scanning calorimetry thermogram having an endothermic peak at a temperature of about 90° C. and an exothermic peak at a temperature of about 185° C. In some embodiments, Form VII has a DSC thermogram substantially as depicted in FIG. 39. In some embodiments, Form VII has a TGA thermogram substantially as depicted in FIG. 40.

Form VIII of Compound I Di-Tosylate Salt

In some embodiments, the present application relates to the crystalline form of Compound I di-tosylate salt referred to as Form VIII, which is described below and in the Examples.

In some embodiments, Form VIII has an XRPD pattern comprising a characteristic peak, in terms of 2-theta, at about 7.2 degrees. In some embodiments, Form VIII has an XRPD pattern comprising a characteristic peak, in terms of 2-theta, selected from about 7.2, about 10.6, about 14.7, and about 16.3 degrees. In some embodiments, Form VIII has an XRPD pattern comprising a characteristic peak, in terms of 2-theta, selected from about 7.2, about 10.6, about 14.7, about 16.3, and about 23.8 degrees.

In some embodiments, Form VIII has an XRPD pattern comprising two or more characteristic peaks, in terms of 2-theta, selected from about 7.2, about 10.6, about 14.7, about 16.3, and about 23.8 degrees.

In some embodiments, Form VIII has an X-ray powder diffraction pattern comprising three or more characteristic peaks, in terms of 2-theta, selected from about 7.2, about 10.6, about 14.7, about 16.3, and about 23.8 degrees.

In some embodiments, Form VIII has an XRPD pattern comprising one or more characteristic peaks, in terms of 2-theta, selected from about 7.2, about 10.6, about 14.7, about 16.3, about 17.5, about 18.1, about 20.7, about 21.5, about 22.9, about 23.8, about 24.8, and about 27.4 degrees.

In some embodiments, Form VIII has an XRPD comprising two or more characteristic peaks, in terms of 2-theta, selected from about 7.2, about 10.6, about 14.7, about 16.3, about 17.5, about 18.1, about 20.7, about 21.5, about 22.9, about 23.8, about 24.8, and about 27.4 degrees.

In some embodiments, Form VIII has an XRPD pattern comprising three or more characteristic peaks, in terms of 2-theta, selected from about 7.2, about 10.6, about 14.7, about 16.3, about 17.5, about 18.1, about 20.7, about 21.5, about 22.9, about 23.8, about 24.8, and about 27.4 degrees.

In some embodiments, Form VIII has an XRPD pattern comprising four or more characteristic peaks, in terms of 2-theta, selected from about 7.2, about 10.6, about 14.7, about 16.3, about 17.5, about 18.1, about 20.7, about 21.5, about 22.9, about 23.8, about 24.8, and about 27.4 degrees.

Figure 41:
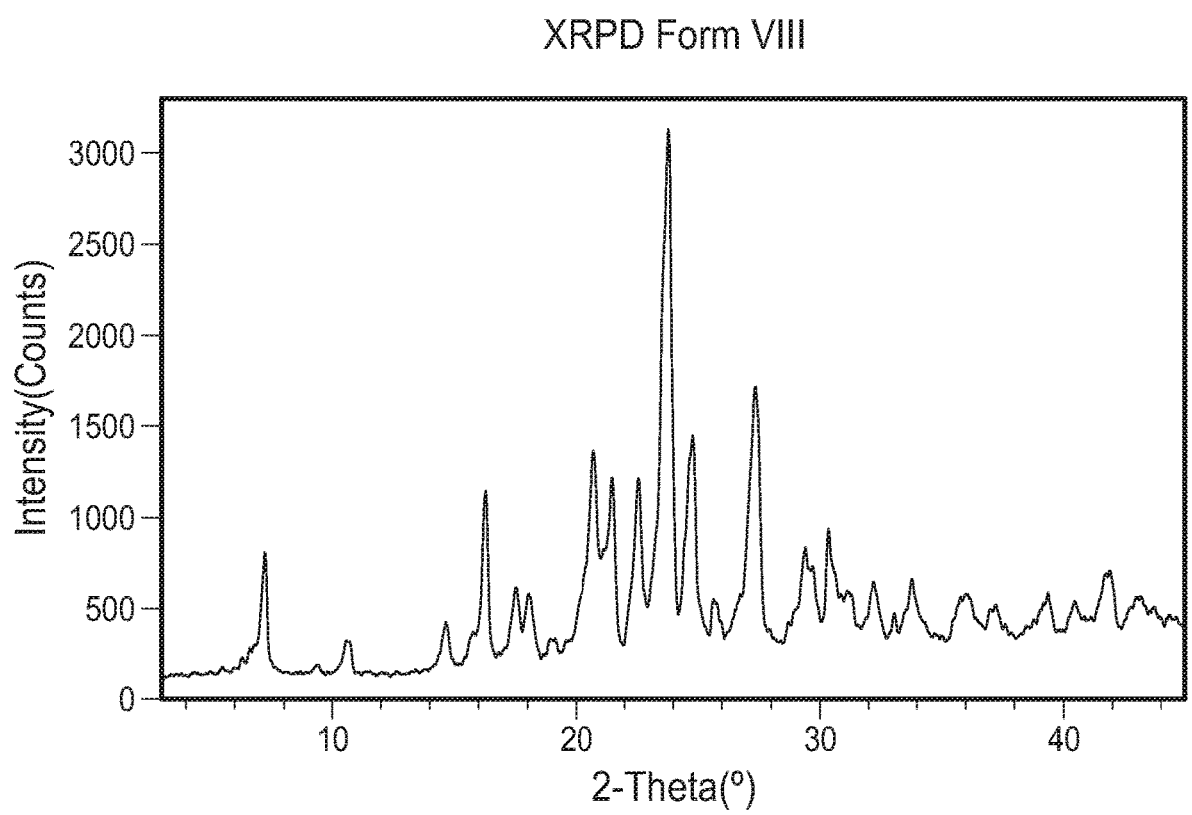
FIG. 41 shows an XRPD pattern of Compound I di-tosylate salt, Form VIII.

In some embodiments, Form VIII has an XRPD pattern substantially as depicted in FIG. 41.

Figure 42:
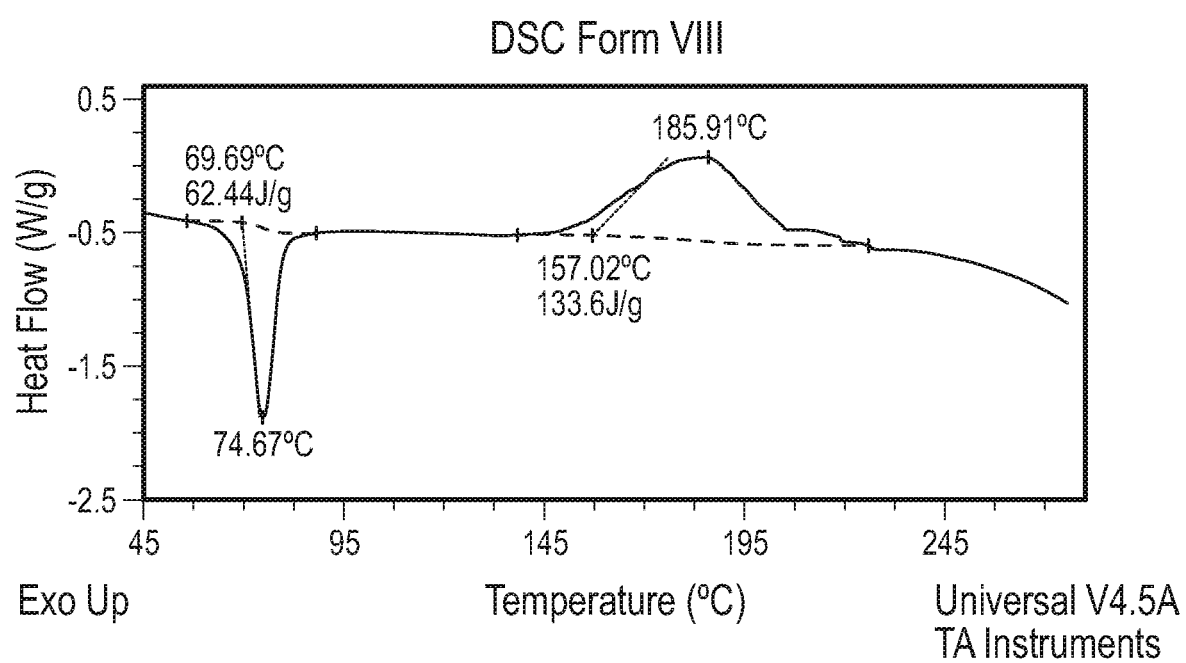
FIG. 42 shows a DSC thermogram of Compound I di-tosylate salt, Form VIII.
Figure 43:
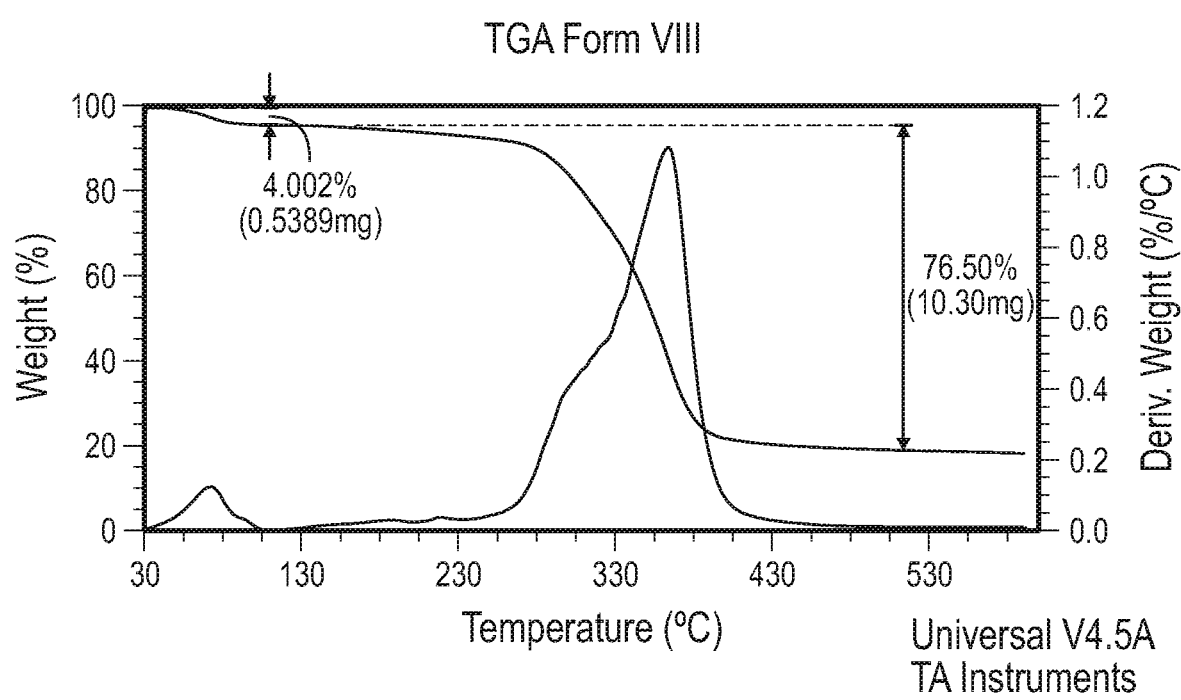
FIG. 43 shows a TGA thermogram of Compound I di-tosylate salt, Form VIII.

In some embodiments, Form VIII exhibits a differential scanning calorimetry thermogram having an endothermic peak at a temperature of about 75° C. In some embodiments, Form VIII has an exothermic peak at a temperature of about 186° C. In some embodiments, Form VIII exhibits a differential scanning calorimetry thermogram having an endothermic peak at a temperature of about 75° C. and an exothermic peak at a temperature of about 186° C. In some embodiments, Form VIII has a DSC thermogram substantially as depicted in FIG. 42. In some embodiments, Form VIII has a TGA thermogram substantially as depicted in FIG. 43.

Form IX of Compound I Di-Tosylate Salt

In some embodiments, the present application relates to the crystalline form of Compound I di-tosylate salt referred to as Form IX, which is described below and in the Examples.

In some embodiments, Form IX has an XRPD pattern comprising a characteristic peak, in terms of 2-theta, at about 5.3 degrees. In some embodiments, Form IX has an XRPD pattern comprising a characteristic peak, in terms of 2-theta, selected from about 5.3, about 10.5, about 15.7, and about 16.3 degrees.

In some embodiments, Form IX has an XRPD pattern comprising two or more characteristic peaks, in terms of 2-theta, selected from about 5.3, about 10.5, about 15.7, and about 16.3 degrees.

In some embodiments, Form IX has an X-ray powder diffraction pattern comprising three or more characteristic peaks, in terms of 2-theta, selected from about 5.3, about 10.5, about 15.7, and about 16.3 degrees.

In some embodiments, Form IX has an XRPD pattern comprising one or more characteristic peaks, in terms of 2-theta, selected from about 5.3, about 10.5, about 15.7, about 16.3, about 21.0, about 21.4, and about 26.7 degrees.

In some embodiments, Form IX has an XRPD comprising two or more characteristic peaks, in terms of 2-theta, selected from about 5.3, about 10.5, about 15.7, about 16.3, about 21.0, about 21.4, and about 26.7 degrees.

In some embodiments, Form IX has an XRPD pattern comprising three or more characteristic peaks, in terms of 2-theta, selected from about 5.3, about 10.5, about 15.7, about 16.3, about 21.0, about 21.4, and about 26.7 degrees.

In some embodiments, Form IX has an XRPD pattern comprising four or more characteristic peaks, in terms of 2-theta, selected from about 5.3, about 10.5, about 15.7, about 16.3, about 21.0, about 21.4, and about 26.7 degrees.

Figure 44:
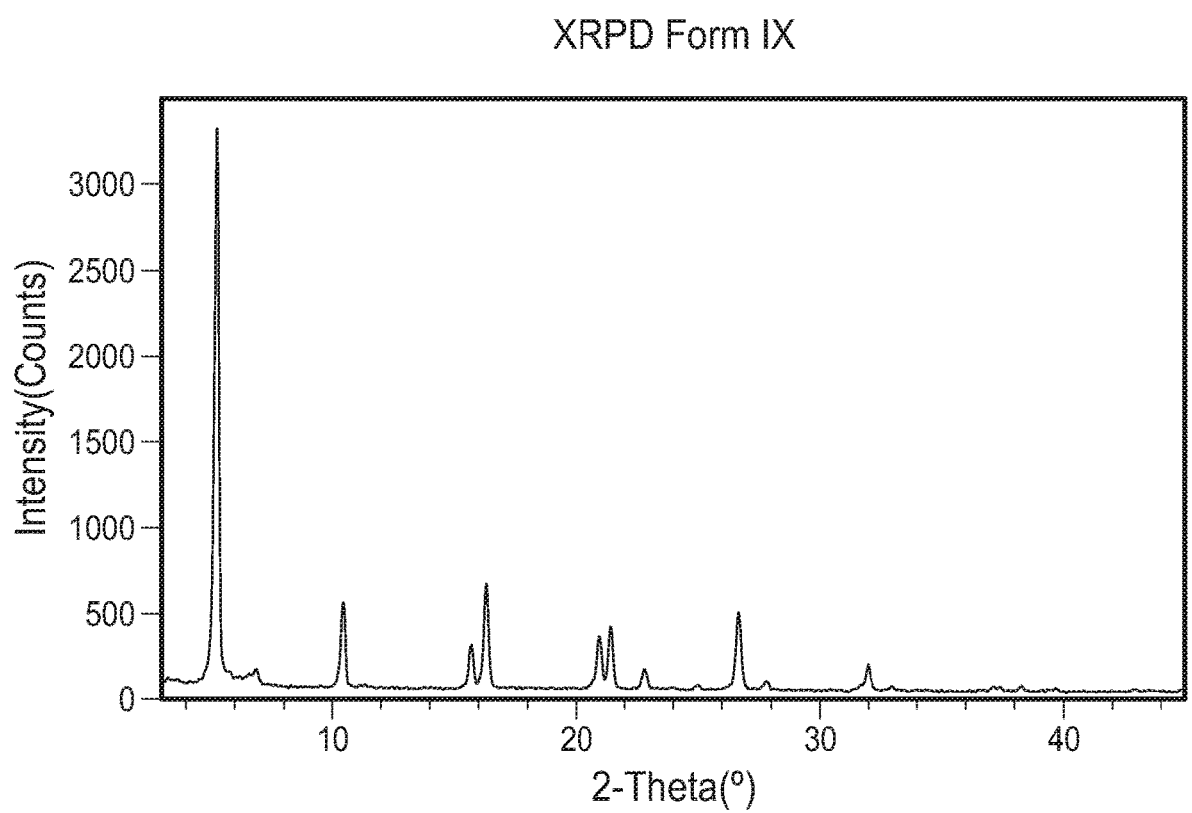
FIG. 44 shows an XRPD pattern of Compound I di-tosylate salt, Form IX.

In some embodiments, Form IX has an XRPD pattern substantially as depicted in FIG. 44.

Figure 45:
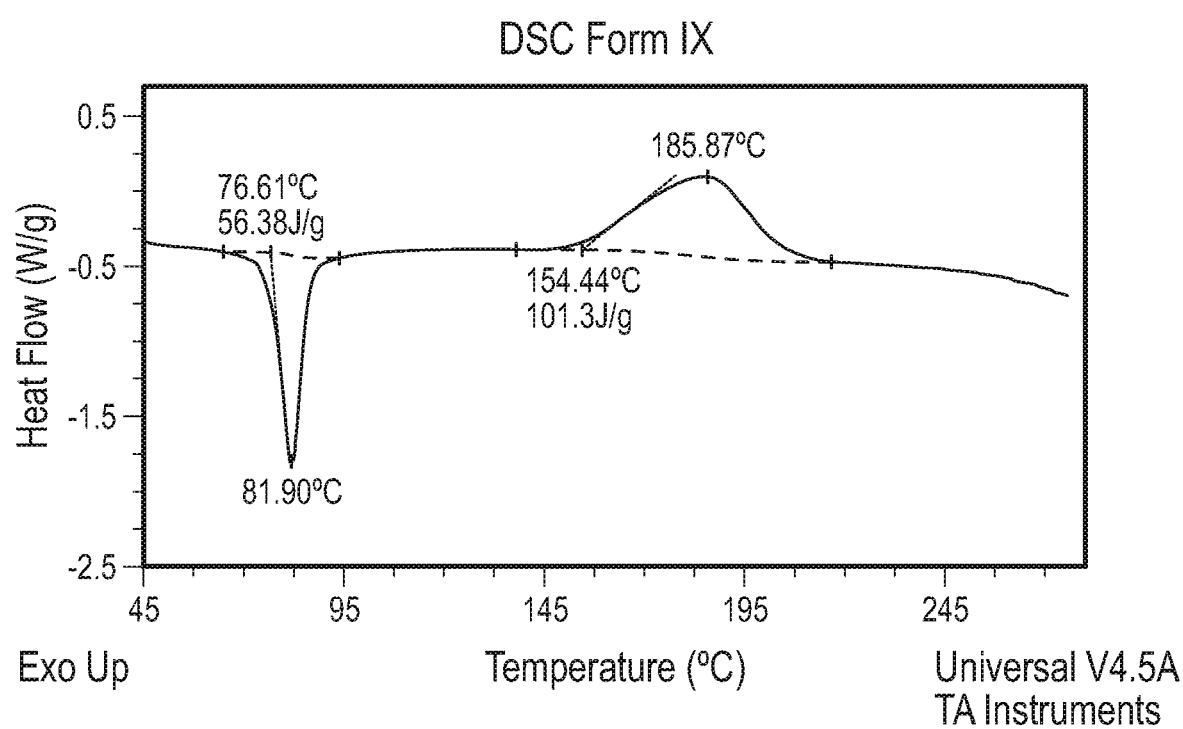
FIG. 45 shows a DSC thermogram of Compound I di-tosylate salt, Form IX.
Figure 46:
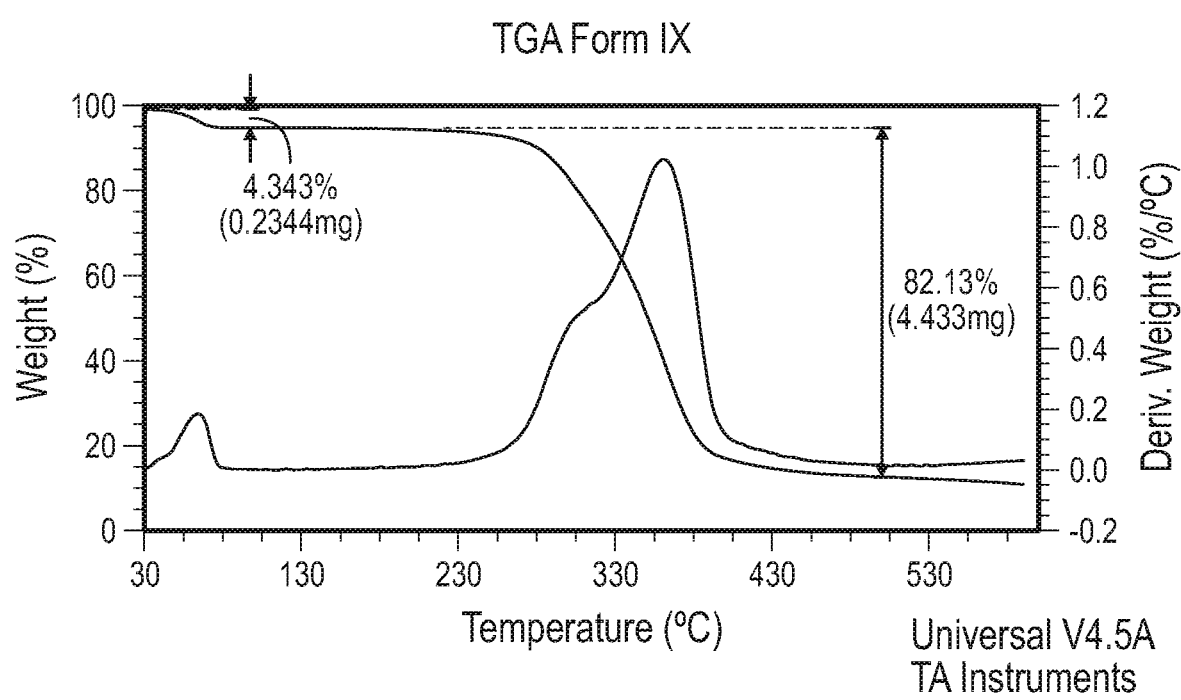
FIG. 46 shows a TGA thermogram of Compound I di-tosylate salt, Form IX.

In some embodiments, Form IX exhibits a differential scanning calorimetry thermogram having an endothermic peak at a temperature of about 82° C. In some embodiments, Form IX has an exothermic peak at a temperature of about 186° C. In some embodiments, Form IX exhibits a differential scanning calorimetry thermogram having an endothermic peak at a temperature of about 82° C. and an exothermic peak at a temperature of about 186° C. In some embodiments, Form IX has a DSC thermogram substantially as depicted in FIG. 45. In some embodiments, Form IX has a TGA thermogram substantially as depicted in FIG. 46.

Form X of Compound I Di-Tosylate Salt

In some embodiments, the present application relates to the crystalline form of Compound I di-tosylate salt referred to as Form X, which is described below and in the Examples.

In some embodiments, Form X has an XRPD pattern comprising a characteristic peak, in terms of 2-theta, selected from about 5.3, about 6.9, about 10.4, and about 14.5 degrees. In some embodiments, Form X has an XRPD pattern comprising a characteristic peak, in terms of 2-theta, selected from about 5.3, about 6.9, about 10.4, about 14.5, about 16.4, and about 18.0 degrees.

In some embodiments, Form X has an XRPD pattern comprising two or more characteristic peaks, in terms of 2-theta, selected from about 5.3, about 6.9, about 10.4, about 14.5, about 16.4, and about 18.0 degrees.

In some embodiments, Form X has an X-ray powder diffraction pattern comprising three or more characteristic peaks, in terms of 2-theta, selected from about 5.3, about 6.9, about 10.4, about 14.5, about 16.4, and about 18.0 degrees.

In some embodiments, Form X has an XRPD pattern comprising one or more characteristic peaks, in terms of 2-theta, selected from about 5.3, about 6.9, about 10.4, about 14.5, about 16.4, about 18.0, about 20.8, and about 24.0 degrees.

In some embodiments, Form X has an XRPD comprising two or more characteristic peaks, in terms of 2-theta, selected from about 5.3, about 6.9, about 10.4, about 14.5, about 16.4, about 18.0, about 20.8, and about 24.0 degrees.

In some embodiments, Form X has an XRPD pattern comprising three or more characteristic peaks, in terms of 2-theta, selected from about 5.3, about 6.9, about 10.4, about 14.5, about 16.4, about 18.0, about 20.8, and about 24.0 degrees.

In some embodiments, Form X has an XRPD pattern comprising four or more characteristic peaks, in terms of 2-theta, selected from about 5.3, about 10.5, about 15.7, about 16.3, about 21.0, about 21.4, and about 26.7 degrees.

Figure 47:
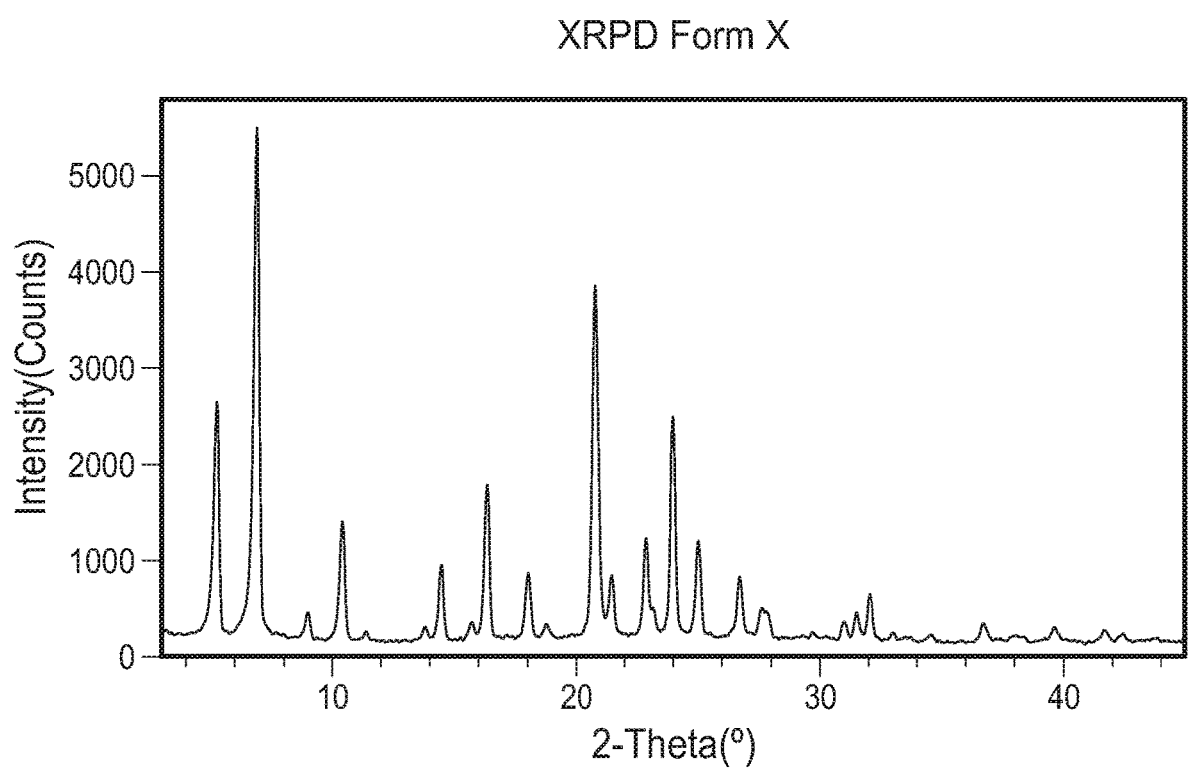
FIG. 47 shows an XRPD pattern of Compound I di-tosylate salt, Form X.

In some embodiments, Form X has an XRPD pattern substantially as depicted in FIG. 47.

Figure 48:
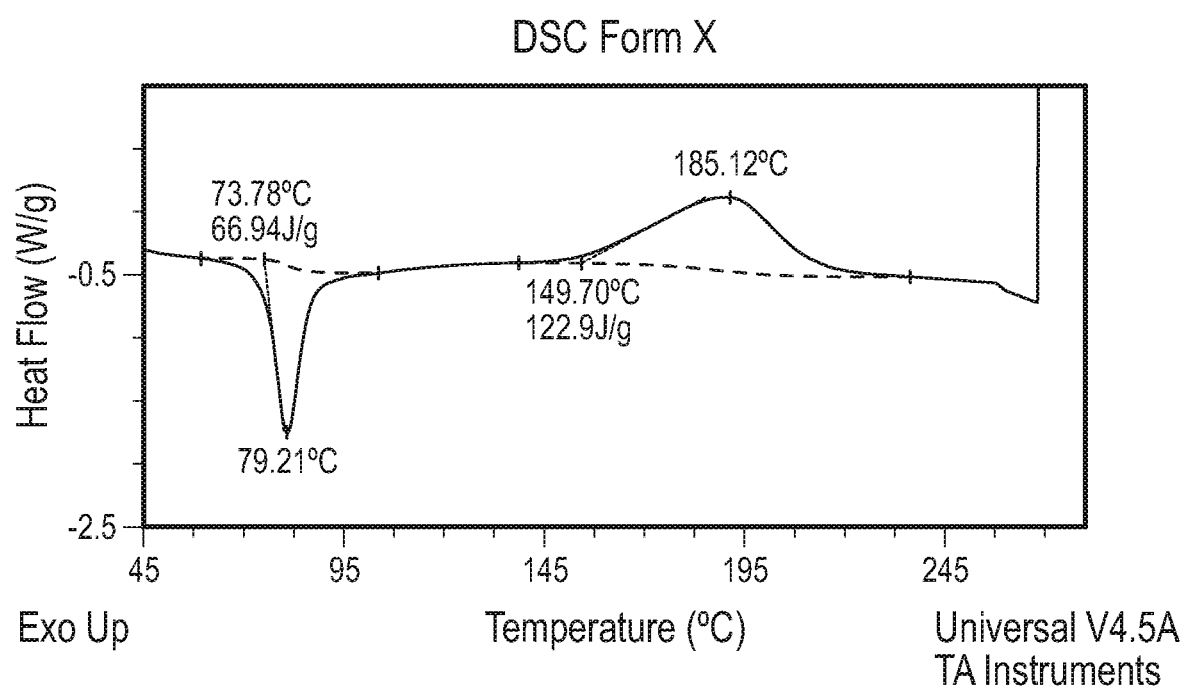
FIG. 48 shows a DSC thermogram of Compound I di-tosylate salt, Form X.
Figure 49:
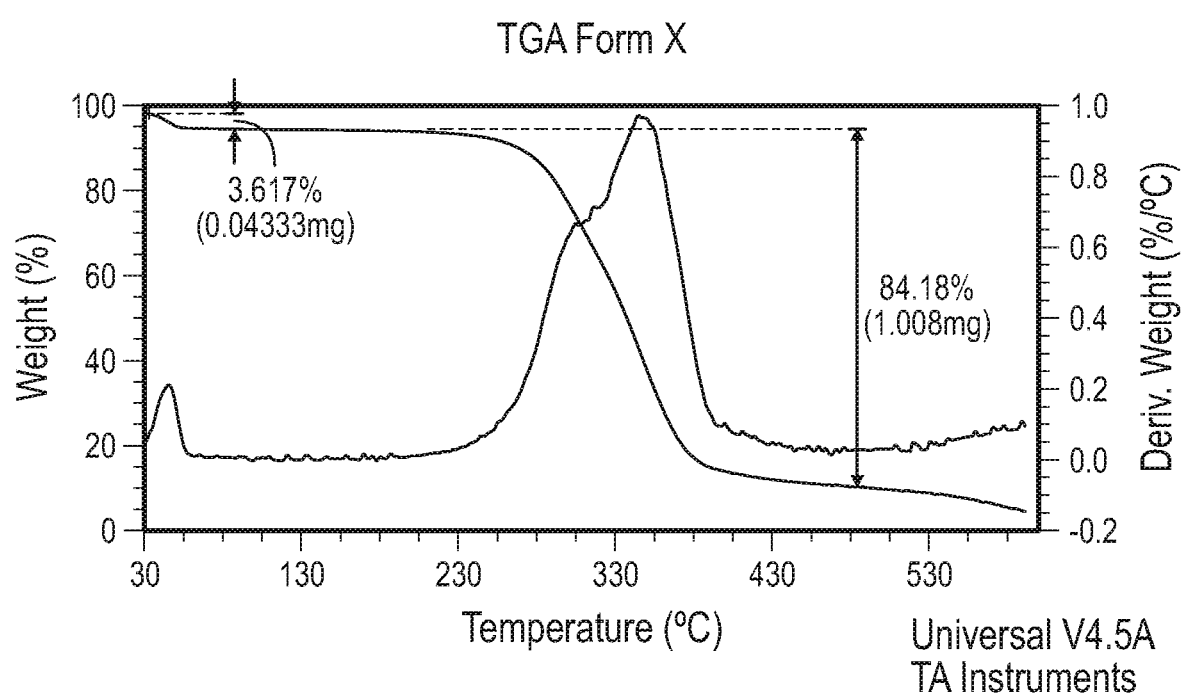
FIG. 49 shows a TGA thermogram of Compound I di-tosylate salt, Form X.

In some embodiments, Form X exhibits a differential scanning calorimetry thermogram having an endothermic peak at a temperature of about 79° C. In some embodiments, Form X has an exothermic peak at a temperature of about 185° C. In some embodiments, Form X exhibits a differential scanning calorimetry thermogram having an endothermic peak at a temperature of about 79° C. and an exothermic peak at a temperature of about 185° C. In some embodiments, Form X has a DSC thermogram substantially as depicted in FIG. 48. In some embodiments, Form X has a TGA thermogram substantially as depicted in FIG. 49.

Form XI of Compound I Di-Tosylate Salt

In some embodiments, the present application relates to the crystalline form of Compound I di-tosylate salt referred to as Form XI, which is described below and in the Examples.

In some embodiments, Form XI has an XRPD pattern comprising a characteristic peak, in terms of 2-theta, at about 5.4 degrees. In some embodiments, Form XI has an XRPD pattern comprising a characteristic peak, in terms of 2-theta, selected from about 5.4, about 6.7, about 15.5, about 16.1, and about 20.7 degrees.

In some embodiments, Form XI has an XRPD pattern comprising two or more characteristic peaks, in terms of 2-theta, selected from about 5.4, about 6.7, about 15.5, about 16.1, and about 20.7 degrees.

In some embodiments, Form XI has an X-ray powder diffraction pattern comprising three or more characteristic peaks, in terms of 2-theta, selected from about 5.4, about 6.7, about 15.5, about 16.1, and about 20.7 degrees.

In some embodiments, Form XI has an XRPD pattern comprising one or more characteristic peaks, in terms of 2-theta, selected from about 5.4, about 6.7, about 15.5, about 16.1, about 20.7, about 21.1, about 22.5, and about 23.4 degrees.

In some embodiments, Form XI has an XRPD comprising two or more characteristic peaks, in terms of 2-theta, selected from about 5.4, about 6.7, about 15.5, about 16.1, about 20.7, about 21.1, about 22.5, and about 23.4 degrees.

In some embodiments, Form XI has an XRPD pattern comprising three or more characteristic peaks, in terms of 2-theta, selected from about 5.4, about 6.7, about 15.5, about 16.1, about 20.7, about 21.1, about 22.5, and about 23.4 degrees.

In some embodiments, Form XI has an XRPD pattern comprising four or more characteristic peaks, in terms of 2-theta, selected from about 5.4, about 6.7, about 15.5, about 16.1, about 20.7, about 21.1, about 22.5, and about 23.4 degrees.

Figure 50:
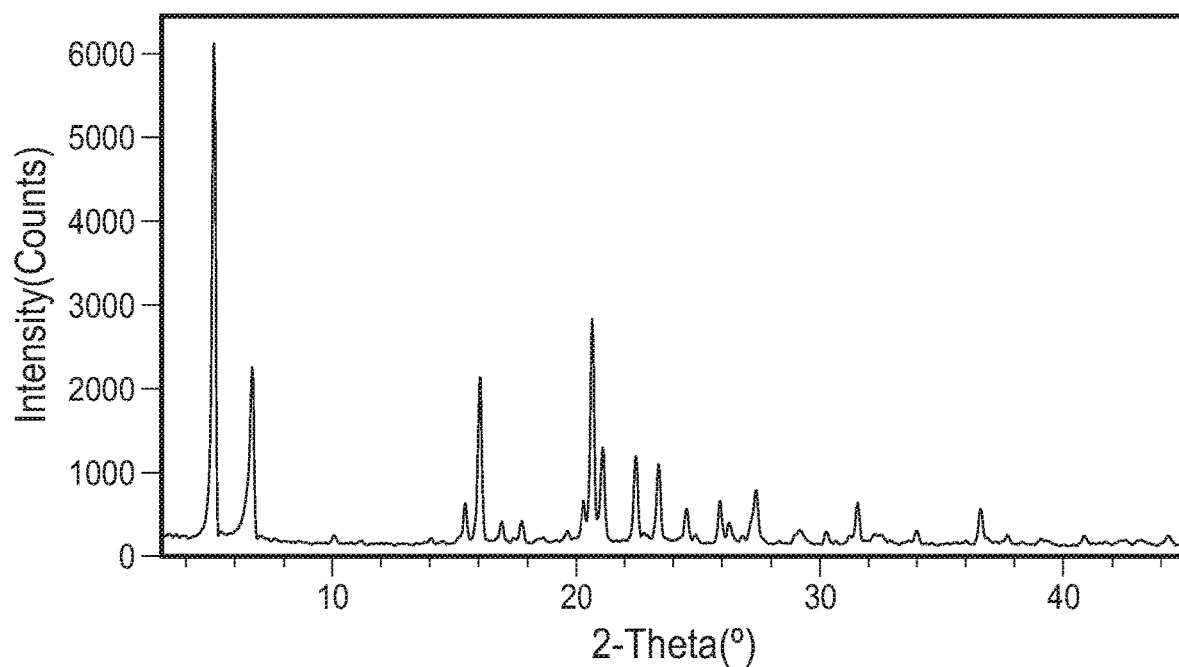
FIG. 50 shows an XRPD pattern of Compound I di-tosylate salt, Form XI.

In some embodiments, Form XI has an XRPD pattern substantially as depicted in FIG. 50.

Figure 51:
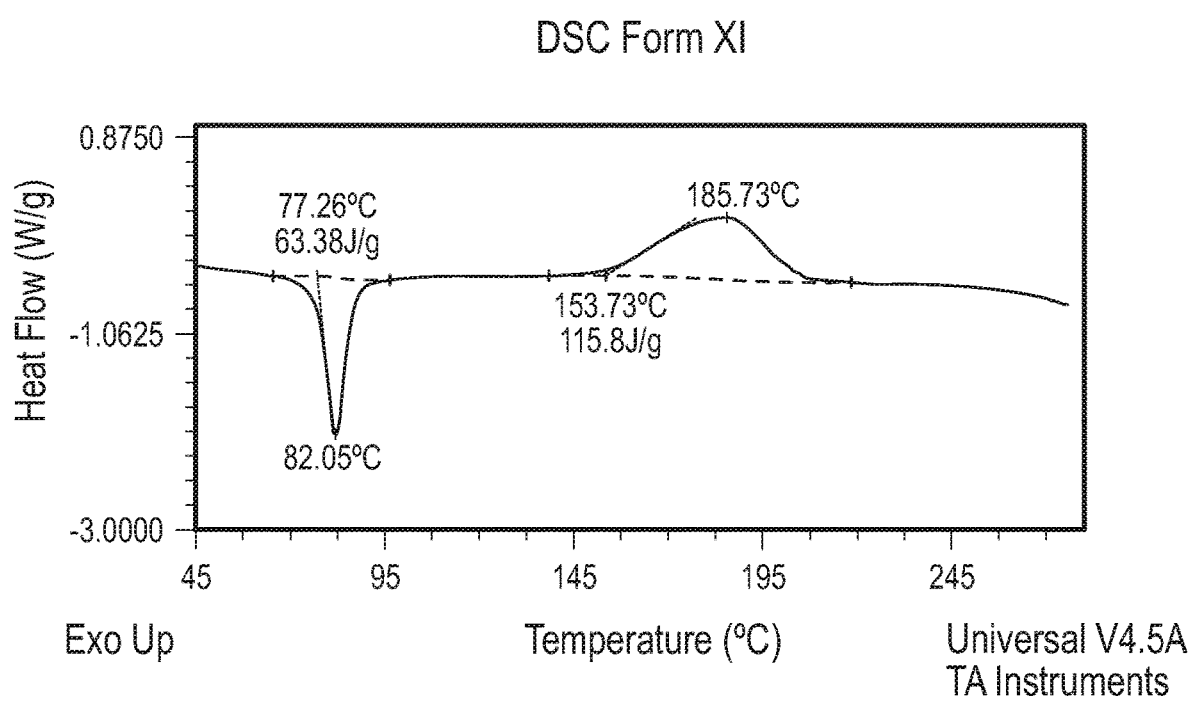
FIG. 51 shows a DSC thermogram of Compound I di-tosylate salt, Form XI.
Figure 52:
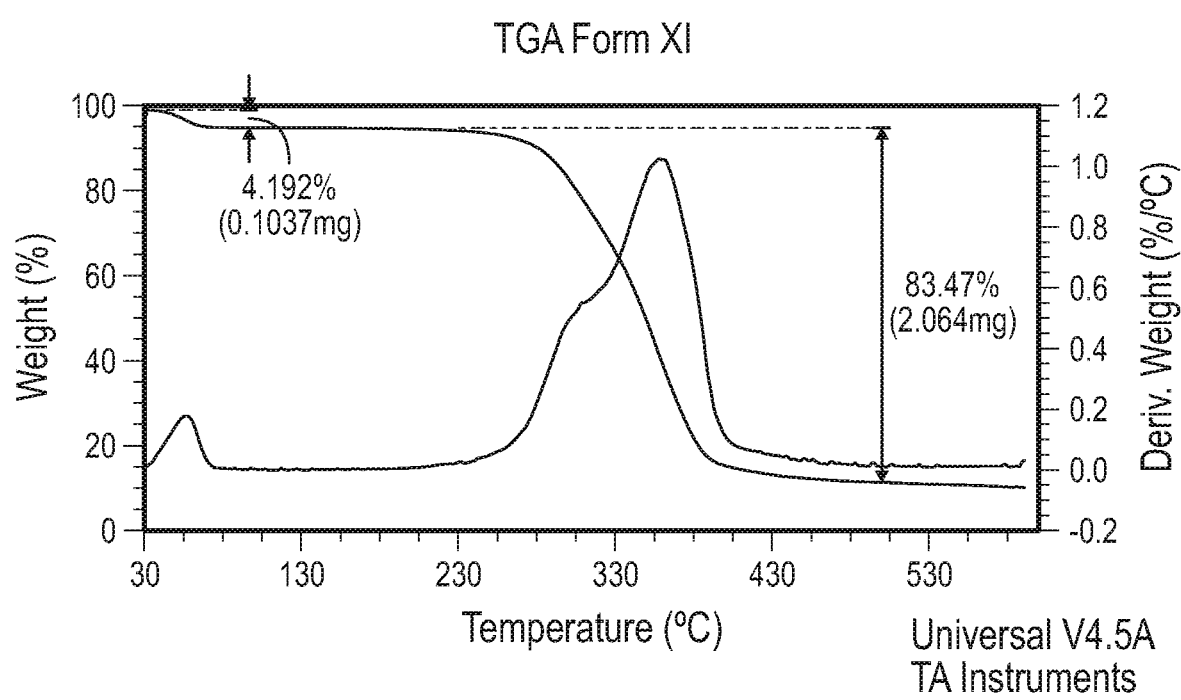
FIG. 52 shows a TGA thermogram of Compound I di-tosylate salt, Form XI.

In some embodiments, Form XI exhibits a differential scanning calorimetry thermogram having an endothermic peak at a temperature of about 82° C. In some embodiments, Form XI has an exothermic peak at a temperature of about 186° C. In some embodiments, Form XI exhibits a differential scanning calorimetry thermogram having an endothermic peak at a temperature of about 82° C. and an exothermic peak at a temperature of about 186° C. In some embodiments, Form XI has a DSC thermogram substantially as depicted in FIG. 51. In some embodiments, Form XI has a TGA thermogram substantially as depicted in FIG. 52.

Form XII of Compound I Di-Tosylate Salt

In some embodiments, the present application relates to the crystalline form of Compound I di-tosylate salt referred to as Form XII, which is described below and in the Examples.

In some embodiments, Form XII has an XRPD pattern comprising a characteristic peak, in terms of 2-theta, selected from about 5.1 and about 6.8 degrees. In some embodiments, Form XII has an XRPD pattern comprising a characteristic peak, in terms of 2-theta, selected from about 5.1, about 6.8, about 8.8, about 10.2, about 9.2, and about 13.5 degrees. In some embodiments, Form XII has an XRPD pattern comprising a characteristic peak, in terms of 2-theta, selected from about 5.1, about 6.8, about 8.8, about 9.2, about 10.2, about 13.5, about 15.4, about 16.5, and about 17.2 degrees.

In some embodiments, Form XII has an XRPD pattern comprising two or more characteristic peaks, in terms of 2-theta, selected from about 5.1, about 6.8, about 8.8, about 9.2, about 10.2, about 13.5, about 15.4, about 16.5, and about 17.2 degrees.

In some embodiments, Form XII has an X-ray powder diffraction pattern comprising three or more characteristic peaks, in terms of 2-theta, selected from about 5.1, about 6.8, about 8.8, about 9.2, about 10.2, about 13.5, about 15.4, about 16.5, and about 17.2 degrees.

In some embodiments, Form XII has an XRPD pattern comprising one or more characteristic peaks, in terms of 2-theta, selected from about 5.1, about 6.8, about 8.8, about 9.2, about 10.2, about 13.5, about 15.4, about 16.5, about 17.2, about 20.8, about 22.1, and about 23.9 degrees.

In some embodiments, Form XII has an XRPD comprising two or more characteristic peaks, in terms of 2-theta, selected from about 5.1, about 6.8, about 8.8, about 9.2, about 10.2, about 13.5, about 15.4, about 16.5, about 17.2, about 20.8, about 22.1, and about 23.9 degrees.

In some embodiments, Form XII has an XRPD pattern comprising three or more characteristic peaks, in terms of 2-theta, selected from about 5.1, about 6.8, about 8.8, about 9.2, about 10.2, about 13.5, about 15.4, about 16.5, about 17.2, about 20.8, about 22.1, and about 23.9 degrees.

In some embodiments, Form XII has an XRPD pattern comprising four or more characteristic peaks, in terms of 2-theta, selected from about 5.1, about 6.8, about 8.8, about 9.2, about 10.2, about 13.5, about 15.4, about 16.5, about 17.2, about 20.8, about 22.1, and about 23.9 degrees.

Figure 53:
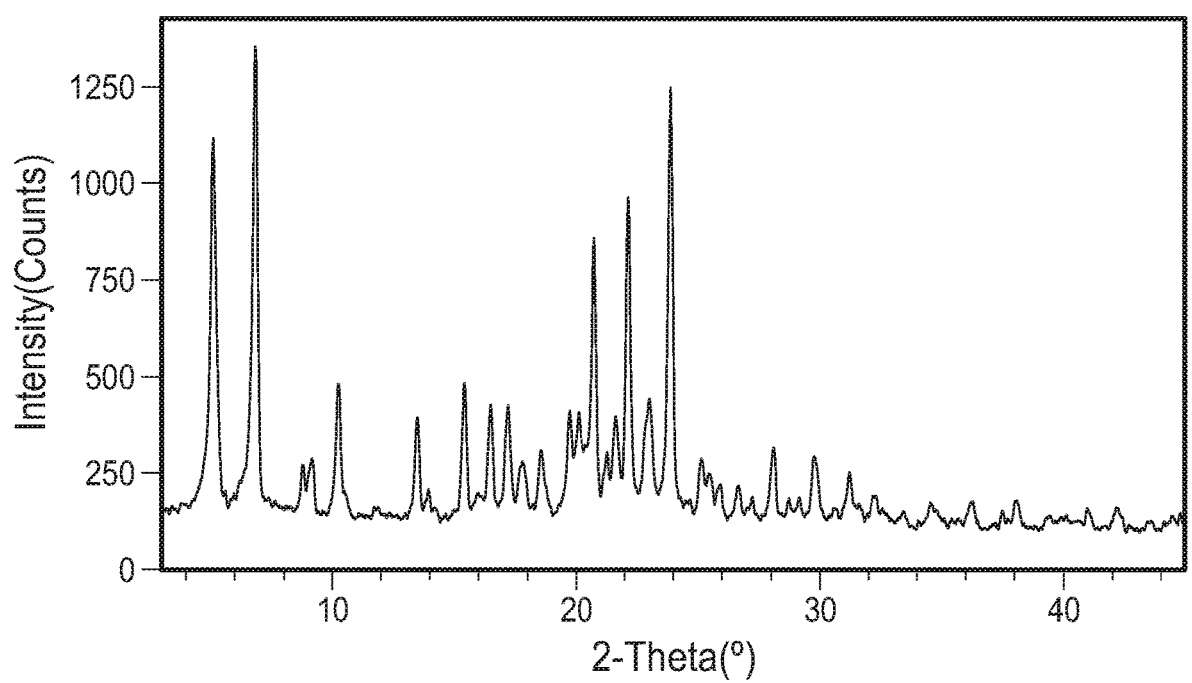
FIG. 53 shows an XRPD pattern of Compound I di-tosylate salt, Form XII.

In some embodiments, Form XII has an XRPD pattern substantially as depicted in FIG. 53.

Figure 54:
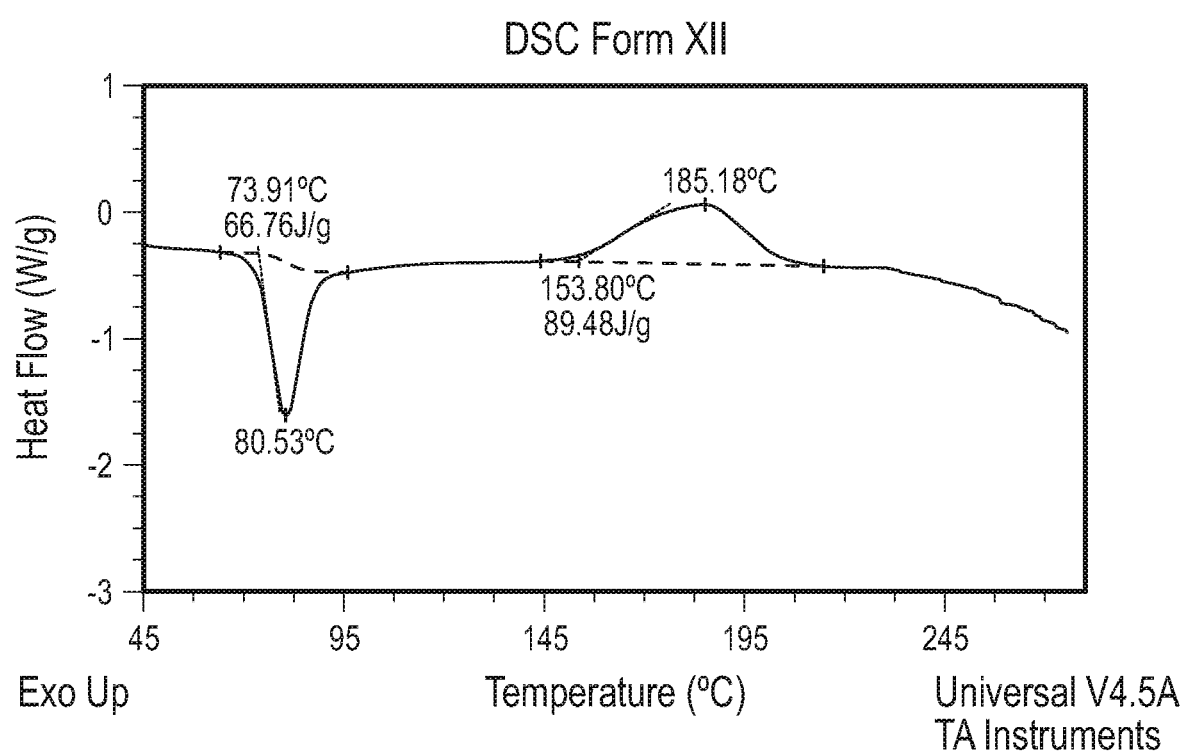
FIG. 54 shows a DSC thermogram of Compound I di-tosylate salt, Form XII.
Figure 55:
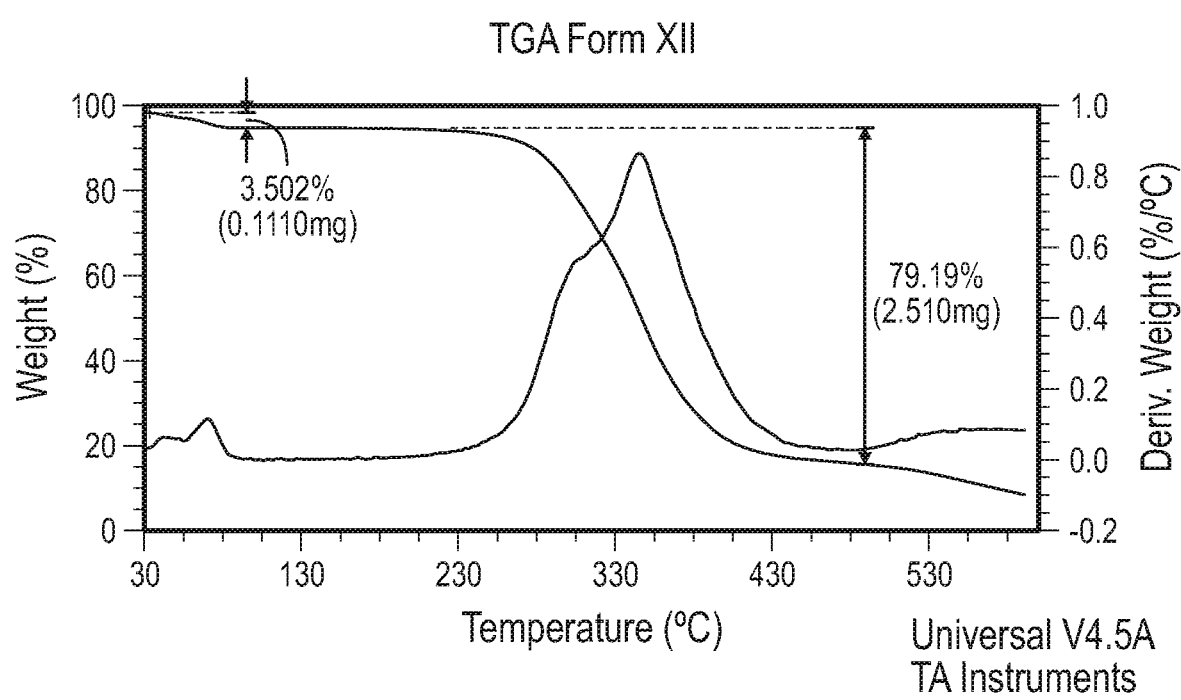
FIG. 55 shows a TGA thermogram of Compound I di-tosylate salt, Form XII.

In some embodiments, Form XII exhibits a differential scanning calorimetry thermogram having an endothermic peak at a temperature of about 81° C. In some embodiments, Form XI has an exothermic peak at a temperature of about 186° C. In some embodiments, Form XII exhibits a differential scanning calorimetry thermogram having an endothermic peak at a temperature of about 81° C. and an exothermic peak at a temperature of about 186° C. In some embodiments, Form XI has a DSC thermogram substantially as depicted in FIG. 54. In some embodiments, Form XI has a TGA thermogram substantially as depicted in FIG. 55.

The salts and compounds disclosed herein can include all isotopes of atoms occurring in the intermediate or final compounds or salts. Isotopes include those atoms having the same atomic number but different mass numbers. For example, isotopes of hydrogen include tritium and deuterium. One or more constituent atoms of the salts or compounds of the invention can be replaced or substituted with isotopes of the atoms in natural or non-natural abundance. In some embodiments, the salt or compound includes at least one deuterium atom. For example, one or more hydrogen atoms in a salt or compound of the present disclosure can be replaced or substituted by deuterium atoms. In some embodiments, the salt or compound includes two or more deuterium atoms. In some embodiments, the salt or compound includes 1, 2, 3, 4, 5, 6, 7 or 8 deuterium atoms. In some embodiments, the hydrogen atoms in ditosylate salt or compound I as described herein can be replaced or substituted by 1 to 32 deuterium atoms. In some embodiments, the hydrogen atoms on the cyclopropyl group in Compound I can be replaced or substituted with 1, 2, 3 or 4 deuterium atoms. In some embodiments, all the hydrogen atoms on the phenyl group in Compound I can be replaced or substituted with deuterium atoms. In some embodiments, the hydrogen atoms on the —CH$_2$— linkage between the piperidine and the NH moieties in Compound I can be replaced or substituted with 1 or 2 deuterium atoms. In some embodiments, the hydrogen atoms on the methoxymethyl group in Compound I can be replaced or substituted with 1 to 5 deuterium atoms. In some embodiments, the hydrogen atoms on the cyclobutyl and/or the piperidine ring in Compound I can be replaced or substituted by 1 to 14 deuterium atoms. Synthetic methods for including isotopes into organic compounds are known in the art.

All salts and compounds described herein can be found together with other substances such as water and solvents (e.g., hydrates and solvates) or can be isolated. When in the solid state, the salts and compounds described herein may occur in various forms and may, e.g., take the form of solvates, including hydrates.

In some embodiments, the salts or crystalline forms of the invention are substantially isolated. By "substantially isolated" is meant that the salt or crystalline form is at least partially or substantially separated from the environment in which it was formed or detected. Partial separation can include, e.g., a composition enriched in the salts or crystalline forms of the invention. Substantial separation can include compositions containing at least about 50%, at least about 60%, at least about 70%, at least about 80%, at least about 90%, at least about 95%, at least about 97%, or at least about 99% by weight of the salts or crystalline forms of the invention.

Synthetic Preparation

In another aspect, the present disclosure provides methods for preparing the di-tosylate salt of Compound I, i.e. 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate). The method includes reacting 1-{[4-({(tert-butoxycarbonyl)[(1R,2S)-2-phenylcyclopropyl]amino}methyl)-4-(methoxymethyl)piperidin-1-yl]methyl}cyclobutanecarboxylic acid (11) having the formula:

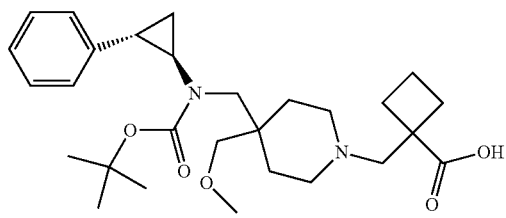

11 with p-toluenesulfonic acid (TsOH) in a solvent under conditions sufficient to form 1-{[4-(methoxymethyl)-4-({[(1R,2 S)-2-phenylcyclopropyl]amino methyl)piperidin-1-yl]methyl}cyclobutanecarboxylic acid bis(4-methylbenzenesulfonate). In some embodiments, at least about 2 molar equivalents of p-toluenesulfonic acid is used in the reaction, with respect to the amount of compound (11). Suitable solvents for carrying out the reaction include, but are not limited to, THF, dioxane, dimethylformamide, 2-methyl-THF, acetone, methyl t-butyl ether, water, 2-butanone and combinations thereof. In one embodiment, the reaction is carried out in THF. In some embodiments, the method can include a further step of recrystallization of 1-{[4-(methoxymethyl)-4-({[(1R,2 S)-2-phenylcyclopropyl] amino}methyl)piperidin-1-yl] methyl}cyclobutanecarboxylic acid bis(4-methylbenzenesulfonate). Suitable solvents for recrystallization include, but are not limited to, THF, 2-methyl-THF, hexane/2-butanone, heptane/2-butanone, dimethylformamide, acetone, acetonitrile and combinations thereof. In one embodiment, the recrystallization is carried out in mixed solvents of heptane and 2-butanone. The reaction is generally carried out at a temperature range of about 50 to 60° C. or 55 to 60° C. In one embodiment, the reaction is carried at about 55° C.

The present disclosure further provides a method for preparing compound (11). The method includes reacting compound (10) benzyl 1-{[4-({(tert-butoxycarbonyl)[(1R,2S)-2-phenylcyclopropyl]amino}methyl)-4-(methoxymethyl)piperidin-1-yl]methyl}cyclobutanecarboxylate having the formula:

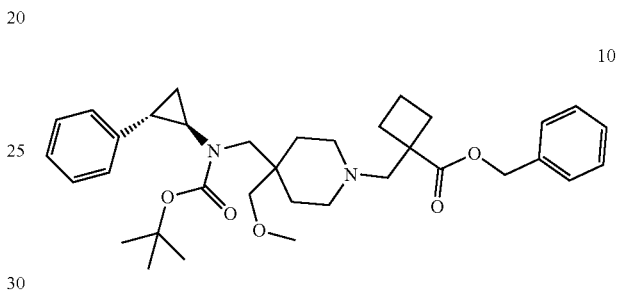

10 with a base such as KOH, NaOH, LiOH, or CsOH in a solvent such as ethanol or a mixture of water/ethanol. In some embodiments, the base is employed to hydrolyze the benzyl ester moiety in Compound 10. In one embodiment, the reaction is carried out at 40° C. In some embodiments, once the hydrolysis reaction is complete, an acid (such as HCl, e.g., aqueous HCl) is added to the reaction mixture to neutralize the mixture.

In some embodiments, the present disclosure provides a method for preparing compound (10). The method includes reacting benzyl 1-((4-(methoxymethyl)-4-(((1R,2S)-2-phenylcyclopropylamino)methyl)piperidin-1-yl)methyl)cyclobutanecarboxylate (9)

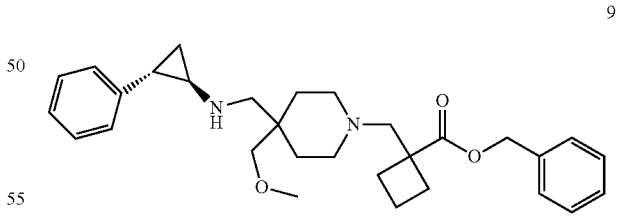

9 with di-t-butyl dicarbonate in a solvent such as dichloromethane to form 1-{[4-({(tert-butoxycarbonyl)[(1R,2S)-2-phenylcyclopropyl]amino}methyl)-4-methoxymethyl)piperidin-1-yl]methyl}cyclobutanecarboxylic acid.

Compound (10) can be purified. For example, the purification includes reacting compound (10) with L-tartaric acid to form compound (10) L-tartrate:

(10 L-tartrate)

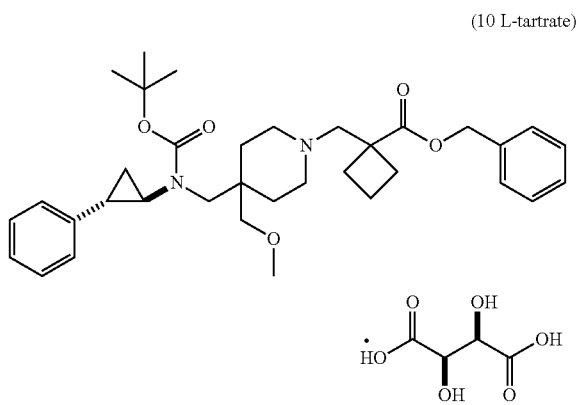

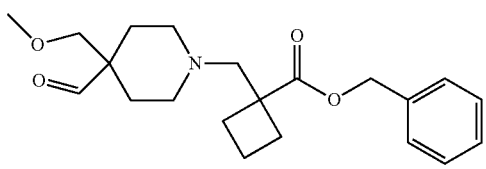

optionally in the presence of one or more solvents (e.g., isopropanol, methanol, and n-heptane); and reacting compound (10) L-tartrate with NaHCO₃ to form purified compound (10) optionally in the presence of a solvent (e.g., dichloromethane). L-tartaric acid can form a crystalline salt with compound 10, which is effective in removing impurities in compound 10. In some embodiments, after said purification process, the purity of compound 10 is greater than about 99% as compared to the purity of compound 10 without undergoing said purification process, which can range from about 90% to about 95%.

In some embodiments, the present disclosure provides a method for preparing compound (9). The method includes dissolving benzyl 1-{[4-formyl-4-(methoxymethyl)piperidin-1-yl]methyl}cyclobutanecarboxylate (7) having the formula:

(7)

and (1R,2S)-2-phenylcyclopropanamine (8) in a solvent such as dichloromethane to form a mixture; and reacting the mixture with a reducing agent in a solvent under conditions sufficient to form compound (9). Suitable reducing agents include, but are not limited to, NaBH(OAc)₃, NaBH₄, LiAlH₄, diisobutylaluminium hydride, lithium triethylborohydride, sodium bis(2-methoxyethoxy)aluminumhydride, and sodium cyanoborohydride. Suitable solvents include, but are not limited to, dichloromethane, THF, hexane, benzene, ether, methanol, acetic acid, acetonitrile or combinations thereof. In one embodiment, the solvent is dichloromethane or a mixture of dichloromethane and acetic acid.

In another aspect, the present disclosure provides synthetic intermediates that are useful for the synthesis of tosylate salts of Compound I. In some embodiments, the present disclosure provides a synthetic intermediate having Formula (II):

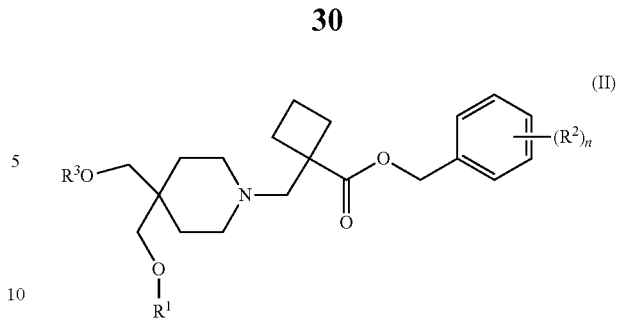

where $R^1$ is $C_{1-6}$ alkyl or $C_{1-6}$ haloalkyl; $R^2$ is halo, CN, $C_{1-6}$ alkyl, $C_{1-6}$ alkoxy, $C_{1-4}$ haloalkyl, or $C_{1-4}$ haloalkoxy; $R^3$ is H or a labile group; and the subscript n is 0, 1, 2 or 3. In some embodiments of compounds of formula (II), $R^1$ is CH₃. In other embodiments of compounds of formula (II), n is 0. In other embodiments of compounds of formula (II), $R^3$ is H, p-toluenesulfonyl, methanesulfonyl or trifluoromethanesulfonyl. In other embodiments of compounds of formula (II), $R^3$ is H. In one embodiment of compounds of formula (II), $R^1$ is CH₃, n is 0 and $R^3$ is H.

In some embodiments, the present disclosure provides a synthetic intermediate having Formula (III):

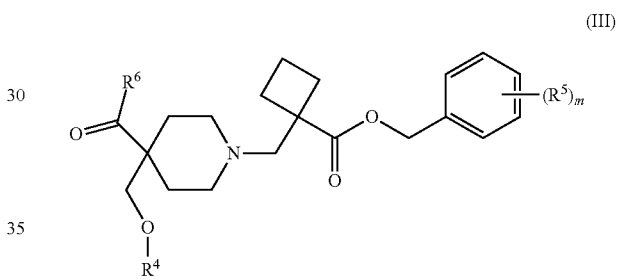

where $R^4$ is $C_{1-6}$ alkyl or $C_{1-6}$ haloalkyl; $R^5$ is halo, CN, $C_{1-6}$ alkyl, $C_{1-6}$ alkoxy, $C_{1-4}$ haloalkyl, or $C_{1-4}$ haloalkoxy; $R^6$ is H or halo; and the subscript m is 0, 1, 2 or 3. In some embodiments of compounds of formula (III), $R^4$ is CH₃. In some embodiments of compounds of formula (III), m is 0. In some embodiments of compounds of formula (III), $R^6$ is H, Cl or Br. In some embodiments of compounds of formula (III), $R^6$ is H. In one embodiment of compounds of formula (III), $R^4$ is CH₃, $R^6$ is H and m is 0.

In some embodiments, the present disclosure provides a synthetic intermediate having Formula (IV):

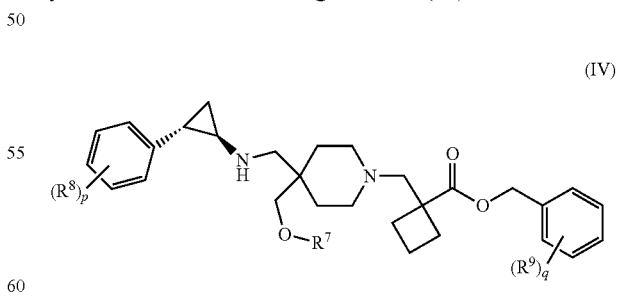

where $R^7$ is $C_{1-6}$ alkyl or $C_{1-6}$ haloalkyl; $R^8$ is halo, CN, $C_{1-6}$ alkyl, $C_{1-6}$ alkoxy, $C_{1-4}$ haloalkyl, or $C_{1-4}$ haloalkoxy; $R^9$ is halo, CN, $C_{1-6}$ alkyl, $C_{1-6}$ alkoxy, $C_{1-4}$ haloalkyl, or $C_{1-4}$ haloalkoxy; the subscript p is 0, 1, 2 or 3; and the subscript q is 0, 1, 2 or 3. In some embodiments of compounds of formula (IV), $R^7$ is CH₃. In some embodiments of compounds of formula (IV), p is 0. In some embodiments of compounds of formula (IV), q is 0. In some embodiments of compounds of formula (IV), R$^7$ is CH$_3$, p is 0 and q is 0.

In some embodiments, the present disclosure provides a synthetic intermediate having Formula (V):

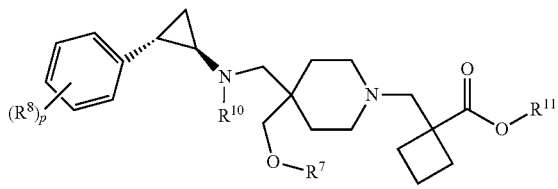

(V)

where R$^7$ is C$_{1-6}$ alkyl or C$_{1-6}$ haloalkyl; R$^8$ is halo, CN, C$_{1-6}$ alkyl, C$_{1-6}$ alkoxy, C$_{1-4}$ haloalkyl, or C$_{1-4}$ haloalkoxy; R$^{10}$ is an amino protecting group; R$^{11}$ is a carboxyl or hydroxyl protecting group; and the subscript p is 0, 1, 2 or 3. In some embodiments of compounds of formula (V), R$^7$ is CH$_3$. In some embodiments of compounds of formula (V), R$^{10}$ is t-butoxycarbonyl. In some embodiments of compounds of formula (V), p is 0. In some embodiments of compounds of formula (V), R$^{11}$ is a benzyl group, wherein the phenyl is optionally substituted with 1-3 R$^9$ substituents. In some embodiments of compounds of formula (V), R$^{11}$ is a benzyl group. In some embodiments of compounds of formula (V), R$^7$ is CH$_3$, R$^{10}$ is t-butoxycarbonyl, R$^{11}$ is benzyl and p is 0.

In some embodiments, the present disclosure provides a synthetic intermediate having Formula (VI):

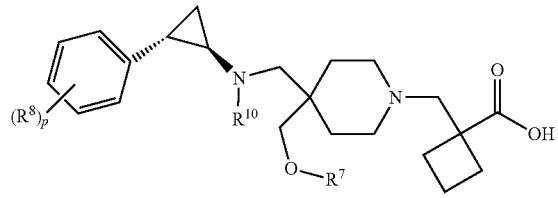

(VI)

where R$^7$ is C$_{1-6}$ alkyl or C$_{1-6}$ haloalkyl; R$^8$ is halo, CN, C$_{1-6}$ alkyl, C$_{1-6}$ alkoxy, C$_{1-4}$ haloalkyl, or C$_{1-4}$ haloalkoxy; R$^{10}$ is an amino protecting group; and the subscript p is 0, 1, 2 or 3. In some embodiments of compounds of formula (VI), R$^7$ is CH$_3$. In some embodiments of compounds of formula (VI), R$^{10}$ is t-butoxycarbonyl. In some embodiments of compounds of formula (VI), p is 0. In some embodiments of compounds of formula (V), R$^7$ is CH$_3$, R$^{10}$ is t-butoxycarbonyl, and p is 0. The intermediate compounds of formulas (II), (III), (IV), (V) or (VI) can be prepared using the synthetic protocols set forth in Example 1.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step, suitable solvent(s) for that particular reaction step can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated hydrocarbon solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methyl pyrrolidone (NMP). Such solvents can be used in either their wet or anhydrous forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Methods of Use

Tosylate salts of Compound I as described herein, including di-tosylate salts, can inhibit the activity of LSD1 and, thus, are useful in treating diseases and disorders associated with activity of LSD1. The present disclosure provides methods of treating an LSD1-associated or mediated disease or disorder in an individual (e.g., patient) by administering to the individual in need of such treatment a therapeutically effective amount or dose of Compound I tosylate salt, or any of the embodiments thereof, or a pharmaceutical composition thereof. The present disclosure also provides a Compound I di-tosylate salt, or any of the embodiments thereof, or a pharmaceutical composition thereof, for use in treating an LSD1-associated or mediated disease or disorder. Also provided is the use of Compound I p-toluenesulfonic acid salt, or any of the embodiments thereof, or a pharmaceutical composition thereof, in the manufacture of a medicament for treating an LSD1-associated or mediated disease or disorder.

An LSD1-associated or mediated disease refers to any disease or condition in which LSD1 plays a role, or where the disease or condition is associated with expression or activity of LSD1. An LSD1-associated disease can include any disease, disorder or condition that is directly or indirectly linked to expression or activity of the LSD1, including over-expression and/or abnormal activity levels. Abnormal activity levels can be determined by comparing activity level in normal, healthy tissue or cells with activity level in diseased cells. An LSD1-associated disease can also include any disease, disorder or condition that can be prevented, ameliorated, inhibited or cured by modulating LSD1 activity. In some embodiments, the disease is characterized by the abnormal activity or expression (e.g., overexpression) of LSD1. In some embodiments, the disease is characterized by mutant LSD1. An LSD1 associated disease can also refer to any disease, disorder or condition wherein modulating the expression or activity of LSD1 is beneficial. The tosylate salts of the present disclosure can therefore be used to treat or lessen the severity of diseases and conditions where LSD1 is known to play a role.

Diseases and conditions treatable using the tosylate salts of the present disclosure include, generally cancers, inflammation, autoimmune diseases, viral induced pathogenesis, beta-globinopathies, and other diseases linked to LSD1 activity.

Cancers treatable using tosylate salts according to the present disclosure include, for example, hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL) and multiple myeloma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids.

The tosylate salts of the present disclosure can further be used to treat cancer types where LSD1 may be overexpressed including, for example, breast, prostate, head and neck, laryngeal, oral, and thyroid cancers (e.g., papillary thyroid carcinoma).

The tosylate salts of the present disclosure can further be used to treat genetic disorders such as Cowden syndrome and Bannayan-Zonana syndrome.

The tosylate salts of the present disclosure can further be used to treat viral diseases such as herpes simplex virus (HSV), varicella zoster virus (VZV), human cytomegalovirus, hepatitis B virus (HBV), and adenovirus.

The tosylate salts of the present disclosure can further be used to treat beta-globinopathies including, for example, beta-thalassemia and sickle cell anemia.

The tosylate salts of the present disclosure can be used to treat triple-negative breast cancer (TNBC), myelodysplastic syndromes, testicular cancer, bile duct cancer, esophageal cancer, and urothelial carcinoma.

In some embodiments, the salts of the present disclosure may be useful in preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The salts of the LSD1 inhibitor as described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the salts of the LSD1 inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, the salts of the LSD1 inhibitor as described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the salts of the LSD1 inhibitor as described herein can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

In some embodiments, biological anticancer drugs, such as antibodies and cytokines, can be combined with the salts of the LSD1 inhibitor as described herein. In addition, drugs modulating microenvironment or immune responses can be combined with the compounds of the invention. Examples of such drugs include anti-Her2 antibodies, anti-CD20 antibodies, anti-CTLA1, anti-PD-1, anti-PDL1, and other immunotherapeutic drugs.

For treating cancer and other proliferative diseases, the salts of the LSD1 inhibitor as described herein can be used in combination with targeted therapies, including FGFR inhibitors (FGFR1, FGFR2, FGFR3 or FGFR4), JAK kinase inhibitors (Ruxolitinib, additional JAK1/2 and JAK1-selective, baricitinib or INCB39110), Pim kinase inhibitors, PI3 kinase inhibitors including PI3K-delta selective and broad spectrum PI3K inhibitors, PI3K-gamma inhibitors such as PI3K-gamma selective inhibitors, MEK inhibitors, CSF1R inhibitors, TAM receptor tyrosine kinases inhibitors (Tyro-3, Axl, and Mer), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors), and indoleamine 2,3-dioxygenase inhibitors (epacadostat and NLG919).

In some embodiments, the salts of the LSD1 inhibitor as described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

In some embodiments, the salts of the LSD1 inhibitor as described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the salts of the LSD1 inhibitor as described herein can be administered in combination with a corticosteroid such as triamcinolone, dexamethasone, fluocinolone, cortisone, prednisolone, or flumetholone.

For treating autoimmune or inflammatory conditions, the salts of the LSD1 inhibitor as described herein can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the salts of the LSD1 inhibitor as described herein can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

For treating beta-thalassemia or sickle cell disease (sickle cell anemia), the salts of the LSD1 inhibitor as described herein can be administered alone or in combination with one or more additional agents described herein such as Hydrea® (hydroxyurea).

In some embodiments, the salts of the LSD1 inhibitor as described herein can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, which can be combined with the salts of the LSD1 inhibitor as described herein include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

When more than one pharmaceutical agent is administered to a patient, they can be administered simultaneously, sequentially, or in combination (e.g., for more than two agents).

Formulation, Dosage Forms and Administration

The salts of the present disclosure can be administered in the form of a pharmaceutical composition. Thus the present disclosure provides a composition comprising the salts of the invention, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, a salt of the invention, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The salts of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least a salt described herein, and at least one pharmaceutically acceptable carrier. In some embodiments, the composition comprises a salt described herein, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at a salt described herein and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Solid oral dosage forms include, for example, tablets, capsules, and pills.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as for tablets, capsules, pills, or other oral dosage forms, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline® (petroleum jelly) and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Example 1

Synthesis of 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) (Compound (I) di-tosylate Salt)

Scheme 1.

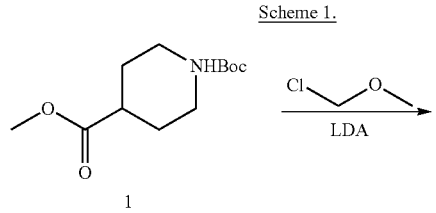

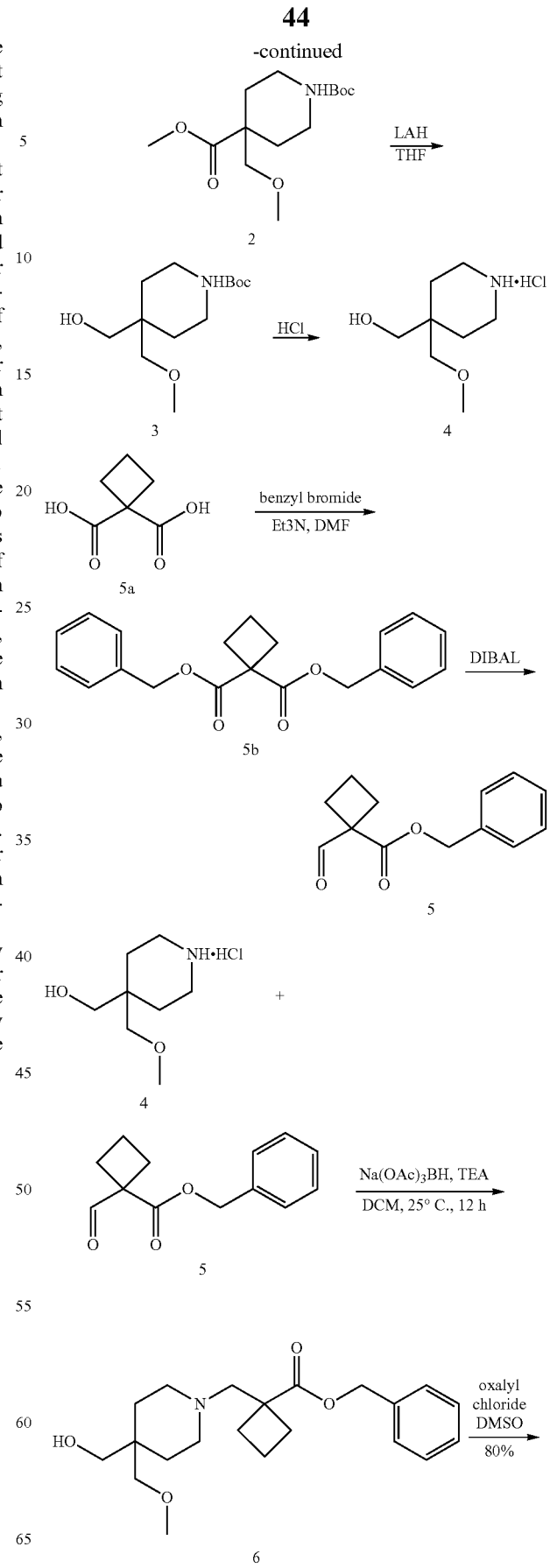

-continued

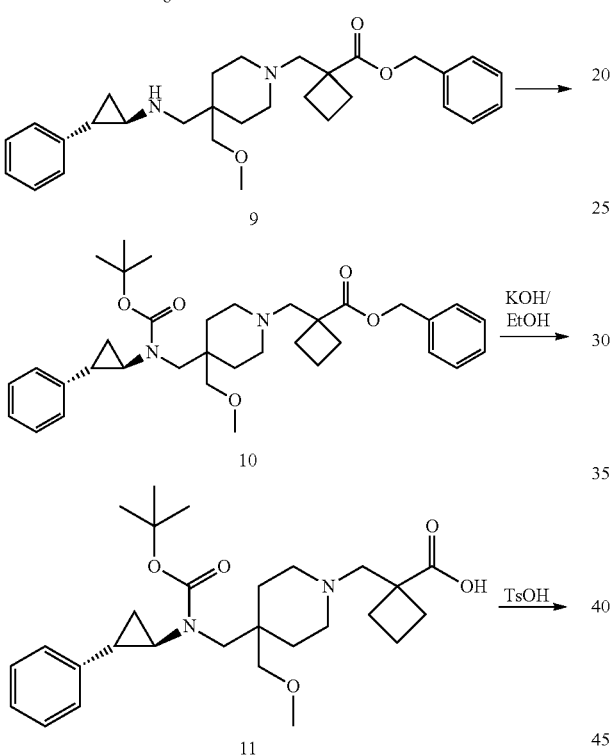

Step 1. Synthesis of 1-tert-butyl 4-(methoxymethyl)piperidine-1,4-dicarboxylate (2)

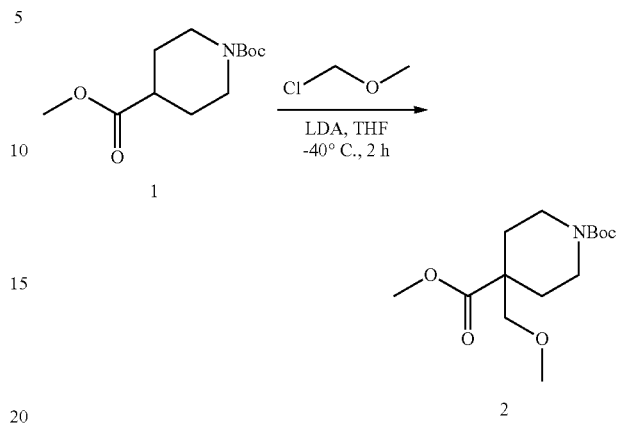

To a solution of N,N-diisopropylamine (165.0 mL, 1180 mmol) in THF was added 2.5 M n-butyllithium in hexane (0.46 L, 1150 mmol) at −78° C. The reaction mixture was stirred at −78° C. for 15 minutes, and warmed to 0° C. for 20 minutes.

The above prepared LDA solution was added to a flask containing 1-t-butyl 4-methyl piperidine-1,4-dicarboxylate (200.0 g, 822.03 mmol) in THF (2.4 L) at −78° C. The reaction mixture was stirred at −78° C. for 10 minutes, then warmed to −40° C. over 1 hour. The reaction mixture was re-cooled to −78° C., then chloromethyl methyl ether (93.6 mL, 1230 mmol) was added dropwise. The mixture was stirred for 2.5 hours allowing the reaction to come to room temperature. The reaction mixture was quenched with saturated aqueous NaHCO$_3$, and extracted with ethyl acetate (2×1.5 L). The combined organics were washed with water and brine, dried over MgSO$_4$, filtered and concentrated to give an oil product (2). The residue was used in the next step without further purification (quantitative yield). $^1$H NMR (400 MHz, CDCl$_3$) δ 3.85 (d, J=13.9 Hz, 2H), 3.74 (s, 3H), 3.39 (s, 2H), 3.31 (s, 3H), 3.02-2.90 (m, 2H), 2.13-2.03 (m, 2H), 1.40-1.46 (m, 11H).

Step 2. Synthesis of tert-butyl 4-(hydroxymethyl)-4-(methoxymethyl)piperidine-1-carboxylate (3)

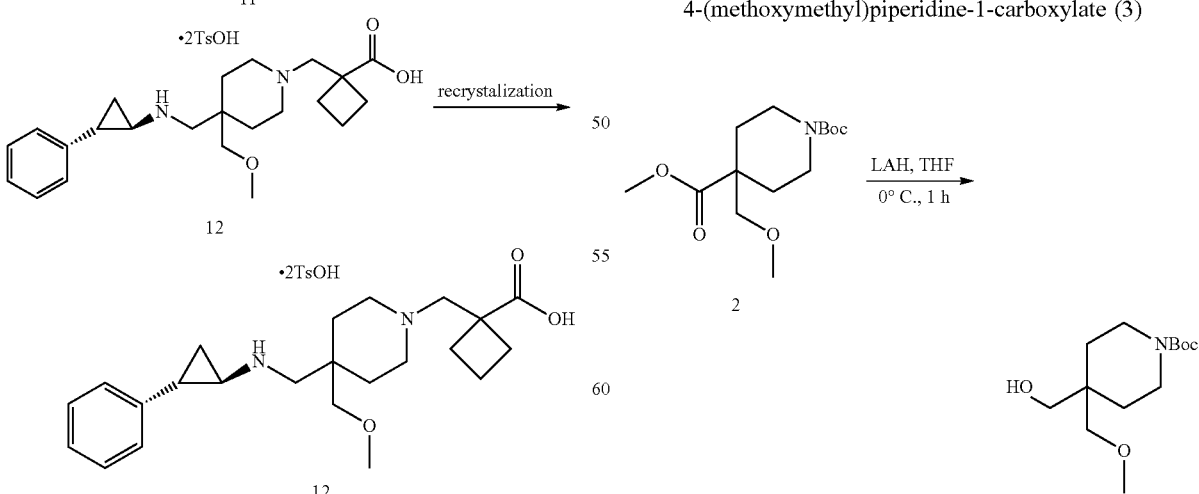

To a dried 22 L 5-neck round bottom flask equipped with stir shaft for mechanical stirring, thermocouple, $N_2$ inlet, addition tube and yellow cap for pressure release was charged 3225 mL dry THF. The solution was cooled to −15° C. using dry ice/IPA bath and charged 1.0 M lithium tetrahydroaluminate in THF (1180 mL, 1180 mmol) to the reactor via cannula directly from vender bottles (the additional LAH was used for EtOAc that is present in the substrate by NMR). The mixture was allowed to warm to −5° C. A solution of 1-tert-butyl 4-(methoxymethyl)piperidine-1,4-dicarboxylate (429.50 g, 1494.7 mmol) in THF (4000 mL) was prepared and transferred to a 12 L round bottom flask. The ester was slowly added to the LAH solution using positive $N_2$ pressure to deliver solution via addition tube (like a plastic cannula). The internal temperature was kept below 8° C. during addition by adjusting the rate of addition. The reaction mixture was stirred at 0° C. for 1 hour.

The reaction mixture was quenched using aq. 1.0N NaOH (260 mL). The initial 21 mL was added slowly under $N_2$. Vigorous $H_2$ evolution and a temperature increase were observed during this part of the quench. Temperature was not allowed to increase above 8° C. Solids began to form and aqueous addition could be performed more rapidly without noticeable gas evolution and temperature increase. Total quenching time was 20 minutes. The mixture was allowed to stir for 15 minutes to break up solids. Celite (500 g) was added and stirred for 45 minutes. The mixture was filtered. The filter cake was washed with ethyl acetate (EtOAc) (2000 mL). The filtrate was added to separation funnel and partitioned between EtOAc (6000 mL) and water (1000 mL). Layers were slow to separate. Some emulsion was observed. The material was purified by Biotage (0-30% EtOAc in hexane) to get pure product (3) (369.5 g, 95.3%). $^1$H NMR (400 MHz, CDCl$_3$) δ 3.62 (s, 2H), 3.45 (d, J=2.3 Hz, 1H), 3.41-3.32 (m, 7H), 2.33 (s, 2H), 1.55-1.42 (m, 13H).

Step 3. Synthesis of [4-(methoxymethyl)piperidin-yl]methanol hydrochloride (4)

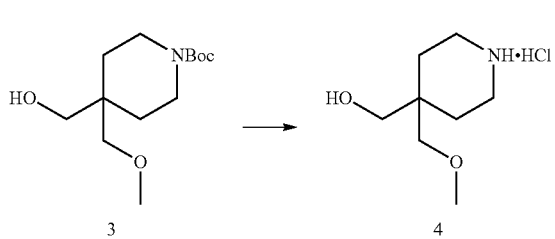

To a solution of tert-butyl 4-(hydroxymethyl)-4-(methoxymethyl)piperidine-1-carboxylate (113.70 g, 438.42 mmol) in DCM (0.667 L) was added 4.0 M HCl in dioxane (0.767 mL, 3070 mmol) at 0° C. The reaction mixture was stirred at room temperature for 1 hour. Filtration of the reaction mixture provided pure product (4) (77.0 g, 89.8%). LC-MS calculated for $C_{24}H_{18}ClNO_2$ [M+H]$^+$ m/z: 196.1; found 196.1. $^1$H NMR (400 MHz, DMSO) δ 9.02 (s, 1H), 3.31-3.18 (m, 7H), 2.98 (d, J=6.0 Hz, 4H), 1.61-1.53 (m, 4H).

Step 4. Synthesis of dibenzyl cyclobutane-1,1-dicarboxylate (5b)

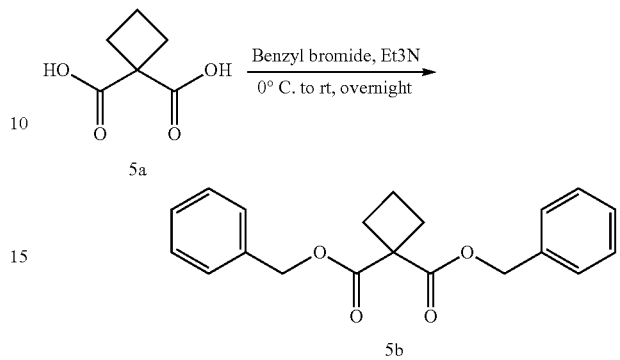

To a solution of 1,1-cyclobutanedicarboxylic acid (50.00 g, 346.9 mmol) in DMF (180 mL) was added trimethylamine (102 mL, 728 mmol) at 0° C. (keeping temperature below 15° C. during the addition). The reaction mixture was stirred at 0° C. for 15 minutes, then benzyl bromide (144 mL, 1210 mmol) was added (keeping temperature below 30° C.). After 10 minutes, the ice bath was removed. The reaction mixture was stirred at room temperature overnight.

To the reaction mixture was added water (300 mL). The mixture was partitioned between DCM (300 mL) and aqueous solution. The organics were washed with 1.0 N HCl solution (200 mL), 10% NaHCO$_3$ solution (200 mL) and brine (200 mL), then dried over MgSO$_4$ and concentrated to give crude material (5b) (111.10 g), which was used for next step. $^1$H NMR (400 MHz, CDCl$_3$) δ 7.37-7.24 (m, 10H), 5.17 (s, 4H), 2.64-2.55 (t, J=8.0 Hz, 4H), 2.02 (p, J=8.0 Hz, 2H).

Step 5. Synthesis of benzyl 1-formylcyclobutanecarboxylate (5)

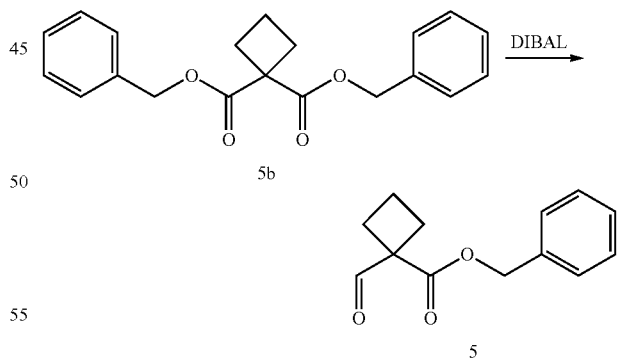

To a solution of dibenzyl cyclobutane-1,1-dicarboxylate (30.00 g, 92.49 mmol) in DCM (200.00 mL) at −75° C. was added 1.0 M diisobutylaluminum hydride in DCM (185 mL) dropwise. The temperature was controlled between −70° C. and −60° C. The reaction mixture was stirred at −75° C. for 1 hour.

The reaction was quenched with slow addition of 1.0 M hydrogen chloride in water (200.0 mL). The resulting mixture was warmed to room temperature and stirred for another Step 6. Synthesis of benzyl 1-((4-(hydroxymethyl)-4-(methoxymethyl)piperidin-1-yl)methyl)cyclobutane-1-carboxylate (6)

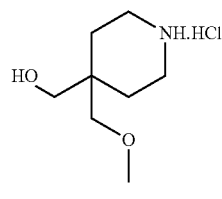

4

+

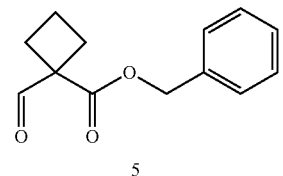

5

Na(OAc)₃BH,TEA
DCM, 25° C., 2 h
→

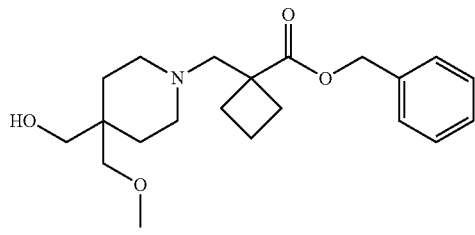

6

To a solution of [4-(methoxymethyl)piperidin-4-yl] methanol hydrochloride (10.8 g, 55.4 mmol) and benzyl 1-formylcyclobutanecarboxylate (14.40 g, 52.78 mmol) in DCM (300 mL) was added trimethylamine (18.4 mL, 132 mmol) at room temperature. The reaction mixture was stirred at room temperature for 1 hour. Sodium triacetoxyborohydride (22.4 g, 106 mmol) was added with a water bath portionwise. The reaction mixture was stirred at room temperature overnight.

To the reaction mixture was added saturated NaHCO₃ solution (200 mL). The mixture was partitioned between DCM and NaHCO₃ solution. The organics were dried and concentrated to provide oil crude product. Biotage (EtOAc/hexane: 0-45%) gave pure product (6) (16.6 g, 87%). LC-MS calculated for $C_{21}H_{31}NO_4$ [M+H]⁺ m/z: 362.2; found 362.2. ¹H NMR (400 MHz, CD3CN) δ 7.47-7.30 (m, 5H), 5.16 (s, 2H), 3.38 (s, 2H), 3.30 (s, 3H), 3.24 (s, 2H), 2.71 (s, 2H), 2.43 (ddd, J=12.1, 9.4, 7.2 Hz, 2H), 2.36-2.28 (m, 4H), 2.09-1.82 (m, 4H), 1.39-1.31 (m, 4H).

Step 7. Synthesis of Benzyl 1-{[4-formyl-4-(methoxymethyl)piperidin-1-yl] methyl}cyclobutanecarboxylate (7)

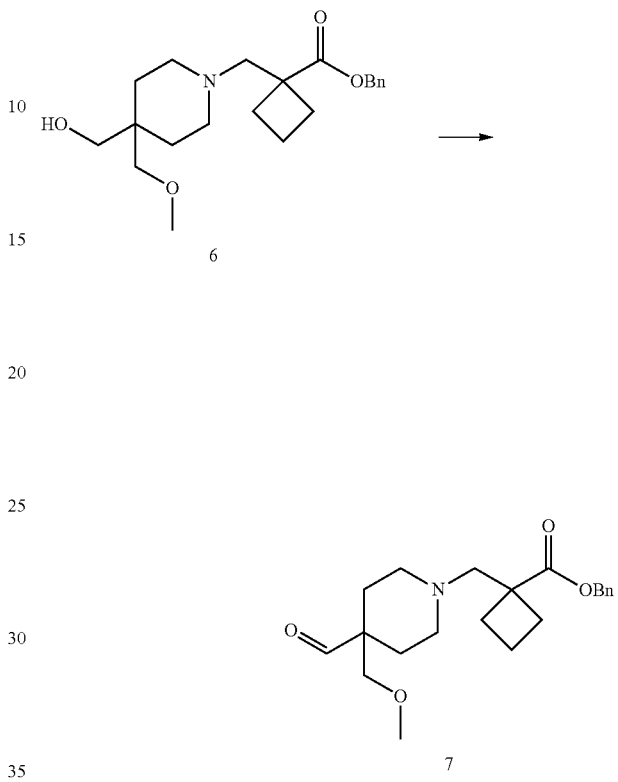

To a solution of oxalyl chloride (226 mL, 339 g, 2.67 moles) in dichloromethane (1.1 L) was added a solution of dimethyl sulfoxide (378 mL, 416 g, 5.32 moles) in dichloromethane (500 mL) over one hour, while maintaining the internal temperature at below −55° C. After stirring at −50° C. for 30 minutes, a solution of benzyl 1-((4-(hydroxymethyl)-4-(methoxymethyl)piperidin-1-yl)methyl)cyclobutane-1-carboxylate (475 g, 1.315 mol) in dichloromethane (1.1 L) was added over 45 minutes, maintaining the internal temperature below −50° C. After stirring at −50° C. for 30 minutes, triethylamine (1480 mL, 10.62 moles) was added. The reaction temperature rose to 15° C. during the addition. After stirring for 20 minutes, ice cold water (5 L) was added and the layers were separated. The organic layer was washed with water (2 L) and 10% sodium bicarbonate (6.2 L). Each aqueous layer was re-extracted with dichloromethane (3.5 L). The combined organic layers were concentrated under reduced pressure. The crude product was purified over silica gel (5 kg), eluting with a gradient 0 to 100% ethyl acetate in heptane to give compound (7) (402 g, 85% yield, 98% purity) as colorless oil. LC-MS calculated for $C_{21}H_{29}NO_4$ [M+H]⁺ m/z: 361.2; found 361.2. ¹H NMR (400 MHz, CD3CN) δ 9.47 (s, 1H), 7.47-7.33 (m, 5H), 5.16 (s, 2H), 3.38 (s, 2H), 3.26 (s, 3H), 2.67 (s, 2H), 2.54-2.38 (m, 4H), 2.16-1.93 (m, 4H), 1.91-1.78 (m, 4H), 1.38 (ddd, J=13.9, 10.3, 4.0 Hz, 2H).

Step 8. Synthesis of benzyl 1-((4-(methoxymethyl)-4-(((1R,2S)-2-phenylcyclopropylamino)methyl)piperidin-1-yl)methyl)cyclobutanecarboxylate (9) and Benzyl 1-{[4-({(tert-butoxycarbonyl)[(1R,2S)-2-phenylcyclopropyl]amino}methyl)-4-(methoxymethyl)piperidin-1-yl]methyl}cyclobutanecarboxylate (10)

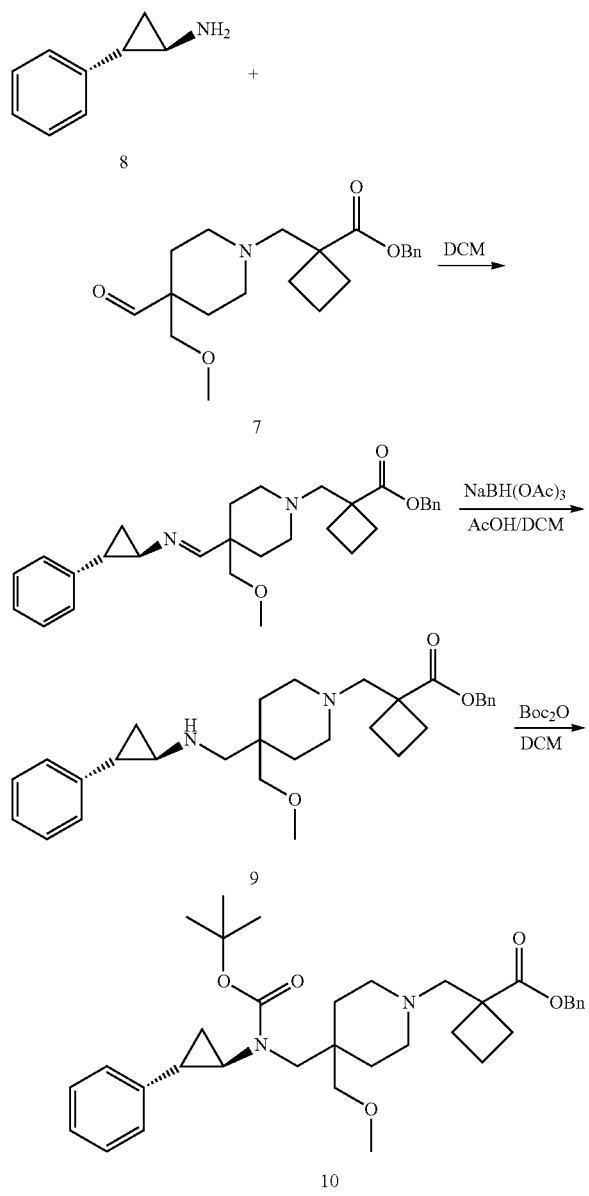

Benzyl 1-{[4-formyl-4-(methoxymethyl)piperidin-1-yl]methyl}cyclobutanecarboxylate (7) (136.10 g, 378.62 mmol) and (1R,2S)-2-phenylcyclopropanamine (8) (61.0 g, 458.0 mmol) were mixed in methylene chloride (1225 mL). The mixture was then concentrated under vacuum with a bath temperature of 40° C. The oily residue was re-dissolved in methylene chloride (1225 mL). The solution was then concentrated under vacuum with a bath temperature of 40° C. The formation of imine was confirmed by LC-MS at pH 10.

The residue was dissolved in methylene chloride (1225 mL), acetic acid (45.1 mL, 793.0 mmol) was added, followed by sodium triacetoxyborohydride (79.4 g, 793.0 mmol). The mixture was stirred for 1.5 hours. HPLC indicated the completion of the reaction. Methylene chloride (1225 mL) was added to dilute the reaction. To the mixture was added 7% aqueous sodium bicarbonate (2449.6 g), the mixture was stirred for 30 minutes and DCM phase was collected. The organic phase was washed with aqueous 7% sodium bicarbonate (2449.6 g), then concentrated under vacuum to about 1300-1500 mL volume, and used directly for the next step.

To the above solution was added di-tert-butyldicarbonate (180.0 g, 377.63 mmol). The mixture was stirred at room temperature overnight. To the reaction mixture was added aqueous 7% sodium bicarbonate and after stirring for 30 minutes, the organic phase was collected, dried over MgSO$_4$ and concentrated. The residue was purified by Biotage (0-20% ethyl acetate in hexane, checked by anisaldehyde as stain) to give compound (10) (190.0 g, 87.2%). Compound (9): LC-MS calculated for $C_{30}H_{40}N_2O_3$ [M+H]$^+$ m/z: 477.3; found 477.3. $^1$H NMR (400 MHz, D$_2$O) δ 7.49-7.23 (m, 8H), 7.18 (d, J=7.3 Hz, 2H), 5.23 (s, 2H), 3.56 (s, 2H), 3.34 (s, 3H), 3.23 (s, 2H), 3.16 (s, 3H), 3.01 (s, 2H), 2.48 (dt, J=11.2, 8.1 Hz, 3H), 2.17-1.93 (m, 4H), 1.55-1.49 (m, 5H), 1.37 (q, J=7.2 Hz, 1H). Compound (10): LC-MS calculated for $C_{35}H_{48}N_2O_5$ [M+H]$^+$ m/z: 577.3; found 577.3. $^1$H NMR (400 MHz, CD3CN) δ 7.46-7.23 (m, 8H), 7.15 (dd, J=28.9, 7.3 Hz, 2H), 5.15 (s, 2H), 3.44 (d, J=14.5 Hz, 1H), 3.31-3.07 (m, 5H), 2.78-2.67 (m, 3H), 2.43 (dd, J=11.1, 5.8 Hz, 4H), 2.26 (ddd, J=24.0, 11.7, 4.7 Hz, 4H), 2.08-1.95 (m, 4H), 1.86 (p, J=7.3, 6.6 Hz, 2H), 1.55-1.44 (m, 1H), 1.44-1.28 (m, 13H), 1.21 (dq, J=13.5, 6.8 Hz, 1H).

Compound (10) can also be purified by reacting compound (10) with L-tartaric acid in the presence of isopropanol, methanol, and n-heptane to form compound (10) L-tartrate and reacting compound (10) L-tartrate with NaHCO$_3$ in dichloromethane to provide purified compound (10). The corresponding salt formation and neutralization procedures are described below.

Crude compound 10 and 2-propanol are stirred at 15-30° C. for about 15 minutes until a solution is obtained. L-Tartaric acid and methanol are stirred at 15-30° C. for about 1 hour until a solution is obtained. The L-tartaric acid solution is then added to the solution of crude compound 10 and the reaction mixture is stirred at 15-30° c. for about 1 hour. n-Heptane is then added to the reaction mixture and the resulting mixture is stirred at 15-30° C. for about 1 hour. The reaction mixture is filtered and the wet cake is washed with n-heptane and dried to afford the corresponding L-tartaric acid salt of compound 10.

Dichloromethane (DCM) and L-tartaric acid salt of compound 10 are charged to a reactor at ambient temperature, and aqueous NaHCO$_3$ solution is charged to the reactor while maintaining the reaction mixture at no more than 30° C. The reaction mixture is stirred at 15-30° C. for about 30 minutes and the phases are separated. The organic phase is concentrated under reduced pressure until the distillation stops. The distillation residue is then treated with ethanol (EtOH) and the resulting solution of compound 10 in ethanol (EtOH) is directly used in the subsequent reaction without further purification.

Step 9. Synthesis of 1-{[4-({(tert-butoxycarbonyl)[(1R,2S)-2-phenylcyclopropyl]amino}methyl)-4-(methoxymethyl)piperidin-1-yl]methyl}cyclobutanecarboxylic acid (11)

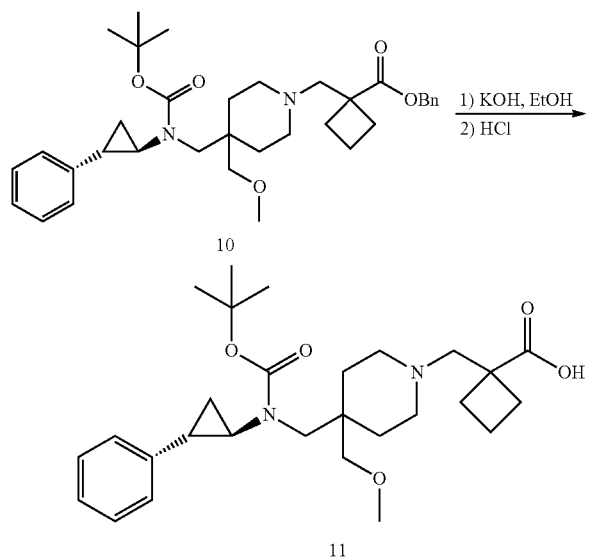

Benzyl 1-{[4-({(tert-butoxycarbonyl)[(1R,2S)-2-phenylcyclopropyl]amino}methyl)-4-(methoxymethyl)piperidin-1-yl]methyl}) cyclobutanecarboxylate (10) (449.10 g, 778.65 mmol) was dissolved in ethanol (1570 mL). The solution was concentrated in vacuo with a bath temperature at 40° C. The residue was again dissolved in ethanol (1570 mL) and the solution was concentrated using in vacuo with bath temperature at 40° C. To the residue was added a solution of potassium hydroxide (89.9 g, 1604 mmol) in ethanol (1570 mL) and water (224.6 mL). The mixture was then heated in a bath at 40° C. HPLC indicated the reaction was complete (PCT 0.5%) after 8 hours.

A vacuum was applied to remove ethanol, then water was added (2000 mL), the mixture concentrated down, and then the process was repeated one more time to yield crude product. Water (1570 mL), 2-methoxy-2-methylpropane (2246 mL) and sodium chloride (200.0 mL) were added to the crude product. The organic layer was then collected, and concentrated. The residue was re-dissolved in water (2000 mL), and then concentrated to dryness.

The residue was re-dissolved in water (2000 mL) and the solution was washed again with 2-methoxy-2-methylpropane (2246 mL). The repeated washing with MTBE was performed until the benzyl alcohol was less than 0.5% in aqueous layer. The aqueous solution was then cooled in an ice bath before being treated dropwise with an aqueous HCl solution, made from the concentrated hydrochloric acid (conc. HCl, 95.0 g, 951 mmol) and water (450.0 g), until pH 5.

The mixture was extracted with methylene chloride (3000 mL×2) twice. The combined DCM layers were concentrated to give the desired product (11) as a white solid, which was used directly in the next step. LC-MS calculated for $C_{28}H_{42}N_2O_5$ [M+H]$^+$ m/z: 487.3; found 487.3. $^1$H NMR (400 MHz, CD3CN) δ 7.29 (t, J=7.5 Hz, 2H), 7.17 (dd, J=24.1, 7.3 Hz, 3H), 3.53 (d, J=14.4 Hz, 1H), 3.34-3.14 (m, 5H), 3.01-2.73 (m, 7H), 2.43-2.36 (m, 2H), 2.21-1.82 (m, 7H), 1.79-1.58 (m, 4H), 1.38 (s, 9H), 1.23 (q, J=6.5 Hz, 1H).

Step 10. Synthesis of 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12)

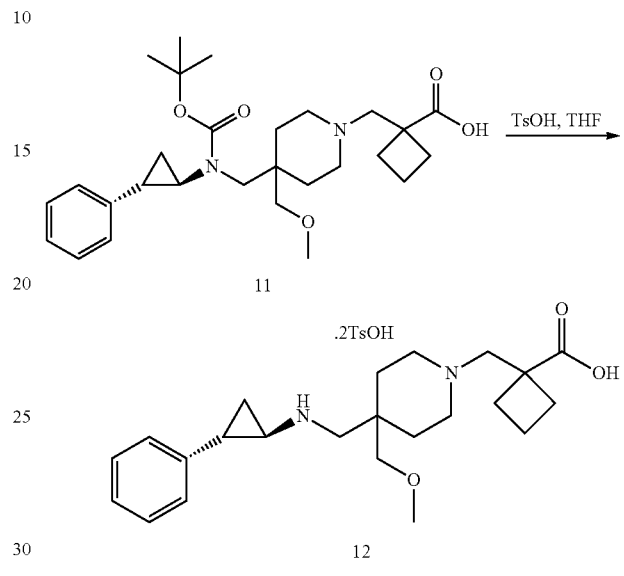

compound (I) di-tosylate salt

1-{[4-({(tert-Butoxycarbonyl)[(1R,2 S)-2-phenylcyclopropyl]amino}methyl)-4-(methoxymethyl)piperidin-1-yl]methyl}cyclobutanecarboxylic acid (11) (370.0 g, 722.4 mmol) was dissolved in tetrahydrofuran (2000.0 mL). To the solution was added p-toluenesulfonic acid monohydrate (300.0 g, 1577 mmol). The mixture was heated to 55-60° C. In 14 hours, HPLC indicated the reaction was complete (SM<1%). To the mixture while heating was added 2-methoxy-2-methylpropane (4000 mL) through an addition funnel. The reaction mixture was kept stirring for 6 hours at 55° C.-60° C. before disconnection of the heat. The mixture was cooled down to room temperature and stirred overnight. Solid product was collected by filtration and the cake was washed with 2-methoxy-2-methylpropane (1000 mL) twice, and dried on the filter overnight. The material 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) also known as 1-{[4-(methoxymethyl)-4-({[(1R,2S)-2-phenylcyclopropyl]amino}methyl)piperidin-1-yl]methyl}cyclobutanecarboxylic acid ditosylate salt was used directly for recrystallization.

Step 11. Crystalline Form I of 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate (Compound I di-tosylate salt, Form I)

1-{[4-(Methoxymethyl)-4-({[(1R,2S)-2-phenylcyclopropyl]amino}methyl)piperidin-1-yl]methyl}cyclobutanecarboxylic acid bis(4-methylbenzenesulfonate) (12) (532.9 g, 729.1 mmol) was mixed with 2-butanone (7223 mL). The mixture was heated to 55° C. (internal temperature set) to become a clear solution. The hot solution was polish filtered through an inline filter, and the clear solution was distilled off under vacuum to about 4 L volume while being heated at 55° C. (internal temperature set). To the solution was added heptane (4676 mL) while stirring. After the addition, the mixture was kept at 55° C. (internal temperature set) for 4 hours, then allowed to cool to room temperature. The mixture was stirred overnight. The solid was filtered and washed with a mixture of heptane (1000.0 mL) and 2-butanone (1000.0 mL). The recrystallized product 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) (12) was dried on the filter overnight, and then under high vacuum at 50° C. overnight to give pure product. LC-MS calculated for $C_{37}H_{50}N_2O_9S_2$ [M+H]$^+$ m/z: 387.2; found 387.2. $^1$H NMR (400 MHz, MeOD) δ 7.73 (d, J=8.2 Hz, 4H), 7.34-7.19 (m, 7H), 7.15 (d, J=7.2 Hz, 2H), 3.70-3.51 (m, 4H), 3.43 (d, J=18.4 Hz, 7H), 3.36-3.22 (m, 3H), 3.13-2.97 (m, 1H), 2.67-2.50 (m, 3H), 2.38 (s, 6H), 2.21 (q, J=9.5, 8.6 Hz, 2H), 2.05 (dt, J=28.5, 11.6 Hz, 2H), 1.94-1.78 (m, 1H), 1.66-1.55 (m, 1H), 1.32 (d, J=8.0 Hz, 2H), 0.92 (t, J=6.8 Hz, 1H).

Example 2

X-Ray Powder Diffraction (XRPD) of Form I

Form I was characterized by XRPD. The X-Ray Power Diffraction (XRPD) was obtained from Rigaku MiniFlex X-ray Powder Diffractometer (XRPD). The general experimental procedures for XRPD were: (1) X-ray radiation from copper at 1.054056 Å with K$_β$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min. The XRPD pattern is shown in FIG. 1 and the XRPD data are provided in Table 1.

TABLE 1

| 2-Theta (°) | Height | H % |
|---|---|---|
| 3.6 | 460 | 70 |
| 4.9 | 608 | 92.5 |
| 6.2 | 658 | 100 |
| 7.7 | 326 | 49.6 |
| 8.9 | 116 | 17.6 |
| 10.0 | 128 | 19.5 |
| 11.5 | 132 | 20.1 |
| 13.8 | 42 | 6.3 |
| 14.3 | 51 | 7.8 |
| 15.0 | 98 | 14.9 |
| 15.5 | 105 | 15.9 |
| 16.3 | 123 | 18.7 |
| 17.1 | 49 | 7.4 |
| 17.8 | 170 | 25.8 |
| 19.1 | 163 | 24.8 |
| 19.8 | 108 | 16.4 |
| 20.9 | 202 | 30.8 |
| 22.2 | 170 | 25.9 |
| 22.7 | 408 | 62 |
| 23.1 | 133 | 20.3 |
| 23.9 | 49 | 7.5 |
| 24.4 | 94 | 14.3 |
| 24.9 | 73 | 11 |
| 25.8 | 65 | 9.9 |
| 27.2 | 55 | 8.4 |
| 28.7 | 43 | 6.5 |
| 29.1 | 53 | 8.1 |

TABLE 1-continued

| 2-Theta (°) | Height | H % |
|---|---|---|
| 30.6 | 47 | 7.1 |
| 31.2 | 70 | 10.6 |
| 32.8 | 59 | 9 |
| 38.4 | 39 | 5.9 |
| 39.6 | 35 | 5.4 |
| 43.9 | 36 | 5.5 |

Example 3

Differential Scanning Calorimetry (DSC) Thermogram of Form I

Form I was characterized by DSC. The DSC was obtained from TA Instruments Differential Scanning Calorimetry, Model Q200 with autosampler. The DSC instrument conditions were as follows: 30-300° C. at 10° C./min; T$_{zero}$ aluminum sample pan and lid; and nitrogen gas flow at 50 mL/min. The DSC thermogram is shown in FIG. 2. The DSC thermogram revealed a major endothermal event at an onset temperature of 94.6° C. with a peak temperature of 103.1° C. which is believed to be the melting of the compound.

Example 4

Thermogravimetric Analysis (TGA) of Form I

Form I was characterized by TGA. The TGA was obtained using a TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan. The TGA thermogram is shown in FIG. 3. A weight loss of about 3.5% up to 150° C. was observed and believed to be associated with the loss of moisture and residual solvents. The compound started to decompose significantly after 200° C.

Example 5

Dynamic Vapor Sorption (DVS) Analysis of Form I

Form I was characterized by DVS. The DVS analysis was performed on a TA Instruments Vapor Sorption Analyzer, model VTI-SA$^+$. The sample was pre-dried on VTI at 50° C. with 0% RH N$_2$ for 1 h. Then the moisture uptake profile was completed in one cycle in 5% RH increments with adsorption from 0% RH to 95% RH followed by desorption in 5% increments from 95% to 5% RH. The equilibration criteria were 0.0050 wt % in 5 minutes with a maximum equilibration time of 180 minutes. All adsorption and desorption were performed at 25° C.

Figure 16:
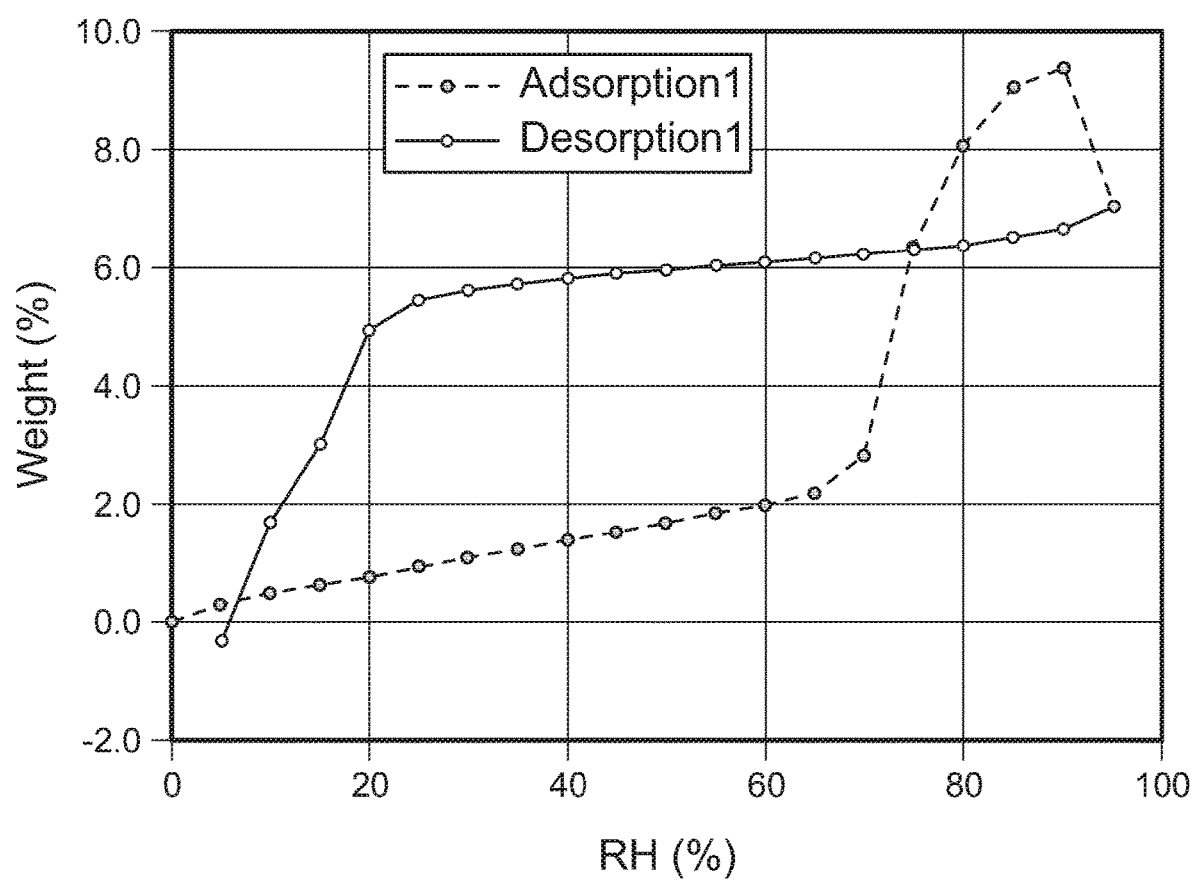
FIG. 16 shows a DVS adsorption-desorption isotherm of Compound I di-tosylate salt, Form I.

The adsorption/desorption isotherm is shown in FIG. 16. Form I is hygroscopic and can change to different hydrates under different conditions.

Example 6

Preparation and Characterization of Form HI

Form HI of Compound I di-tosylate salt was prepared during the process of drying a wet sample of Compound I di-tosylate salt, Form I, under ambient conditions. Form I slowly absorbed atmospheric moisture and gradually changed to crystalline Form HI. Under storage conditions of 25° C./60% RH and 40° C./75% RH, Form I was also converted to Form HI. Form HI can also be generated by purging humidified air (e.g., 60-85% RH) through Form I solid.

Form HI was characterized by XRPD. The X-Ray Powder Diffraction (XRPD) was obtained from Bruker D2 PHASER X-ray Powder Diffractometer (XRPD) instrument. The general experimental procedures for XRPD were: (1) X-ray radiation from copper at 1.054056 Å with $K_\beta$ filter and LYNXEYE™ detector; (2) X-ray power at 30 KV, 10 mA; and (3) the sample powder was dispersed on a zero-background sample holder. The general measurement conditions for XRPD were: Start Angle 5 degrees; Stop Angle 30 degrees; Sampling 0.015 degrees; and Scan speed 2 degree/min. The XRPD pattern is shown in FIG. 4 and the XRPD data are provided in Table 2.

TABLE 2

| 2-Theta (°) | Height | H % |
|---|---|---|
| 7.0 | 4354 | 77.6 |
| 8.9 | 886 | 15.8 |
| 9.3 | 1185 | 21.1 |
| 10.4 | 3139 | 55.9 |
| 10.7 | 660 | 11.8 |
| 11.5 | 51 | 0.9 |
| 12.0 | 151 | 2.7 |
| 13.6 | 2036 | 36.3 |
| 14.1 | 491 | 8.7 |
| 14.4 | 124 | 2.2 |
| 15.5 | 4512 | 80.4 |
| 16.2 | 857 | 15.3 |
| 16.6 | 2374 | 42.3 |
| 17.3 | 4304 | 76.7 |
| 17.9 | 1242 | 22.1 |
| 18.7 | 2547 | 45.4 |
| 19.8 | 3854 | 68.7 |
| 20.2 | 3439 | 61.3 |
| 20.5 | 2144 | 38.2 |
| 20.8 | 4164 | 74.2 |
| 21.4 | 1389 | 24.8 |
| 21.7 | 2735 | 48.7 |
| 22.2 | 4344 | 77.4 |
| 23.1 | 2229 | 39.7 |
| 24.0 | 5611 | 100 |
| 24.7 | 126 | 2.2 |
| 25.3 | 786 | 14.0 |
| 25.5 | 1072 | 19.1 |
| 26.0 | 379 | 6.8 |
| 26.7 | 730 | 13.0 |
| 27.3 | 340 | 6.1 |
| 28.2 | 1649 | 29.4 |
| 28.8 | 246 | 4.4 |
| 29.2 | 144 | 2.6 |

Form HI was characterized by DSC. The DSC was obtained from TA Instruments Differential Scanning Calorimetry, Model Q2000 with autosampler. The DSC instrument conditions were as follows: 25-150° C. at 10° C./min; $T_{zero}$ aluminum sample pan and lid; and nitrogen gas flow at 50 mL/min. The DSC thermogram is shown in FIG. 5. The DSC thermogram revealed a major endothermal event at an onset temperature of 73.5° C. with a peak temperature of 79.8° C. which is believed to be a dehydration event.

Form HI was characterized by TGA. The TGA was obtained using a PerkinElmer Thermogravimetric Analyzer, Model Pyris 1. The general experimental conditions for TGA were: ramp from 25° C. to 200° C. at 10° C./min; nitrogen purge gas flow at 60 mL/min; ceramic crucible sample holder. The TGA thermogram is shown in FIG. 6. A weight loss of about 5.3% up to 110° C. was observed and believed to be associated mostly with the loss of water.

Form HI was characterized by DVS. The DVS analysis was performed on a TA Instruments Vapor Sorption Analyzer, model VTI-SA⁺. The moisture uptake profile was completed in one cycle in 5% RH increments with adsorption from 35% RH to 95% RH followed by desorption in 5% increments from 95% to 5% RH. The equilibration criteria were 0.0010 wt % in 5 minutes with a maximum equilibration time of 180 minutes. All adsorption and desorption were performed at 25° C. No pre-drying step was applied for the sample.

Figure 17:
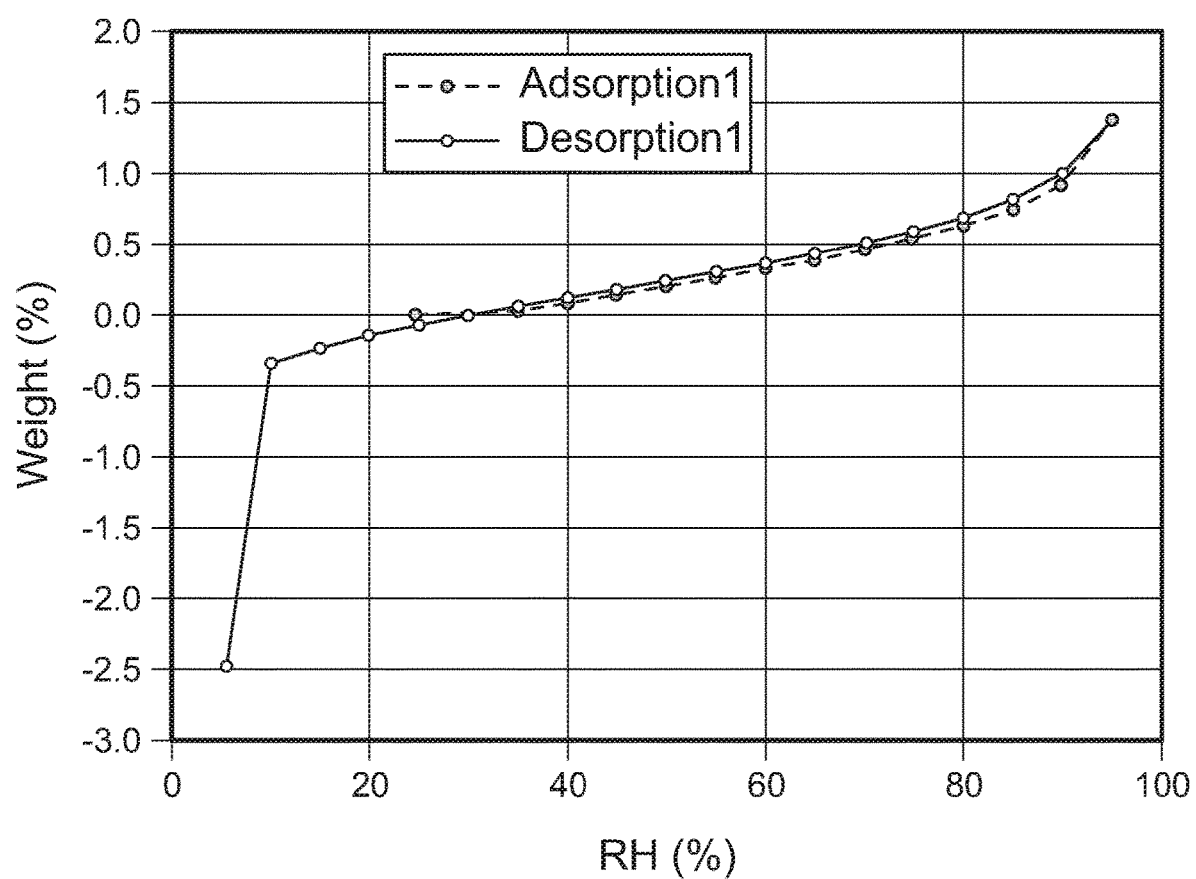
FIG. 17 shows a DVS adsorption-desorption isotherm of Compound I di-tosylate salt, Form HI.

The adsorption/desorption isotherm is shown in FIG. 17. Form HI is slightly hygroscopic. It can absorb more water at high humidity and can be de-hydrated at low humidity.

Example 7

Preparation and Characterization of Form HII

Form HII was prepared by slurring of Form I in water for 3 days at room temperature. The resulted suspension was filtered. The residual solid was collected and air dried for 5-7 days at ambient condition.

Form HII was characterized by XRPD. The XRPD was obtained from Bruker D2 PHASER X-ray Powder Diffractometer instrument. The general experimental procedures for XRPD are similar to those for Form HI. The XRPD pattern is shown in FIG. 7 and the XRPD data are provided in Table 3.

TABLE 3

| 2-Theta (°) | Height | H % |
|---|---|---|
| 6.5 | 902 | 21.6 |
| 6.9 | 1739 | 43.0 |
| 8.0 | 74.7 | 1.8 |
| 8.7 | 2372 | 56.9 |
| 10.1 | 4023 | 96.5 |
| 10.9 | 212 | 5.1 |
| 12.8 | 103 | 2.5 |
| 13.7 | 717 | 17.2 |
| 14.3 | 2944 | 70.6 |
| 14.8 | 3399 | 81.5 |
| 15.5 | 699 | 16.8 |
| 15.6 | 662 | 15.9 |
| 15.9 | 873 | 20.9 |
| 16.0 | 808 | 19.4 |
| 16.5 | 526 | 12.6 |
| 16.9 | 1215 | 29.1 |
| 17.4 | 2487 | 59.6 |
| 17.7 | 2644 | 63.4 |
| 18.2 | 2023 | 48.5 |
| 19.3 | 195 | 4.7 |
| 20.0 | 1888 | 45.3 |
| 20.5 | 3037 | 72.8 |
| 20.6 | 2694 | 64.6 |
| 21.3 | 3226 | 77.4 |
| 22.1 | 2317 | 55.6 |
| 22.0 | 3129 | 75.0 |
| 22.7 | 4170 | 100 |
| 23.2 | 1453 | 34.8 |
| 23.5 | 1263 | 30.3 |
| 24.3 | 3560 | 85.4 |
| 24.6 | 2153 | 51.6 |
| 25.1 | 804 | 19.3 |
| 25.4 | 792 | 19.0 |
| 26.1 | 594 | 14.2 |
| 27.1 | 817 | 19.6 |
| 27.6 | 184 | 4.4 |
| 28.4 | 2374 | 56.9 |
| 29.5 | 290 | 7.0 |

Form HII was characterized by DSC. The DSC was obtained from TA Instruments Differential Scanning Calorimetry, Model Q2000 with autosampler. The DSC instrument conditions are similar to those for Form HI. The DSC thermogram is shown in FIG. 8. The DSC thermogram revealed a major endothermal event at an onset temperature of 49.0° C. with a peak temperature of 52.3° C. which is believed to be the dehydration of the compound.

Form HII was characterized by TGA. The TGA was obtained from PerkinElmer Thermogravimetric Analyzer, Model Pyris 1. The general experimental conditions for TGA are similar to those for Form HI. The TGA thermogram is shown in FIG. 9. A weight loss of about 11.3% up to 120° C. was observed and is believed to be associated mostly with the loss of water.

Example 8

Preparation and Characterization of Form HIII

Form HIII was prepared by drying Form HI on Vapor Sorption Analyzer (TA Instruments VTI-SA+) at 40° C. with 0% RH $N_2$ for 3 h and then exposing it to humidity at about 30-50% RH at 25° C. for 1 day. Form HIII can change to Form HI when it is further exposed to high humidity at about 60-85% RH.

Form HIII was characterized by XRPD. The XRPD was obtained from Bruker D2 PHASER X-ray Powder Diffractometer (XRPD) instrument. The general experimental procedures for XRPD are similar to those for Form HI. The XRPD pattern is shown in FIG. 10 and the XRPD data are provided in Table 4.

TABLE 4

| 2-Theta (°) | Height | H % |
|---|---|---|
| 7.0 | 1719 | 31.2 |
| 8.6 | 86.6 | 1.6 |
| 9.0 | 2232 | 40.5 |
| 9.2 | 2435 | 44.1 |
| 10.2 | 3550 | 64.4 |
| 10.6 | 110 | 2.0 |
| 11.7 | 481 | 8.7 |
| 13.1 | 1671 | 30.3 |
| 13.5 | 99.6 | 1.8 |
| 13.9 | 150 | 2.7 |
| 14.3 | 269 | 4.9 |
| 15.0 | 1698 | 30.8 |
| 15.6 | 1398 | 25.3 |
| 16.2 | 742 | 13.4 |
| 16.3 | 443 | 8.0 |
| 17.1 | 1989 | 36.1 |
| 17.4 | 2147 | 38.9 |
| 17.9 | 2597 | 47.1 |
| 18.4 | 519 | 9.4 |
| 18.9 | 1756 | 31.8 |
| 19.8 | 475 | 8.6 |
| 20.3 | 4956 | 89.8 |
| 20.9 | 842 | 15.3 |
| 22.0 | 4791 | 86.9 |
| 22.5 | 736 | 13.3 |
| 22.9 | 635 | 11.5 |
| 23.4 | 603 | 10.9 |
| 23.5 | 826 | 15.0 |
| 23.8 | 5517 | 100 |
| 24.0 | 1063 | 19.3 |
| 24.6 | 453 | 8.2 |
| 25.2 | 849 | 15.4 |
| 25.5 | 580 | 10.5 |
| 26.2 | 778 | 14.1 |
| 26.5 | 854 | 15.5 |
| 27.5 | 603 | 10.9 |
| 28.1 | 515 | 9.3 |
| 28.9 | 2297 | 43.5 |
| 29.1 | 210 | 3.8 |
| 29.8 | 101 | 1.8 |

Form HIII was characterized by DSC. The DSC was obtained from TA Instruments Differential Scanning Calorimetry, Model Q2000 with autosampler. The DSC instrument conditions are similar to those for Form HI. The DSC thermogram is shown in FIG. 11. The DSC thermogram revealed two major endothermal events. The first event appeared at an onset temperature of 54.3° C. with a peak temperature of 66.8° C. which is believed to be the dehydration of the compound. The second event appeared at an onset temperature of 92.6° C. with a peak temperature of 98.4° C. which is believed to be the melting of the compound.

Form HIII was characterized by TGA. The TGA was obtained from PerkinElmer Thermogravimetric Analyzer, Model Pyris 1. The general experimental conditions for TGA are similar to those for Form HI. The TGA thermogram is shown in FIG. 12. A weight loss of about 4.8% up to 120° C. was observed and is believed to be associated mostly with the loss of water.

Example 9

Preparation and Characterization of Form DH

Form DH was prepared by drying Form HI on Vapor Sorption Analyzer (TA Instruments VTI-SA+) at 25° C. with 0% RH $N_2$ for 2 days. When Form DH is exposed to humidity, it can absorb water and change to Form HIII at about 30-50% RH or to Form HI at high humidity around 60-85% RH.

Form DH was characterized by XRPD. The XRPD was obtained from Bruker D2 PHASER X-ray Powder Diffractometer (XRPD) instrument. The general experimental procedures for XRPD are similar to those for Form HI. The XRPD pattern is shown in FIG. 13 and the XRPD data are provided in Table 5.

TABLE 5

| 2-Theta (°) | Height | H % |
|---|---|---|
| 5.6 | 57.5 | 1.0 |
| 6.1 | 69.2 | 1.2 |
| 6.6 | 62.7 | 1.1 |
| 7.4 | 2956 | 50.0 |
| 7.5 | 3560 | 60.2 |
| 9.6 | 2326 | 39.4 |
| 10.0 | 534 | 9.0 |
| 10.7 | 4068 | 68.8 |
| 12.0 | 128 | 2.2 |
| 12.6 | 95.4 | 1.6 |
| 13.6 | 217 | 3.7 |
| 13.9 | 1487 | 25.2 |
| 14.8 | 1943 | 32.9 |
| 15.5 | 780 | 13.2 |
| 16.0 | 533 | 9.0 |
| 16.1 | 311 | 5.3 |
| 16.6 | 450 | 7.6 |
| 17.2 | 1437 | 24.3 |
| 17.3 | 1675 | 28.3 |
| 18.1 | 1061 | 18.0 |
| 18.3 | 1500 | 25.4 |
| 18.9 | 282 | 4.8 |
| 19.5 | 61.7 | 1.0 |
| 20.1 | 1482 | 25.1 |
| 20.7 | 1423 | 24.1 |
| 21.6 | 1585 | 26.8 |
| 22.1 | 936 | 15.8 |
| 22.9 | 5909 | 100 |
| 23.4 | 588 | 10.0 |
| 24.0 | 955 | 16.2 |
| 24.7 | 3283 | 55.6 |
| 25.3 | 94.8 | 1.6 |
| 25.8 | 754 | 12.7 |
| 26.7 | 721 | 12.2 |

TABLE 5-continued

| 2-Theta (°) | Height | H % |
|---|---|---|
| 27.1 | 433 | 7.3 |
| 28.0 | 335 | 5.7 |
| 28.2 | 322 | 5.4 |
| 29.5 | 200 | 3.4 |

Form DH was characterized by DSC. The DSC was obtained from TA Instruments Differential Scanning Calorimetry, Model Q2000 with autosampler. The DSC instrument conditions similar to those for Form HI. The DSC thermogram is shown in FIG. 14. The DSC thermogram revealed one major endothermal event at an onset temperature of 93.8° C. with a peak temperature of 97.5° C. which is believed to be the melting of the compound.

Form DH was characterized by TGA. The TGA was obtained from PerkinElmer Thermogravimetric Analyzer, Model Pyris 1. The general experimental conditions for TGA are similar to those for Form HI. The TGA thermogram is shown in FIG. 15. A weight loss of about 2.3% up to 120° C. was observed and is believed to be associated mostly with the loss of water.

Form DH was characterized by DVS. The DVS analysis was performed on a TA Instruments Vapor Sorption Analyzer, model VTI-SA+. Form DH was generated by pre-drying Form HI on VTI at 40° C. with 0% RH $N_2$ for 3 h. Then the moisture uptake profile was completed in one cycle in 5% RH increments with adsorption from 0% RH to 95% RH followed by desorption in 5% increments from 95% to 85% RH. The equilibration criteria were 0.0010 wt % in 5 minutes with a maximum equilibration time of 180 minutes. All adsorption and desorption were performed at 25° C.

Figure 18:
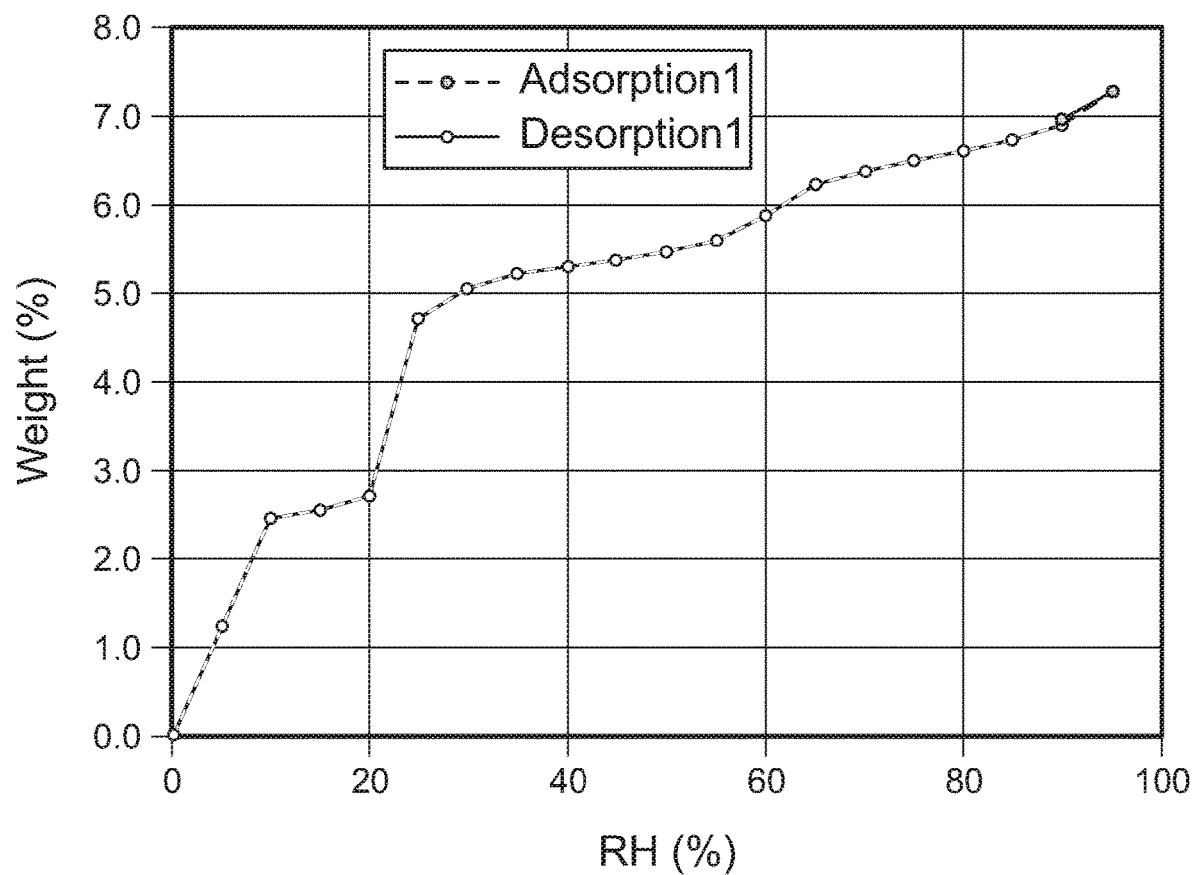
FIG. 18 shows a DVS adsorption-desorption isotherm of Compound I di-tosylate salt, Form DH.

The adsorption/desorption isotherm is shown in FIG. 18. Form DH is hygroscopic and will absorb water stepwise to form different hydrates. The solid collected after DVS at 85% RH is characterized as Form HI.

Example 10

Physical Stability of Form HI

Physical stability of Form HI was studied under different humidity conditions. The humidity was controlled at 25° C. using Vapor Sorption Analyzer (TA Instruments, Model VTI-SA+). Approximately 20 mg of Form HI in the sample holder was placed inside the humidity chamber of the instrument and held under constant humidity. A sample in an open glass vial was also set up under ambient conditions. After a certain period of time, the sample was removed and characterized by XRPD, DSC, and TGA. Weight loss by TGA was mostly associated with loss of water. The experimental parameters of XRPD, DSC, and TGA are analogous to those in Example 6 for Form HI.

Form HI was stable for 10 days under humidity conditions of 10-85% RH and was stable for 60 days under ambient conditions. Form HI was de-hydrated below 10% RH and absorbed water to change to Form HII at 90% RH. The table below provides the data for the physical stability of Form HI at 25° C. (open vial).

TABLE 6

| Humidity (% RH) | Time (Day) | DSC (° C.) (Peak Temperature) | % Wt Loss by TGA (25-120° C.) | XRPD |
|---|---|---|---|---|
| 0 | 2 | 97.5 | 2.30 | Form DH |
| 5 | 7 | 81.2 | 2.93 | Form HI |

TABLE 6-continued

| Humidity (% RH) | Time (Day) | DSC (° C.) (Peak Temperature) | % Wt Loss by TGA (25-120° C.) | XRPD |
|---|---|---|---|---|
| 10 | 10 | 82.4 | 5.05 | Form HI |
| 30 | 5 | 80.7 | 5.38 | Form HI |
| 75 | 10 | 79.8 | 5.30 | Form HI |
| 85 | 10 | 79.9 | 5.35 | Form HI |
| 90 | 4 | 80.0 | 6.04 | Form HI + Form HII (minor) |
|  | 10 | 55.7; 79.1 | 9.4 | Form HI + Form HII |
| Ambient | 60 | 79.8 | 4.77 | Form HI |

Example 11

Phase Equilibration at 25° C. and 50° C.

To a solvent such as chloroform, dimethylformamide (DMF), 1,4-dioxane, methyl isobutyl ketone (MIBK), tetrahydrofuran (THF), acetone, n-BuOH, isobutyl acetate, isopropyl acetate (IPAc), isopropyl alcohol (IPA), water, methyl ethyl ketone (MEK), methanol, 2-methoxyethanol, EtOH, ethyl acetate (EtOAc), ethyl formate, isobutyl acetate, heptane or 1-propanol was added Compound I di-tosylate until a cloudy solution was obtained, then about 30 mg of Compound I di-tosylate was added to the cloudy solution. The mixture was stirred at 25° C. for 3 days and at 50° C. for 2 days. The solid was filtered and analyzed by XRPD and characterized by DSC and TGA. Phase equilibration at 25° C. resulted in Form II (n-BuOH), Form III (IPA), Form IV (water), and amorphous (1,4-dioxane).

Example 12

Evaporation at 25° C. and 50° C.

Evaporation studies of Compound I di-tosylate solutions were carried out in various solvents such as acetonitrile (MeCN), chloroform, dichloromethane, DMF, 1,4-dioxane, methanol, 2-methoxyethanol, MIBK, THF, acetone, n-BuOH, methyl t-butyl ether (MTBE), dimethylsulfoxide (DMSO), EtOH, EtOAc, ethyl formate, isobutyl acetate, IPAc, 1-propanol, water, and MEK at 25±1° C. Form IV (water), Form V (MeCN, 1-propanol), Form VI ($CH_2Cl_2$), and Form VII (EtOH) were discovered. Evaporation at 50±1° C. in the above solvents resulted in Form V (MeCN, EtOH, and 1-propanol), Form VI (2-methoxyethanol and IPA), and Form VIII (n-BuOH).

Example 13

Anti-Solvent Addition

Saturated or almost saturated solutions of Compound I di-tosylate were prepared by adding Compound I di-tosylate to the solvents in Table 7 below. An anti-solvent, such as MTBE, IPAc, heptane, and hexane was added to induce precipitation. The results are presented in Table 7. Anti-solvent addition resulted in Form II (n-BuOH/IPAc), Form III (IPA/hexane, IPA/MTBE, and IPA/heptane), Form IIIa (EtOH/IPAc), Form V (MeCN/MTBE and MeCN/IPAc), Form IX (n-BuOH/MTBE and n-BuOH/heptane), Form X (EtOH/heptane) and amorphous (THF/MTBE, THF/heptane, THF/hexane, MEK/heptane, and MEK/hexane).

TABLE 7

Precipitation from Anti-solvent addition

| Solvent (mL) | Anti-solvent (mL) | Form |
|---|---|---|
| MeCN (0.3) | MTBE (2.0) | V |
| MeCN (0.3) | IPAc (2.0) | V |
| THF* (1.5) | MTBE (3.0) | amorphous |
| THF* (1.0) | Heptane (1.8) | amorphous |
| THF* (1.0) | Hexane (1.5) | amorphous |
| n-BuOH** (0.4) | MTBE (3.5) | IX |
| n-BuOH** (0.4) | Heptane (3.0) | IX |
| n-BuOH** (0.4) | IPAc (3.0) | II**** |
| EtOH*** (0.3) | Heptane (2.5) | X |
| EtOH*** (0.4) | IPAc (3.0) | IIIa |
| IPA (1.0) | Hexane (6.0) | III |
| IPA (1.0) | MTBE (9.0) | III |
| IPA (1.0) | Heptane (6.0) | III |
| MEK* (1.5) | Heptane (1.8) | Amorphous |
| MEK* (1.5) | Hexane (1.8) | Amorphous |

*about 45° C. saturated solution
**about 50 mg/mL of n-BuOH solution
***about 60 mg/mL of ethanol solution
****25 min stirring to give slurry

Example 14

Reverse Addition

Saturated solutions of Compound I di-tosylate were prepared in solvents listed in Table 8 and were added to a larger volume of a miscible anti-solvent. Reverse addition resulted in Form II (n-BuOH/IPAc), Form III (IPA/hexane, IPA/MTBE, and IPA/heptane), Form IIIa (EtOH/IPAc), Form V (MeCN/MTBE and MeCN/IPAc), Form IX (n-BuOH/MTBE and n-BuOH/Heptane), and Form X (EtOH/heptane).

TABLE 8

Precipitation from Reverse addition

| Solvent (mL) | Anti-solvent (mL) | Form |
|---|---|---|
| MeCN (0.5) | MTBE (3.0) | V |
| MeCN (0.5) | IPAc (0.5) | V |
| n-BuOH** (0.3) | MTBE (2.0) | IX |
| n-BuOH** (0.3) | Heptane (2.0) | IX |
| n-BuOH** (0.3) | IPAc (3.5) | II**** |
| EtOH*** (0.3) | Heptane (2.5) | X |
| EtOH*** (0.4) | IPAc (3.0) | IIIa |
| IPA (0.6) | Hexane (3.0) | III |
| IPA (0.6) | MTBE (3.0) | III |
| IPA (0.6) | Heptane (3.0) | III |

*about 45° C. saturated solution
**about 50 mg/mL of n-BuOH solution
***about 60 mg/mL of ethanol solution
****25 min stirring to give slurry

Example 15

Quench Cool of Saturated Solution

Saturated solutions prepared at 35° C. were quench-cooled to about −20° C. to −25° C. The results are shown in Table 9. Quench cooling resulted in Form II (n-BuOH), Form III (IPA), Form V (MeCN), and Form XI (1-propanol).

TABLE 9

Polymorphism Identification from Quench Cool

| Solvent | Solid State Form |
|---|---|
| MeCN | V |
| n-BuOH | II |
| 1-Propanol | XI |
| IPA | III |

Example 16

Crystallization of Saturated Solution with Heating and Cooling Cycles

Saturated solutions of Compound I di-tosylate were prepared at 50° C., and cooled in a bath slowly by using a programmed circulating bath. To the clear solution of Compound I di-tosylate was added about 20-30 mg of Compound I di-tosylate Form I to give a slurry. The formed slurry was then heated to 50° C. over 2 hours and then cooled down to 5° C. over 2 hours. This process was repeated for 3 days and the resulting solid was filtered for further analysis. The results are in Table 10. Heating and cooling resulted in Form I (EtOAc, MEK, and MEK/heptane), Form IV (water), and Form XII (acetone and IPA).

TABLE 10

Crystallization of Saturated Solution

| Solvent | Solid State Form |
|---|---|
| Acetone | XII |
| Ethyl acetate | I |
| IPA | XII |
| Water | IV |
| MEK | I |
| MEK/Heptane (2:1) | I |

Example 17

Preparation and Characterization of Form II

In one experiment, Form II was prepared by adding about 60 mg of Form I to 3 mL of saturated or cloudy solution of Form I in n-butanol. The resulting mixture was stirred at 25±1° C. for 3 days. The resulting solid was filtered. Form II was also prepared in accordance with the procedures set forth in Examples 13, 14 and 15 in n-BuOH/IPAc, n-BuOH/IPAc and n-BuOH, respectively.

Form II was characterized by XRPD. The XRPD was obtained using similar conditions as those for Form I. The XRPD pattern is shown in FIG. 19 and the XRPD data are provided

TABLE 11

| 2-Theta | Height | H % |
|---|---|---|
| 5.1 | 265 | 17.3 |
| 6.8 | 930 | 60.5 |
| 9.0 | 46 | 3.0 |
| 10.2 | 207 | 13.5 |
| 14.2 | 229 | 14.9 |
| 15.8 | 213 | 13.9 |
| 17.7 | 219 | 14.3 |
| 20.4 | 477 | 31.1 |
| 22.0 | 220 | 14.3 |
| 23.3 | 1536 | 100 |
| 24.3 | 301 | 19.6 |

TABLE 11-continued

| 2-Theta | Height | H % |
|---|---|---|
| 26.9 | 564 | 36.7 |
| 28.5 | 54 | 3.5 |
| 29.3 | 69 | 4.5 |
| 30.1 | 205 | 13.3 |
| 30.8 | 86 | 5.6 |
| 33.6 | 88 | 5.7 |
| 35.6 | 79 | 5.1 |
| 39.0 | 61 | 4.0 |
| 41.5 | 81 | 5.3 |
| 44.2 | 45 | 2.9 |

Form II was characterized by DSC. The DSC was obtained using similar conditions as those for Form I. The DSC thermogram is shown in FIG. 20. The DSC thermogram revealed an endothermic event at an onset temperature of 74.0° C. with a peak temperature of 77.8° C. and an exothermic event with an onset temperature 149.3° C. with a peak temperature of 185.0° C.

Form II was characterized by TGA. The TGA was obtained using similar conditions as Form I. The TGA thermogram is shown in FIG. 21.

Example 18

Preparation and Characterization of Form III

In one experiment, Form III was prepared by adding about 50 mg of Form I to about 3 mL of saturated or cloudy solution of Form I in IPA followed by stirring at 25±1° C. for 3 days. The resulting solid was filtered. Form III was also prepared according to the procedures set forth in Examples 13, 14 and 15 using IPA/hexane, IPA/heptane or IPA/MTBE as a solvent pair in antisolvent addition; IPA/hexane, IPA/MTBE or IPA/heptane as a solvent pair in reverse addition; and IPA in quench cooling.

Form III was characterized by XRPD. The XRPD was obtained using similar conditions as those for Form I. The XRPD pattern is shown in FIG. 22 and the XRPD data are provided in Table 12.

TABLE 12

| 2-Theta | Height | H % |
|---|---|---|
| 4.6 | 2943 | 70.2 |
| 5.2 | 4194 | 100 |
| 6.5 | 203 | 4.8 |
| 8.2 | 141 | 3.4 |
| 9.2 | 299 | 7.1 |
| 10.3 | 234 | 5.6 |
| 11.4 | 32 | 0.8 |
| 14.0 | 304 | 7.2 |
| 15.4 | 160 | 3.8 |
| 16.3 | 287 | 6.8 |
| 18.4 | 390 | 9.3 |
| 18.9 | 59 | 1.4 |
| 19.6 | 183 | 4.4 |
| 20.2 | 46 | 1.1 |
| 20.7 | 188 | 4.5 |
| 22.2 | 222 | 5.3 |
| 22.8 | 1027 | 24.5 |
| 24.2 | 565 | 13.5 |
| 26.4 | 110 | 2.6 |
| 27.4 | 94 | 2.2 |
| 28.0 | 40 | 1.0 |
| 29.2 | 54 | 1.3 |
| 30.9 | 118 | 2.8 |
| 32.7 | 44 | 1.0 |
| 33.1 | 60 | 1.4 |

TABLE 12-continued

| 2-Theta | Height | H % |
|---|---|---|
| 37.5 | 33 | 0.8 |
| 42.5 | 31 | 0.7 |

Form III was characterized by DSC. The DSC was obtained using similar conditions as those for Form I. The DSC thermogram is shown in FIG. 23. The DSC thermogram revealed an endothermic event at an onset temperature of 73.5° C. with a peak temperature of 79.6° C. and an exothermic event with an onset temperature 152.5° C. with a peak temperature of 181.0° C.

Form III was characterized by TGA. The TGA was obtained using similar conditions as Form I. The TGA thermogram is shown in FIG. 24.

Example 19

Preparation and Characterization of Form IIIa

In one experiment, Form IIIa was prepared by adding 0.4 mL of saturated solution of Form I in ethanol (60 mg/mL) to 3.0 mL of IPAc. The resulting solid was filtered. Form IIIa was also prepared according to the procedure set forth in Example 13 using EtOH/IPAc as a solvent pair.

Form IIIa was characterized by XRPD. The XRPD was obtained using similar conditions as those for Form I. The XRPD pattern is shown in FIG. 25 and the XRPD data are provided in Table 13.

TABLE 13

| 2-Theta | Height | H % |
|---|---|---|
| 4.5 | 1206 | 56.7 |
| 5.1 | 2128 | 100 |
| 6.9 | 856 | 40.2 |
| 8.1 | 400 | 18.8 |
| 9.2 | 138 | 6.5 |
| 10.1 | 537 | 25.2 |
| 11.3 | 88 | 4.1 |
| 13.5 | 183 | 8.6 |
| 14.1 | 140 | 6.6 |
| 14.6 | 59 | 2.8 |
| 15.2 | 144 | 6.8 |
| 16.3 | 359 | 16.9 |
| 17.8 | 229 | 10.8 |
| 18.3 | 185 | 8.7 |
| 19.4 | 132 | 6.2 |
| 20.8 | 484 | 22.7 |
| 21.4 | 230 | 10.8 |
| 22.2 | 559 | 26.3 |
| 22.7 | 1493 | 70.2 |
| 24.1 | 756 | 35.5 |
| 25.2 | 81 | 3.8 |
| 25.7 | 58 | 2.7 |
| 26.4 | 140 | 6.6 |
| 27.3 | 125 | 5.9 |
| 29.1 | 91 | 4.3 |
| 30.7 | 70 | 3.3 |
| 31.4 | 48 | 2.3 |
| 32.9 | 57 | 2.7 |

Example 20

Preparation and Characterization of Form IV

In one experiment, Form IV was prepared by adding about 50 mg of Form I to about 3 mL of saturated or cloudy solution of Form I in water followed by stirring at 25±1° C. for 3 days. The resulting solid was filtered and air-dried in hood for 4 days. Form IV was also prepared according to the procedures set forth in Examples 12 and 16 using water as a solvent.

Form IV was characterized by XRPD. The XRPD was obtained using similar conditions as those for Form I. The XRPD pattern is shown in FIG. 26 and the XRPD data are provided in Table 14.

TABLE 14

| 2-Theta | Height | H % |
|---|---|---|
| 7.1 | 186 | 93.5 |
| 8.9 | 63 | 31.7 |
| 10.5 | 70 | 35.2 |
| 14.6 | 100 | 50.3 |
| 15.2 | 55 | 27.6 |
| 18.0 | 107 | 53.8 |
| 18.5 | 63 | 31.7 |
| 20.6 | 102 | 51.3 |
| 20.9 | 123 | 61.8 |
| 21.7 | 68 | 34.2 |
| 22.3 | 61 | 30.7 |
| 23.1 | 199 | 100 |
| 24.8 | 191 | 96.0 |
| 27.5 | 76 | 38.2 |
| 28.8 | 146 | 73.4 |
| 30.4 | 50 | 25.1 |
| 32.5 | 43 | 21.6 |

Form IV was characterized by DSC. The DSC was obtained using similar conditions as those for Form I. The DSC thermogram is shown in FIG. 27. The DSC thermogram revealed endothermic events at an onset temperature of 49.1° C. with a peak temperature of 53.6° C. and at peak temperature of 125.1. The DSC thermogram also revealed an exothermic event with an onset temperature 153.5° C. with a peak temperature of 171.1° C.

Form IV was characterized by TGA. The TGA was obtained using similar conditions as Form I. The TGA thermogram is shown in FIG. 28.

Example 21

Preparation and Characterization of Form IVa

Form IVa was prepared by drying Form IV under vacuum at 45-50° C. overnight and air-dried for 28 days.

Form IVa was characterized by XRPD. The XRPD was obtained using similar conditions as those for Form I. The XRPD pattern is shown in FIG. 29 and the XRPD data are provided in Table 15.

TABLE 15

| 2-Theta | Height | H % |
|---|---|---|
| 6.4 | 1419 | 82.2 |
| 6.9 | 1727 | 100 |
| 8.7 | 349 | 20.2 |
| 10.1 | 927 | 53.7 |
| 11.0 | 40 | 2.3 |
| 13.8 | 134 | 7.8 |
| 14.4 | 668 | 38.7 |
| 14.7 | 96 | 5.6 |
| 15.6 | 130 | 7.5 |
| 16.5 | 56 | 3.2 |
| 17.5 | 90 | 5.2 |
| 17.8 | 80 | 4.6 |
| 18.3 | 47 | 2.7 |
| 20.1 | 63 | 3.6 |
| 20.7 | 328 | 19.0 |
| 20.9 | 175 | 10.1 |
| 21.6 | 239 | 13.8 |
| 22.1 | 547 | 31.7 |
| 22.8 | 1373 | 79.5 |
| 23.3 | 83 | 4.8 |
| 23.7 | 68 | 3.9 |
| 24.4 | 1657 | 95.9 |
| 24.7 | 554 | 32.1 |
| 25.1 | 53 | 3.1 |
| 25.6 | 69 | 4.0 |
| 26.2 | 79 | 4.6 |
| 27.2 | 130 | 7.5 |
| 27.8 | 111 | 6.4 |
| 28.5 | 630 | 36.5 |
| 29.0 | 68 | 3.9 |
| 29.6 | 40 | 2.3 |
| 30.2 | 147 | 8.5 |
| 31.2 | 62 | 3.6 |
| 31.4 | 168 | 9.7 |
| 32.1 | 136 | 7.9 |
| 32.6 | 97 | 5.6 |
| 33.3 | 58 | 3.4 |
| 34.6 | 98 | 5.7 |
| 35.9 | 138 | 8.0 |
| 36.6 | 64 | 3.7 |
| 38.0 | 39 | 2.3 |
| 39.0 | 84 | 4.9 |
| 39.6 | 53 | 3.1 |
| 40.9 | 75 | 4.3 |
| 41.3 | 64 | 3.7 |
| 42.2 | 68 | 3.9 |
| 42.7 | 75 | 4.3 |
| 44.1 | 44 | 2.5 |

Form IVa was characterized by DSC. The DSC was obtained using similar conditions as those for Form I. The DSC thermogram is shown in FIG. 30. The DSC thermogram revealed an endothermic event at an onset temperature of 50.1° C. with a peak temperature of 53.3° C. and an exothermic event with a peak temperature of 182.9° C.

Form IVa was characterized by TGA. The TGA was obtained using similar conditions as Form I. The TGA thermogram is shown in FIG. 31.

Example 22

Preparation and Characterization of Form V

In one experiment, Form V was prepared by evaporating approximately 2 mL of saturated solution of Form I in acetonitrile under air without stirring at 25±1° C. Form V was also prepared according to the procedure set forth in Example 11 by evaporating a solution of compound I in MeCN, EtOH or 1-propanol at 50° C. In other experiments, Form V was prepared according to the procedures set forth in Examples 13, 14 and 15 using MeCN/MTBE or MeCN/IPAc as a solvent pair in antisolvent addition; MeCN/MTBE, MeCN/IPAc as a solvent pair in reverse addition; and MeCN in quench cooling Form V was characterized by XRPD. The XRPD was obtained using similar conditions as those for Form I. The XRPD pattern is shown in FIG. 32 and the XRPD data are provided in Table 16.

TABLE 16

| 2-Theta | Height | H % |
|---|---|---|
| 5.6 | 772 | 43.5 |
| 7.3 | 1773 | 100 |
| 9.4 | 147 | 8.3 |
| 10.8 | 464 | 26.2 |
| 14.1 | 71 | 4.0 |
| 14.8 | 261 | 14.7 |
| 15.9 | 259 | 14.6 |
| 16.7 | 484 | 27.3 |
| 17.6 | 501 | 28.3 |

TABLE 16-continued

| 2-Theta | Height | H % |
|---|---|---|
| 18.3 | 187 | 10.5 |
| 19.3 | 201 | 11.3 |
| 20.1 | 368 | 20.8 |
| 21.2 | 1293 | 72.9 |
| 21.6 | 696 | 39.3 |
| 23.3 | 383 | 21.6 |
| 24.3 | 870 | 49.1 |
| 25.4 | 324 | 18.3 |
| 25.9 | 69 | 3.9 |
| 26.9 | 323 | 18.2 |
| 27.9 | 190 | 10.7 |
| 29.8 | 191 | 10.8 |
| 30.6 | 105 | 5.9 |
| 31.3 | 109 | 6.1 |
| 31.7 | 97 | 5.5 |
| 32.5 | 142 | 8.0 |
| 33.3 | 78 | 4.4 |
| 34.0 | 60 | 3.4 |
| 37.0 | 89 | 5.0 |
| 38.2 | 93 | 5.2 |
| 39.8 | 167 | 9.4 |
| 41.9 | 56 | 3.2 |
| 42.6 | 83 | 4.7 |
| 44.0 | 79 | 4.5 |

Form V was characterized by DSC. The DSC was obtained using similar conditions as those for Form I. The DSC thermogram is shown in FIG. 33. The DSC thermogram revealed endothermic events at an onset temperature of 47.4° C. with a peak temperature of 52.9° C. and an onset temperature at about 72.3° C. with a peak temperature of 82.9° C. The DSC thermogram also revealed an exothermic event at an onset temperature of 176.7° C. with a peak temperature of 184.8° C.

Form V was characterized by TGA. The TGA was obtained using similar conditions as Form I. The TGA thermogram is shown in FIG. 34.

Example 23

Preparation and Characterization of Form VI

In one experiment, Form VI was prepared by evaporating approximately 2 mL of saturated solution of Form I in dichloromethane under air without stirring at 25±1° C. Form VI was also prepared according to the procedure set forth in Example 11 by evaporating a solution of Compound I in 2-methoxyethanol or IPA at 50° C.

Form VI was characterized by XRPD. The XRPD was obtained using similar conditions as those for Form I. The XRPD pattern is shown in FIG. 35 and the XRPD data are provided in Table 17.

TABLE 17

| 2-Theta | Height | H % |
|---|---|---|
| 5.6 | 63 | 3.0 |
| 7.4 | 308 | 14.5 |
| 9.4 | 75 | 3.5 |
| 9.7 | 84 | 3.9 |
| 10.9 | 280 | 13.2 |
| 14.1 | 310 | 14.6 |
| 14.6 | 78 | 3.7 |
| 16.0 | 268 | 12.6 |
| 17.1 | 386 | 18.1 |
| 17.7 | 262 | 12.3 |
| 18.3 | 179 | 8.4 |
| 19.1 | 222 | 10.4 |
| 20.4 | 579 | 27.2 |
| 21.3 | 1059 | 49.7 |

TABLE 17-continued

| 2-Theta | Height | H % |
|---|---|---|
| 22.0 | 228 | 10.7 |
| 22.8 | 1291 | 60.6 |
| 23.5 | 542 | 25.5 |
| 24.5 | 2129 | 100 |
| 25.7 | 423 | 19.9 |
| 27.2 | 166 | 7.8 |
| 27.8 | 119 | 5.6 |
| 28.6 | 400 | 18.8 |
| 30.3 | 446 | 20.9 |
| 31.8 | 313 | 14.7 |
| 32.8 | 206 | 9.7 |
| 33.8 | 120 | 5.6 |
| 35.1 | 203 | 9.5 |
| 36.8 | 207 | 9.7 |
| 38.5 | 237 | 11.1 |
| 41.5 | 107 | 5.0 |
| 42.7 | 251 | 11.8 |

Form VI was characterized by DSC. The DSC was obtained using similar conditions as those for Form I. The DSC thermogram is shown in FIG. 36. The DSC thermogram revealed an endothermic event at an onset temperature of 66.5° C. with a peak temperature of 82.1° C. and an exothermic event at an onset temperature of 148.5° C. with a peak temperature of 184.9° C.

Form VI was characterized by TGA. The TGA was obtained using similar conditions as Form I. The TGA thermogram is shown in FIG. 37.

Example 24

Preparation and Characterization of Form VII

Form VII was prepared by evaporating approximately 2 mL of saturated solution of Form I in ethanol under air without stirring at 25±1° C.

Form VII was characterized by XRPD. The XRPD was obtained using similar conditions as those for Form I. The XRPD pattern is shown in FIG. 38 and the XRPD data are provided in Table 18.

TABLE 18

| 2-Theta | Height | H % |
|---|---|---|
| 11.0 | 65 | 4.1 |
| 14.4 | 145 | 9.2 |
| 16.3 | 71 | 4.5 |
| 17.2 | 255 | 16.1 |
| 18.0 | 78 | 4.9 |
| 18.5 | 124 | 7.8 |
| 19.3 | 102 | 6.4 |
| 21.6 | 786 | 49.7 |
| 23.0 | 802 | 50.7 |
| 23.8 | 256 | 16.2 |
| 24.8 | 1582 | 100 |
| 25.6 | 229 | 14.5 |
| 26.0 | 366 | 23.1 |
| 26.4 | 251 | 15.9 |
| 27.5 | 95 | 6.0 |
| 28.9 | 142 | 9.0 |
| 30.1 | 190 | 12.0 |
| 30.5 | 334 | 21.1 |
| 32.1 | 190 | 12.0 |
| 33.0 | 143 | 9.0 |
| 34.2 | 77 | 4.9 |
| 34.9 | 102 | 6.4 |
| 35.4 | 226 | 14.3 |
| 37.2 | 170 | 10.7 |
| 38.9 | 144 | 9.1 |
| 40.2 | 96 | 6.1 |
| 40.9 | 69 | 4.4 |

TABLE 18-continued

| 2-Theta | Height | H % |
|---|---|---|
| 41.6 | 82 | 5.2 |
| 42.6 | 115 | 7.3 |
| 43.0 | 177 | 11.2 |

Form VII was characterized by DSC. The DSC was obtained using similar conditions as those for Form I. The DSC thermogram is shown in FIG. 39. The DSC thermogram revealed an endothermic event at an onset temperature of 81.2° C. with a peak temperature of 90.3° C. and an exothermic event at an onset temperature of 148.8° C. with a peak temperature of 184.9° C.

Form VII was characterized by TGA. The TGA was obtained using similar conditions as Form I. The TGA thermogram is shown in FIG. 40.

Example 25

Preparation and Characterization of Form VIII

Form VIII was prepared by evaporating approximately 2 mL of saturated solution of Form I in n-butanol under air without stirring at 50±1° C.

Form VIII was characterized by XRPD. The XRPD was obtained using similar conditions as those for Form I. The XRPD pattern is shown in FIG. 41 and the XRPD data are provided in Table 19.

TABLE 19

| 2-Theta | Height | H % |
|---|---|---|
| 7.2 | 646 | 24.4 |
| 9.4 | 49 | 1.8 |
| 10.6 | 186 | 7.0 |
| 14.7 | 252 | 9.5 |
| 15.8 | 163 | 6.2 |
| 16.3 | 924 | 34.9 |
| 17.5 | 380 | 14.3 |
| 18.1 | 340 | 12.8 |
| 19.0 | 83 | 3.1 |
| 20.7 | 986 | 37.2 |
| 21.5 | 919 | 34.7 |
| 22.6 | 777 | 29.3 |
| 23.8 | 2650 | 100 |
| 24.8 | 1020 | 38.5 |
| 25.7 | 185 | 7.0 |
| 27.4 | 1366 | 51.5 |
| 29.4 | 452 | 17.1 |
| 30.4 | 487 | 18.4 |
| 31.2 | 163 | 6.2 |
| 32.2 | 279 | 10.5 |
| 33.1 | 112 | 4.2 |
| 33.8 | 321 | 12.1 |
| 36.1 | 215 | 8.1 |
| 37.2 | 143 | 5.4 |
| 39.4 | 216 | 8.2 |
| 40.5 | 143 | 5.4 |
| 41.9 | 297 | 11.2 |
| 43.2 | 159 | 6.0 |

Form VIII was characterized by DSC. The DSC was obtained using similar conditions as those for Form I. The DSC thermogram is shown in FIG. 42. The DSC thermogram revealed an endothermic event at an onset temperature of 69.7° C. with a peak temperature of 74.7° C. and an exothermic event at an onset temperature of 157.0° C. with a peak temperature of 185.9° C.

Form VIII was characterized by TGA. The TGA was obtained using similar conditions as Form I. The TGA thermogram is shown in FIG. 43.

Example 26

Preparation and Characterization of Form IX

In one experiment, Form IX was prepared by adding 0.3 mL of a solution of Form I in n-butanol (50 mg/mL) to 2.0 mL of heptane followed by stirring for about 5 min. The resulting solid was filtered. Form IX was also prepared according to the procedure set forth in Example 13 using n-BuOH/MTBE or n-BuOH/heptane as a solvent pair.

Form IX was characterized by XRPD. The XRPD was obtained using similar conditions as those for Form I. The XRPD pattern is shown in FIG. 44 and the XRPD data are provided in Table 20.

TABLE 20

| 2-Theta | Height | H % |
|---|---|---|
| 3.3 | 36 | 1.1 |
| 5.3 | 3233 | 100 |
| 6.9 | 73 | 2.3 |
| 10.5 | 498 | 15.4 |
| 15.7 | 252 | 7.8 |
| 16.3 | 612 | 18.9 |
| 21.0 | 309 | 9.6 |
| 21.4 | 366 | 11.3 |
| 22.8 | 118 | 3.6 |
| 25.0 | 29 | 0.9 |
| 26.7 | 454 | 14.0 |
| 27.8 | 50 | 1.5 |
| 32.0 | 156 | 4.8 |
| 33.0 | 27 | 0.8 |
| 37.1 | 25 | 0.8 |
| 38.3 | 31 | 1.0 |

Form IX was characterized by DSC. The DSC was obtained using similar conditions as those for Form I. The DSC thermogram is shown in FIG. 45. The DSC thermogram revealed an endothermic event at an onset temperature of 76.6° C. with a peak temperature of 81.9° C. and an exothermic event at an onset temperature of 154.4° C. with a peak temperature of 185.9° C.

Form IX was characterized by TGA. The TGA was obtained using similar conditions as Form I. The TGA thermogram is shown in FIG. 46.

Example 27

Preparation and Characterization of Form X

In one experiment, Form X was prepared by adding 0.3 mL of saturated solution of Form I in ethanol (60 mg/mL) to 2.5 mL of heptane. The resulting solid was filtered. Form X was also prepared according to the procedure set forth in Example 13 using EtOH/heptane as a solvent pair.

Form X was characterized by XRPD. The XRPD was obtained using similar conditions as those for Form I. The XRPD pattern is shown in FIG. 47 and the XRPD data are provided in Table 21.

TABLE 21

| 2-Theta | Height | H % |
|---|---|---|
| 5.3 | 2417 | 45.7 |
| 6.9 | 5290 | 100 |
| 9.0 | 289 | 5.5 |
| 10.4 | 1236 | 23.4 |
| 11.4 | 96 | 1.8 |
| 13.8 | 148 | 2.8 |
| 14.5 | 782 | 14.8 |
| 15.7 | 179 | 3.4 |

TABLE 21-continued

| 2-Theta | Height | H % |
|---|---|---|
| 16.4 | 1610 | 30.4 |
| 18.0 | 677 | 12.8 |
| 18.8 | 137 | 2.6 |
| 20.8 | 3645 | 68.9 |
| 21.5 | 551 | 10.4 |
| 22.9 | 991 | 18.7 |
| 23.2 | 254 | 4.8 |
| 24.0 | 2250 | 42.5 |
| 25.0 | 978 | 18.5 |
| 26.7 | 618 | 11.7 |
| 27.6 | 291 | 5.5 |
| 29.7 | 65 | 1.2 |
| 31.0 | 176 | 3.3 |
| 31.5 | 288 | 5.4 |
| 32.1 | 471 | 8.9 |
| 33.0 | 85 | 1.6 |
| 34.6 | 80 | 1.5 |
| 36.7 | 200 | 3.8 |
| 38.4 | 55 | 1.0 |
| 39.7 | 152 | 2.9 |
| 41.7 | 125 | 2.4 |

Form X was characterized by DSC. The DSC was obtained using similar conditions as those for Form I. The DSC thermogram is shown in FIG. 48. The DSC thermogram revealed an endothermic event at an onset temperature of 73.8° C. with a peak temperature of 79.2° C. and an exothermic event at an onset temperature of 149.7° C. with a peak temperature of 185.1° C.

Form X was characterized by TGA. The TGA was obtained using similar conditions as Form I. The TGA thermogram is shown in FIG. 49.

Example 28

Preparation and Characterization of Form XI

Form XI was prepared as follows. About 2.0 mL of saturated solution of Form I in n-propanol was cooled to −20° C. and kept at −20° C. for 1 h to give slurry. The resulting solid was filtered and air-dried for 1 h.

Form XI was characterized by XRPD. The XRPD was obtained using similar conditions as those for Form I. The XRPD pattern is shown in FIG. 50 and the XRPD data are provided in Table 22.

TABLE 22

| 2-Theta | Height | H % |
|---|---|---|
| 5.1 | 5949 | 100 |
| 6.7 | 2049 | 34.4 |
| 10.1 | 104 | 1.7 |
| 11.2 | 49 | 0.8 |
| 14.1 | 69 | 1.2 |
| 15.5 | 466 | 7.8 |
| 16.1 | 1975 | 33.2 |
| 17.0 | 238 | 4.0 |
| 17.4 | 46 | 0.8 |
| 17.8 | 255 | 4.3 |
| 18.7 | 59 | 1.0 |
| 19.6 | 99 | 1.7 |
| 20.3 | 448 | 7.5 |
| 20.7 | 2654 | 44.6 |
| 21.1 | 1098 | 18.5 |
| 22.5 | 1000 | 16.8 |
| 22.8 | 90 | 1.5 |
| 23.4 | 892 | 15.0 |
| 24.6 | 388 | 6.5 |
| 24.9 | 95 | 1.6 |
| 25.9 | 491 | 8.3 |
| 26.3 | 226 | 3.8 |

TABLE 22-continued

| 2-Theta | Height | H % |
|---|---|---|
| 26.8 | 63 | 1.1 |
| 27.4 | 631 | 10.6 |
| 29.2 | 168 | 2.8 |
| 30.3 | 152 | 2.6 |
| 30.7 | 45 | 0.8 |
| 31.2 | 91 | 1.5 |
| 31.6 | 473 | 8.0 |
| 32.3 | 90 | 1.5 |
| 32.6 | 96 | 1.6 |
| 34.0 | 172 | 2.9 |
| 36.0 | 45 | 0.8 |
| 36.6 | 416 | 7.0 |
| 37.7 | 101 | 1.7 |
| 39.1 | 71 | 1.2 |
| 40.9 | 115 | 1.9 |
| 43.2 | 62 | 1.0 |
| 44.3 | 115 | 1.9 |

Form XI was characterized by DSC. The DSC was obtained using similar conditions as those for Form I. The DSC thermogram is shown in FIG. 51. The DSC thermogram revealed an endothermic event at an onset temperature of 77.3° C. with a peak temperature of 82.1° C. and an exothermic event at an onset temperature of 153.7° C. with a peak temperature of 185.7° C.

Form XI was characterized by TGA. The TGA was obtained using similar conditions as Form I. The TGA thermogram is shown in FIG. 52.

Example 29

Preparation and Characterization of Form XII

Form XII was prepared as follows. Approximately 7 mL of saturated solution of Form I in acetone was prepared at about 30° C. and cooled to 25° C. in a bath slowly by using a programmed circulating bath. The resulting solution was heated to 50° C. over 2 hours and then cooled to 5° C. over 2 hours, and this process was repeated for 80 hrs. The resulting solid was filtered and air-dried.

Form XII was characterized by XRPD. The XRPD was obtained using similar conditions as those for Form I. The XRPD pattern is shown in FIG. 53 and the XRPD data are provided in Table 23.

TABLE 23

| 2-Theta | Height | H % |
|---|---|---|
| 5.1 | 956 | 80.3 |
| 6.8 | 1190 | 100 |
| 8.8 | 120 | 10.1 |
| 9.2 | 140 | 11.8 |
| 10.3 | 345 | 29.0 |
| 13.5 | 264 | 22.2 |
| 14.0 | 74 | 6.2 |
| 15.4 | 331 | 27.8 |
| 16.5 | 262 | 22.0 |
| 17.2 | 260 | 21.8 |
| 17.8 | 115 | 9.7 |
| 18.6 | 155 | 13.0 |
| 19.7 | 267 | 22.4 |
| 20.1 | 231 | 19.4 |
| 20.8 | 633 | 53.2 |
| 21.3 | 69 | 5.8 |
| 21.7 | 192 | 16.1 |
| 22.2 | 750 | 63.0 |
| 23.0 | 243 | 20.4 |
| 23.9 | 1072 | 90.1 |
| 25.2 | 140 | 11.8 |
| 25.5 | 105 | 8.8 |

TABLE 23-continued

| 2-Theta | Height | H % |
|---------|--------|-----|
| 25.9 | 81 | 6.8 |
| 26.7 | 83 | 7.0 |
| 27.2 | 55 | 4.6 |
| 28.1 | 180 | 15.1 |
| 28.7 | 45 | 3.8 |
| 29.2 | 47 | 3.9 |
| 29.8 | 156 | 13.1 |
| 31.2 | 120 | 10.1 |
| 32.3 | 61 | 5.1 |
| 34.6 | 65 | 5.5 |
| 36.3 | 70 | 5.9 |
| 37.5 | 45 | 3.8 |
| 38.1 | 70 | 5.9 |
| 41.0 | 41 | 3.4 |
| 42.2 | 56 | 4.7 |

Form XII was characterized by DSC. The DSC was obtained using similar conditions as those for Form I. The DSC thermogram is shown in FIG. 54. The DSC thermogram revealed an endothermic event at an onset temperature of 73.9° C. with a peak temperature of 80.5° C. and an exothermic event at an onset temperature of 153.8° C. with a peak temperature of 185.2° C.

Form XII was characterized by TGA. The TGA was obtained using similar conditions as Form I. The TGA thermogram is shown in FIG. 55.

Example 30

Preparation and Characterization of Amorphous Solid

In one experiment, the amorphous solid of Compound I di-tosylate salt was prepared as follows. To about 3 mL of saturated or cloudy solution of Form I in 1,4-dioxane was added about 30 mg of Form I followed by stirring at 25±1° C. for 2 days. The resulting solid was filtered. The amorphous form of Compound I di-tosylate salt was also prepared according to the procedure set forth in Example 13 using THF/heptane, THF/MTBE, THF/hexane, MEK/heptane or MEK/hexane as a solvent pair.

Figure 56:
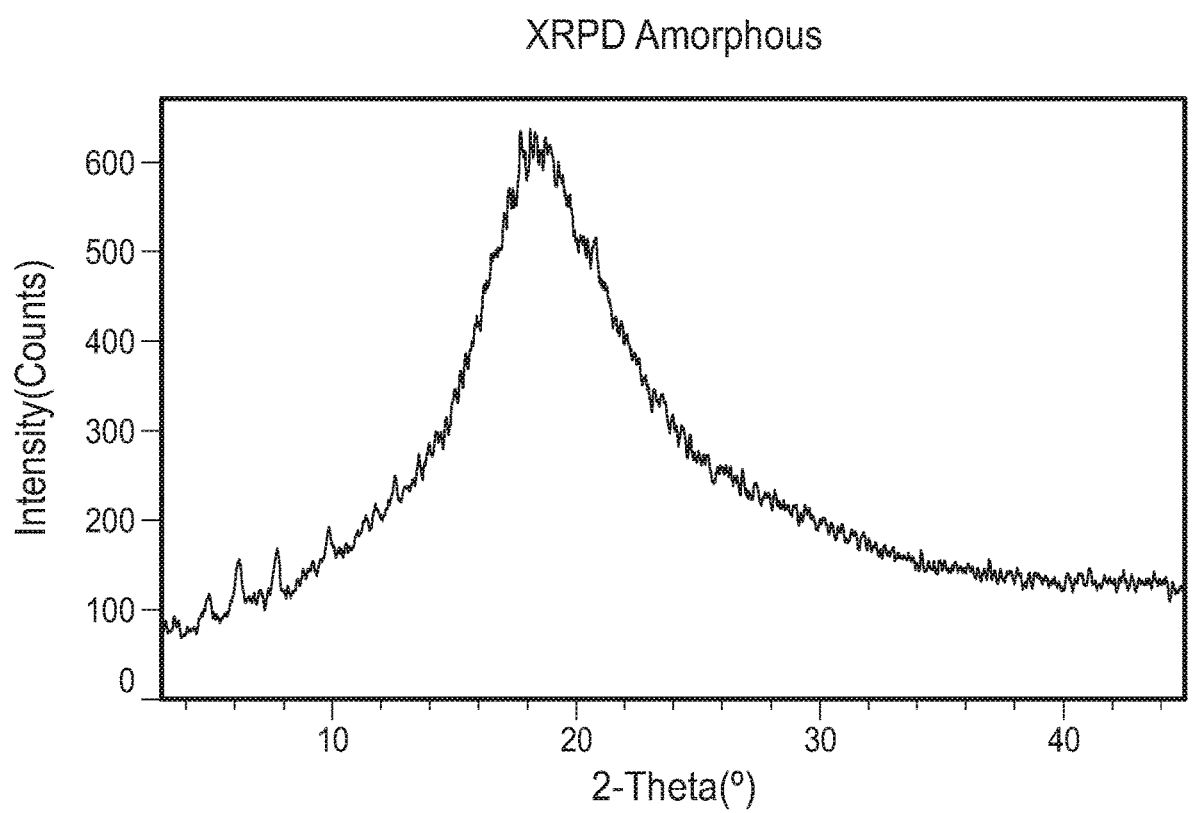
FIG. 56 shows an XRPD pattern of amorphous Compound I di-tosylate salt.

The amorphous solid was characterized by XRPD. The XRPD was obtained using similar conditions as those for Form I. The XRPD pattern is shown in FIG. 56.

Example 31

Stability of Polymorphic Forms

In order to evaluate the relative stability relationship of the various Compound I di-tosylate polymorph forms, a competitive slurry experiment with a mixture of Form I, II, III and IIIa through Form XII was conducted in butanone-heptane at 50° C. according to Procedure 1 below and in butanone at 25° C. according to Procedure 2 below. The mixture of thirteen polymorphs was converted to Form I after stirring in butanone/heptane (1:1) at 50° C. for 6-18 hours and after stirring in butanone at 25° C. for 6-18 hours. These results indicate that the Form I is the most stable polymorphic form in butanone and butanone/heptane (1:1).

Procedure 1 competitive experiment in butanone-heptane at 50° C.:

| No. | Operation |
|-----|-----------|
| 1 | Added 2.5 mL of saturated solution of Compound I di-tosylate in butanone-heptane (1:1) to a 4 mL vial. |
| 2 | Added 3 mg of Compound I di-tosylate Form I to the solution in the step 1, and stirred the resulting mixture to give a cloudy solution. |
| 3 | To the cloudy solution of step 2 was added a mixture of 3 mg each of Compound I polymorphs (Form II, III, IIIa, IV, V, VI, VII, VIII, IX, X, XI, and XII). |
| 4 | Stirred the slurry of step 3 for 6 h at 50° C.: partial slurry was filtered and analyzed by XRPD, which showed Form I. |
| 5 | Stirred the slurry in the step 3 for 18 h at 50° C.: partial slurry was filtered and analyzed by XRPD, which showed Form I. |

Procedure 2 competitive experiment in butanone at 25° C.:

| No. | Operation |
|-----|-----------|
| 1 | Added 2.5 mL of saturated solution of Compound I di-tosylate in butanone to a 4 mL vial. |
| 2 | Added 3 mg of Compound I di-tosylate Form I to the solution in the step 1, and stirred the resulting mixture to give a cloudy solution. |
| 3 | To the cloudy solution of step 2 was added a mixture of 3 mg each of Compound I polymorphs (Form II, III, IIIa, IV, V, VI, VII, VIII, IX, X, XI, and XII). |
| 4 | Stirred the slurry in the step 3 for 6 h at 25° C.: partial slurry was filtered and analyzed by XRPD, which showed Form I. |
| 5 | Stirred the slurry in the step 3 for 18 h at 25° C.: partial slurry was filtered and analyzed by XRPD, which showed Form I. |

Example A: LSD1 Histone Demethylase Biochemical Assay

LANCE LSD1/KDM1A demethylase assay –10 µL of 1 nM LSD-1 enzyme (ENZO BML-SE544-0050) in the assay buffer (50 mM Tris, pH 7.5, 0.01% Tween-20, 25 mM NaCl, 5 mM DTT) were pre-incubated for 1 hour at 25° C. with 0.8 µL compound/DMSO dotted in black 384 well polystyrene plates. Reactions were started by addition of 10 µL of assay buffer containing 0.4 µM Biotin-labeled Histone H3 peptide substrate: ART-K(Me1)-QTARKSTGGKAPRKQLA-GGK (Biotin) SEQ ID NO:1 (AnaSpec 64355) and incubated for 1 hour at 25° C. Reactions were stopped by addition of 10 µL 1×LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). The salts of the present disclosure have been tested and found to be active against LSD1 with an $IC_{50}$ less than 100 nM.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of inhibiting a lysine specific demethylase-1 (LSD1), said method comprising: contacting the LSD1 with a salt which is a 4-methylbenzenesulfonic acid salt of 1-((4-(methoxymethyl)-4-(((1R,2S)-2-phenylcyclopropylamino)methyl)piperidin-1-yl)methyl)cyclobutanecarboxylic acid or a hydrate or solvate thereof, wherein the salt is crystalline.

2. The method of claim 1, wherein the salt is 1-{[4-(methoxymethyl)-4-({[(1R,2S)-2-phenylcyclopropyl]amino}methyl)piperidin-1-yl]methyl}cyclobutanecarboxylic acid bis(4-methylbenzenesulfonate) or a hydrate or solvate thereof.

3. The method of claim 2, wherein the salt is a hydrate.

4. The method of claim 2, wherein the salt has Form I.

5. The method of claim 4, wherein the salt exhibits a differential scanning calorimetry thermogram having an endotherm with an onset temperature of about 94.6° C. and a peak temperature of about 103.1° C.

6. The method of claim 4, wherein the salt has an X-ray powder diffraction pattern comprising a characteristic peak at about 3.6 degrees 2-theta.

7. The method of claim 4, wherein the salt has an X-ray powder diffraction pattern comprising a characteristic peak at about 4.9 degrees 2-theta.

8. The method of claim 4, wherein the salt has an X-ray powder diffraction pattern comprising a characteristic peak at about 6.2 degrees 2-theta.

9. The method of claim 4, wherein the salt has an X-ray powder diffraction pattern comprising a characteristic peak at about 7.7 degrees 2-theta.

10. The method of claim 4, wherein the salt has an X-ray powder diffraction pattern comprising a characteristic peak at about 22.7 degrees 2-theta.

11. The method of claim 4, wherein the salt has an X-ray powder diffraction pattern comprising at least two characteristic peaks selected from the group consisting of about 3.6, about 4.9, about 6.2, about 7.7, and about 22.7 degrees 2-theta.

12. The method of claim 11, wherein the salt has an X-ray powder diffraction pattern further comprising one or more characteristic peak at a position selected from the group consisting of about 8.9, about 10.0, about 11.5, about 14.3, about 15.0, about 15.5, about 16.3, about 17.8, about 19.1, about 19.8, about 20.9, and about 22.2 degrees 2-theta, and combinations thereof.

13. The method of claim 4, wherein the salt has an X-ray powder diffraction pattern with characteristic peaks as substantially shown in FIG. 1.

14. The method of claim 4, wherein the salt has a Differential Scanning calorimetry (DSC) thermogram substantially as depicted in FIG. 2.

15. The method of claim 4, wherein the salt has a Thermal Gravimetric Analysis (TGA) thermogram substantially as depicted in FIG. 3.

16. The method of claim 4, wherein the salt exhibits a differential scanning calorimetry thermogram having an endotherm with an onset temperature of about 94.6° C. and a peak temperature of about 103.1° C.; and an X-ray powder diffraction pattern comprising a characteristic peak at about 3.6, about 4.9, about 6.2, about 7.7 or about 22.7 degrees 2-theta.

17. The method of claim 1, wherein the salt has a melting point of about 103.1° C.

18. The method of claim 3, wherein the salt has Form HI.

19. The method of claim 18, wherein the salt exhibits a differential scanning calorimetry thermogram having an endothermic peak at a temperature of about 80° C.

20. The method of claim 18, wherein the salt has an X-ray powder diffraction pattern comprising a characteristic peak selected from the group consisting of about 7.0, about 10.4, about 13.6, about 15.5, about 17.3, about 22.2, and about 24.0 degrees 2-theta.

21. The method of claim 18, wherein the salt has an X-ray powder diffraction pattern comprising two or more characteristic peaks selected from the group consisting of about 7.0, about 10.4, about 13.6, about 15.5, about 17.3, about 22.2, and about 24.0 degrees 2-theta.

22. The method of claim 18, wherein the salt has an X-ray powder diffraction pattern comprising three or more characteristic peaks selected from the group consisting of about 7.0, about 10.4, about 13.6, about 15.5, about 17.3, about 22.2, and about 24.0 degrees 2-theta.

23. The method of claim 18, wherein the salt has an X-ray powder diffraction pattern substantially as shown in FIG. 4.

24. The method of claim 18, wherein the salt has a DSC thermogram substantially as depicted in FIG. 5.

25. The method of claim 18, wherein the salt has a TGA thermogram substantially as depicted in FIG. 6.

26. The method of claim 18, wherein the salt exhibits a differential scanning calorimetry thermogram having an endothermic peak at a temperature of about 80° C.; and an X-ray powder diffraction pattern comprising a characteristic peak selected from the group consisting of about 7.0, about 10.4, about 13.6, about 15.5, about 17.3, about 22.2, and about 24.0 degrees 2-theta.

27. The method of claim 3, wherein the salt has Form HII.

28. The method of claim 27, wherein the salt exhibits a differential scanning calorimetry thermogram having an endothermic peak at a temperature of about 52° C.

29. The method of claim 27, wherein the salt has an X-ray powder diffraction pattern comprising a characteristic peak selected from the group consisting of about 8.7, about 10.1, about 14.8, about 21.3, about 22.0, about 22.7, and about 24.3 degrees 2-theta.

30. The method of claim 27, wherein the salt has an X-ray powder diffraction pattern comprising two or more characteristic peaks selected from the group consisting of about 8.7, about 10.1, about 14.8, about 21.3, about 22.0, about 22.7, and about 24.3 degrees 2-theta.

31. The method of claim 27, wherein the salt has an X-ray powder diffraction pattern comprising three or more characteristic peaks selected from the group consisting of about 8.7, about 10.1, about 14.8, about 21.3, about 22.0, about 22.7, and about 24.3 degrees 2-theta.

32. The method of claim 27, wherein the salt has an X-ray powder diffraction pattern substantially as shown in FIG. 7.

33. The method of claim 27, wherein the salt has a DSC thermogram substantially as depicted in FIG. 8.

34. The method of claim 27, wherein the salt has a TGA thermogram substantially as depicted in FIG. 9.

35. The method of claim 27, wherein the salt exhibits a differential scanning calorimetry thermogram having an endothermic peak at a temperature of about 52° C.; and
an X-ray powder diffraction pattern comprising a characteristic peak selected from the group consisting of about 8.7, about 10.1, about 14.8, about 21.3, about 22.0, about 22.7, and about 24.3 degrees 2-theta.

36. The method of claim 3, wherein the salt has Form HIII.

37. The method of claim 36, wherein the salt exhibits a differential scanning calorimetry thermogram having an endothermic peak at a temperature of about 67° C.

38. The method of claim 37, wherein the salt further exhibits an endothermic peak at a temperature of about 98° C.

39. The method of claim 36, wherein the salt has an X-ray powder diffraction pattern comprising a characteristic peak selected from the group consisting of about 7.0, about 9.0, about 9.2, about 10.2, about 17.9, about 20.3, about 22.0, and about 23.8 degrees 2-theta.

40. The method of claim 36, wherein the salt has an X-ray powder diffraction pattern comprising two or more characteristic peaks selected from the group consisting of about 7.0, about 9.0, about 9.2, about 10.2, about 17.9, about 20.3, about 22.0, and about 23.8 degrees 2-theta.

41. The method of claim 36, wherein the salt has an X-ray powder diffraction pattern comprising three or more characteristic peaks selected from the group consisting of about 7.0, about 9.0, about 9.2, about 10.2, about 17.9, about 20.3, about 22.0, and about 23.8 degrees 2-theta.

42. The method of claim 36, wherein the salt has an X-ray powder diffraction pattern substantially as shown in FIG. 10.

43. The method of claim 36, wherein the salt has a DSC thermogram substantially as depicted in FIG. 11.

44. The method of claim 36, wherein the salt has a TGA thermogram substantially as depicted in FIG. 12.

45. The method of claim 36, wherein the salt exhibits a differential scanning calorimetry thermogram having endothermic peaks at temperatures of about 67° C. and about 98° C.; and an X-ray powder diffraction pattern comprising a characteristic peak selected from the group consisting of about 7.0, about 9.0, about 9.2, about 10.2, about 17.9, about 20.3, about 22.0, and about 23.8 degrees 2-theta.

46. The method of claim 2, wherein the salt has Form DH.

47. The method of claim 46, wherein the salt exhibits a differential scanning calorimetry thermogram having an endothermic peak at a temperature of about 98° C.

48. The method of claim 46, wherein the salt has an X-ray powder diffraction pattern comprising a characteristic peak selected from the group consisting of about 7.5, about 9.6, about 10.7, about 14.8, about 20.1, about 20.7, about 21.6, about 22.9, and about 24.7 degrees 2-theta.

49. The method of claim 46, wherein the salt has an X-ray powder diffraction pattern comprising two or more characteristic peaks selected from the group consisting of about 7.5, about 9.6, about 10.7, about 14.8, about 20.1, about 20.7, about 21.6, about 22.9, and about 24.7 degrees 2-theta.

50. The method of claim 46, wherein the salt has an X-ray powder diffraction pattern comprising three or more characteristic peaks selected from the group consisting of about 7.5, about 9.6, about 10.7, about 14.8, about 20.1, about 20.7, about 21.6, about 22.9, and about 24.7 degrees 2-theta.

51. The method of claim 46, wherein the salt has an X-ray powder diffraction pattern substantially as shown in FIG. 13.

52. The method of claim 46, wherein the salt has a DSC thermogram substantially as depicted in FIG. 14.

53. The method of claim 46, wherein the salt has a TGA thermogram substantially as depicted in FIG. 15.

54. The method of claim 46, wherein the salt exhibits a differential scanning calorimetry thermogram having an endothermic peak at a temperature of about 98° C.; and
an X-ray powder diffraction pattern comprising a characteristic peak selected from the group consisting of about 7.5, about 9.6, about 10.7, about 14.8, about 20.1, about 20.7, about 21.6, about 22.9, and about 24.7 degrees 2-theta.

* * * * *

UNITED STATES PATENT AND TRADEMARK OFFICE
CERTIFICATE OF CORRECTION

PATENT NO. : 10,723,700 B2
APPLICATION NO. : 16/447841
DATED : July 28, 2020
INVENTOR(S) : Yongchun Pan et al.

Page 1 of 1

It is certified that error appears in the above-identified patent and that said Letters Patent is hereby corrected as shown below:

On the Title Page

Column 2, (Other Publications), Lines 7-8, delete "Pharamcological" and insert -- Pharmacological --.

In the Claims

Column 78, Line 26, Claim 14, delete "calorimetry" and insert -- Calorimetry --.

Signed and Sealed this
Third Day of November, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: INIT_MET
<222> LOCATION: (4)..(4)

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Gly Gly Lys
            20
```